United States Patent
Chan-Hui et al.

(10) Patent No.: US 8,609,101 B2
(45) Date of Patent: Dec. 17, 2013

(54) GRANULOCYTE-MACROPHAGE COLONY-STIMULATING FACTOR (GM-CSF) NEUTRALIZING ANTIBODIES

(75) Inventors: Po-Ying Chan-Hui, Bellevue, WA (US); Steven Frey, Redmond, WA (US); Andres G. Grandea, III, Shoreline, WA (US); Thomas C. Cox, Redmond, WA (US)

(73) Assignee: Theraclone Sciences, Inc., Seattle, WA (US)

( * ) Notice: Subject to any disclaimer, the term of this patent is extended or adjusted under 35 U.S.C. 154(b) by 285 days.

(21) Appl. No.: 12/766,444

(22) Filed: Apr. 23, 2010

(65) Prior Publication Data

US 2010/0291075 A1  Nov. 18, 2010

Related U.S. Application Data

(60) Provisional application No. 61/172,120, filed on Apr. 23, 2009, provisional application No. 61/234,946, filed on Aug. 18, 2009.

(51) Int. Cl.
*A61K 39/395* (2006.01)
*C07K 16/24* (2006.01)

(52) U.S. Cl.
USPC ............ 424/145.1; 424/130.1; 424/133.1; 424/141.1; 424/158.1; 530/387.1; 530/387.3; 530/388.1; 530/388.2; 530/388.23

(58) Field of Classification Search
None
See application file for complete search history.

(56) References Cited

U.S. PATENT DOCUMENTS

| | | | |
|---|---|---|---|
| 3,773,919 A | 11/1973 | Boswell et al. |
| 3,896,111 A | 7/1975 | Kupchan et al. |
| 4,137,230 A | 1/1979 | Hashimoto et al. |
| 4,151,042 A | 4/1979 | Higashide et al. |
| 4,248,870 A | 2/1981 | Miyashita et al. |
| 4,256,746 A | 3/1981 | Miyashita et al. |
| 4,260,608 A | 4/1981 | Miyashita et al. |
| 4,265,814 A | 5/1981 | Hashimoto et al. |
| 4,294,757 A | 10/1981 | Asai |
| 4,307,016 A | 12/1981 | Asai et al. |
| 4,308,268 A | 12/1981 | Miyashita et al. |
| 4,308,269 A | 12/1981 | Miyashita et al. |
| 4,309,428 A | 1/1982 | Miyashita et al. |
| 4,313,946 A | 2/1982 | Powell et al. |
| 4,315,929 A | 2/1982 | Freedman et al. |
| 4,317,821 A | 3/1982 | Miyashita et al. |
| 4,322,348 A | 3/1982 | Asai et al. |
| 4,331,598 A | 5/1982 | Hasegawa et al. |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,424,219 A | 1/1984 | Hashimoto et al. |
| 4,450,254 A | 5/1984 | Isley et al. |
| 4,485,045 A | 11/1984 | Regen |
| 4,544,545 A | 10/1985 | Ryan et al. |
| 4,554,101 A | 11/1985 | Hopp |
| 4,676,980 A | 6/1987 | Segal et al. |
| 4,816,567 A | 3/1989 | Cabilly et al. |
| 4,975,278 A | 12/1990 | Senter et al. |
| 5,013,556 A | 5/1991 | Woodle et al. |
| 5,019,381 A | 5/1991 | Garnick |
| 5,053,394 A | 10/1991 | Ellestad et al. |
| 5,208,020 A | 5/1993 | Chari et al. |
| 5,229,275 A | 7/1993 | Goroff |
| 5,416,064 A | 5/1995 | Chari et al. |
| 5,500,362 A | 3/1996 | Robinson et al. |
| 5,545,806 A | 8/1996 | Lonberg et al. |
| 5,545,807 A | 8/1996 | Surani et al. |
| 5,567,610 A | 10/1996 | Borrebaeck et al. |
| 5,569,825 A | 10/1996 | Lonberg et al. |
| 5,571,894 A | 11/1996 | Wels et al. |
| 5,587,458 A | 12/1996 | King et al. |
| 5,591,669 A | 1/1997 | Krimpenfort et al. |
| 5,627,052 A | 5/1997 | Schrader |
| 5,641,870 A | 6/1997 | Rinderknecht et al. |
| 5,648,237 A | 7/1997 | Carter |
| 5,712,374 A | 1/1998 | Kuntsmann et al. |
| 5,714,586 A | 2/1998 | Kunstmann et al. |
| 5,731,168 A | 3/1998 | Carter et al. |
| 5,739,116 A | 4/1998 | Hamann et al. |
| 5,739,277 A | 4/1998 | Presta et al. |
| 5,767,285 A | 6/1998 | Hamann et al. |
| 5,770,701 A | 6/1998 | McGahren et al. |
| 5,770,710 A | 6/1998 | McGahren et al. |

(Continued)

FOREIGN PATENT DOCUMENTS

EP  183070 A2  6/1986
EP  244234 A2  11/1987

(Continued)

OTHER PUBLICATIONS

Rudikoff et al., Proc Natl Acad Sci USA 79: 1979-1983, 1982.*
Colman, Research in Immunology 145: 33-36, 1994.*
Kussie et al., J. Immunol. 152: 146-152, 1994.*
Chen et al., EMBO J., 14: 2784-2794, 1995.*
Borrello et al. "Short Survey GM-CSF-Based Cellular Vaccines: A Review of the Clinical Experience." *Cytokine Growth Factor Rev.* 13.2(2002):185-193.
Dessain et al. "Exploring the Native Human Antibody Repertoire to Create Antiviral Therapeautics." *Curr. Topics Microbiol. Immunol.* 317(2008):155-183.
Altschul et al. "Basic Local Alignment Search Tool." *J. Mol. Biol.* 215.3(1990):403-410.

(Continued)

*Primary Examiner* — Phillip Gambel
(74) *Attorney, Agent, or Firm* — Mintz Levin Cohn Ferris Glovsky and Popeo, P.C.; Ivor R. Elrifi; Katherine J. Miller

(57) ABSTRACT

The invention provides a GM-CSF neutralizing human monoclonal antibody, 1783J22, as well as methods of making and use thereof. The monoclonal antibody is further characterized by its ability to bind epitopes from GM-CSF proteins of multiple species.

20 Claims, 10 Drawing Sheets

(56) References Cited

U.S. PATENT DOCUMENTS

| | | | |
|---|---|---|---|
| 5,773,001 A | 6/1998 | Hamann et al. | |
| 5,789,199 A | 8/1998 | Joly et al. | |
| 5,821,337 A | 10/1998 | Carter et al. | |
| 5,837,234 A | 11/1998 | Gentile et al. | |
| 5,840,523 A | 11/1998 | Simmons et al. | |
| 5,869,046 A | 2/1999 | Presta et al. | |
| 5,877,296 A | 3/1999 | Hamann et al. | |
| 6,331,415 B1 | 12/2001 | Cabilly et al. | |
| 6,331,562 B1 | 12/2001 | Bhagwat et al. | |
| 6,824,780 B1 | 11/2004 | Devaux et al. | |
| 7,112,439 B2 | 9/2006 | Johnson et al. | |
| 2002/0141994 A1 | 10/2002 | Devalaraja et al. | |
| 2003/0130496 A1 | 7/2003 | Winter et al. | |
| 2007/0134248 A1* | 6/2007 | Denney et al. | 424/155.1 |
| 2008/0206241 A1* | 8/2008 | Bebbington et al. | 424/133.1 |
| 2008/0292641 A1 | 11/2008 | Sass et al. | |
| 2009/0053213 A1* | 2/2009 | Steidl et al. | 424/133.1 |

FOREIGN PATENT DOCUMENTS

| | | |
|---|---|---|
| EP | 402226 A1 | 12/1990 |
| EP | 404097 A2 | 12/1990 |
| EP | 0425235 B1 | 5/1991 |
| WO | WO-8101145 A1 | 4/1981 |
| WO | WO-8807378 A1 | 10/1988 |
| WO | WO-9013646 A1 | 11/1990 |
| WO | WO-9100360 A1 | 1/1991 |
| WO | WO-9202551 A1 | 2/1992 |
| WO | WO-9220373 A1 | 11/1992 |
| WO | WO-9308829 A1 | 5/1993 |
| WO | WO-9311161 A1 | 6/1993 |
| WO | WO-9404690 A1 | 3/1994 |
| WO | WO-9411026 A2 | 5/1994 |
| WO | WO-9425591 A1 | 11/1994 |
| WO | WO-9616673 A1 | 6/1996 |
| WO | WO-9717852 A1 | 5/1997 |
| WO | WO-9738731 A1 | 10/1997 |
| WO | WO-9802463 A1 | 1/1998 |
| WO | WO-03068924 A2 | 8/2003 |
| WO | WO-2004076677 A2 | 9/2004 |
| WO | WO-2006122797 A2 | 11/2006 |
| WO | WO-2007092939 A2 | 8/2007 |
| WO | WO-2007110631 A1 | 10/2007 |
| WO | WO-2009038760 A2 | 3/2009 |

OTHER PUBLICATIONS

Altschul et al. "Gapped Blast and PSI-Blast: A New Generation of Protein Database Search Programs." *Nucl. Acids Res.* 25.17(1997):3389-3402.

Antman et al. "Effect of Recombinant Human Granulocyte-Macrophage Colony-Stimulating Factor on Chemotherapy-Induced Myelosuppression." *New Eng. J. Med.* 319.10(1988):593-598.

Arnon et al. "Monoclonal Antibodies for Immunotargeting of Drugs in Cancer Therapy." *Monoclonal Antibodies Cancer and Therapy.* Reisfeld et al., eds. New York: Alan R. Liss, Inc. (1985):243-256.

ATCC Accession No. 12424.
ATCC Accession No. 16045.
ATCC Accession No. 24178.
ATCC Accession No. 27325.
ATCC Accession No. 31446.
ATCC Accession No. 31537.
ATCC Accession No. 36906.
ATCC Accession No. 56500.
ATCC Accession No. CCL10.
ATCC Accession No. CCL2.
ATCC Accession No. CCL34.
ATCC Accession No. CCL51.
ATCC Accession No. CCL70.
ATCC Accession No. CCL75.
ATCC Accession No. CRL1442.
ATCC Accession No. CRL1587.
ATCC Accession No. CRL1651.

Atkinson et al. "Recombinant Human Granulocyte-Macrphage Colony-Stimulating Factor (rH GM-CSF) Regulates fMet-Leu-Phe Receptors on Human Neutrophils." *Immunol.* 64(1988):519-525.

Babcook et al. "A Novel Strategy for Generating Monoclonal Antibodies from Single, Isolated Lymphocytes Producing Antibodies of Defined Specificities." *PNAS.* 93.15(1996):7843-7848.

Beffy et al. "An Immunodominant Epitope in a Functional Domain Near the N-Terminus of Human Granulocyte-Macrophage Colony-Stimulating Factor Identified by Cross-Reaction of Synthetic Peptides with Neutralizing Anti-Protein and Anti-Peptide Antibodies." *Hybridoma.* 13.6(1994):457-468.

Bird et al. "Single-Chain Antigen-Binding Proteins." *Science.* 242(1988):423-426.

Bitter et al. "Expression and Secretion Vectors for Yeast." *Meth. Enzymol.* 153(1987):516-544.

Bolton et al. "The Labelling of Proteins to High Specific Radioactives by Conjugation to a 125I-Containing Acylating Agent." *Biochem. J.* 133.3(1973):529-538.

Brandt et al. "Effect of Recombinant Human Granulocyte-Macrophage Colony-Stimulating Factor on Hematopoietic Reconstitution after High-Dose Chemotherapy and Autologous Bone Marrow Transplantation." *New. Eng. J. Med.* 318.14(1988):869-876.

Brennan et al. "Preparation of Bispecific Antibodies by Chemical Recombination of Monoclonal Immunoglobulin G1 Fragments." *Science.* 229(1985):81-83.

Broglie et al. "Light-Regulated Expression of a Pea Ribulose-1,5-Bisphosphate Carboxylase Small Subunit Gene in Transformed Plant Cells." *Science.* 224(1984):838-843.

Brüggemann et al. "Designer Mice: The Production of Human Antibody Repertoires in Transgenic Animals." *The Year in Immunology: Generation of Antibodies by Cell and Gene Immortalization.* Terhorst et al., eds. New York: Karger. 7(1993):33-40.

Buchacher et al. "Generation of Human Monoclonal Antibodies Against HIV-1 Proteins; Electrofusion and Epstein-Barr Virus Transformation for Peripheral Blood Lymphocyte Immortalization." *AIDS Res. Hum. Retroviruses.* 10.4(1994):359-369.

Burgess et al. "The Nature and Action of Granulocyte-Macrophage Colony Stimulating Factors." *Blood.* 56(1980):947-958.

Cantrell et al. "Cloning, Sequence, and Expression of a Human Granulocyte/Macrophage Colony-Stimulating Factor." *PNAS.* 82.18(1985):6250-6254.

Capel et al. "Heterogeneity of Human IgG Fc Receptors." *ImmunoMeth.* 4.1(1994):25-34.

Carlsson et al. "Protein Thiolating and Reversible Protein-Protein Conjugation." *Biochem. J.* 173(1978):723-737.

Caron et al. "Engineered Humanized Dimeric Forms of IgC are More Effective Antibodies." *J. Exp. Med.* 176(1992):1191-1195.

Carter et al. "High Level *Escherichia coli* Expression and Production of a Bivalent Humanized Antibody Fragment." *Bio/Technology.* 10(1992):163-167.

Chari et al. "Immunoconjugates Containing Novel Maytansinoids: Promising Anticancer Drugs." *Cancer Res.* 52(1992):127-131.

Chothia et al. "Canonical Structures for the Hypervariable Regions of Immunoglobulins." *J. Mol. Biol.* 196.4(1987):901-917.

Clackson et al. "Making Antibody Fragments Using Phage Display Libraries." *Nature.* 352(1991):624-628.

Clark et al. et al. "The Human Hematopoietic Colony-Stimulating Factors." *Science.* 236(1987):1229-1237.

Clynes et al. "Fc Receptors are Required in Passive and Active Immunity to Melanoma." *PNAS.* 95.2(1998):652-656.

Coffey et al. "Stimulation of Guanylate Cyclase Activity and Reduction of Adenylate Cyclase Activity by Granulocyte-Macrophage Colony-Stimulating Factor in Human Blood Neutrophils." *J. Immunol.* 140.8(1988):2695-2701.

Colbére-Garapin et al. "A New Dominant Hybrid Selective Marker for Higher Eukoaryotic Cells." *J. Mol. Biol.* 150.1(1981):1-14.

Coruzzi et al. "Tissue-Specific and Light-Regulated Expression of a Pea Nuclear Gene Encoding the Small Subunit of Ribulose-1,5-bisphosphate Carboxylase." *EMBO J.* 3.8(1984):1671-1679.

Cunningham et al. "High-Resolution Epitope Mapping of hGH-Receptor Interactions by Alanine-Scanning Mutagenesis." *Science.* 244(1989):1081-1085.

(56) References Cited

OTHER PUBLICATIONS

Dayhoff et al. "A Model of Evolutionary Change in Proteins." *Atlas of Protein Sequence and Structure*. Washington, D.C.: National Biomedical Research Foundation. Dayhoff, ed. 5.S3(1978):345-358.
Daëron. "Fc Receptor Biology." *Annu. Rev. Immuno.* 15(1997):203-234.
de Haas et al. "Fcγ Receptors of Phagocytes." *J. Lab. Clin. Med.* 126(1995):330-341.
Deepe et al. "Neutralization of Endogenous Granulocyte-Macrophage Colony-Stimulating Factor Subverts the Protective Immune Response to *Histoplasma capsulatum*." *J. Immunol.* 163(1999):4985-4993.
Dempsey et al. "Monoclonal Antibodies that Recognize Human Granulocyte-Macrophage Colony-Stimulating Factor and Neutralize its Bioactivity In Vitro." *Hybridoma.* 9.6(1990):545-558.
Eisenbarth et al. "Lipopolysaccharide-Enhanced, Toll-Like Receptor 4-Dependent T Helper Cell Type 2 Responses to Inhaled Antigen." *J. Exp. Med.* 196.12(2002):1645-1651.
Emanuel et al. "Selective Hypersensitivty to Granulocyte-Macrophage Colony-Stimulating Factor by Juvenile Chronic Myeloid Leukemia Hematopoietic Progenitors." *Blood.* 77.5(1991):925-929.
Emanuel. "Juvenile Myelomonocytic Leukemia." *Curr. Hematol. Rep.* 3.3(2004):203-209.
Engelhard et al. "The Insect Tracheal System: A Conduit for the Systemic Spread of *Autographa californica* M Nuclear Polyhedrosis Virus." *PNAS.* 91.8(1994):3224-3227.
Eppstein et al. "Biological Activity of Liposome-Encapsulated Murine Interferon γ is Mediated by a Cell Membrane Receptor." *PNAS.* 82.11(1985):3688-3692.
Fraker et al. "Protein and Cell Membrane Iodinations with a Sparingly Soluble Chloroamide, 1,3,4,6-Tetrachloro-3a,6a-Diphenylglycoluril." *Biochem. Biophys. Res. Commun.* 80.4(1978):849-857.
Gabizon et al. "Pharmacokinetics and Tissue Distribution of Doxorubicin Encapsulated in Stable Liposome with Long Circulation Times." *J. Natl. Cancer Inst.* 81.19(1989):1484-1488.
Gajewska et al. "GM-CSF and Dendritic Cells in Allergic Airway Inflammation: Basic Mechanisms and Prospects for Therapeutic Intervention." *Curr. Drug Targets Inflamm. Allergy.* 2.4(2003):279-292.
Gamble et al. "Stimulation of the Adherence of Neutrophils to Umbilical Vein Endothelium by Human Recombinant Tumor Necrosis Factor." *PNAS.* 82.24(1985):8667-8671.
Gazzano-Santoro et al. "A Non-Radioactive Complement-Dependent Cytotoxicity Assay for Anti-CD20 Monoclonal Antibody." *J. Immunol. Meth.* 202.2(1997):163-171.
GenBank Accession No. AF168801.
GenBank Accession No. AY998683.
GenBank Accession No. AY998685.
GenBank Accession No. AY998691.
GenBank Accession No. AY998715.
GenBank Accession No. EF589383.
GenBank Accession No. EF589385.
GenBank Accession No. EF589393.
GenBank Accession No. EF589394.
GenBank Accession No. EF589439.
GenBank Accession No. EF589441.
GenBank Accession No. EF589464.
GenBank Accession No. EF589472.
GenBank Accession No. EF589477.
GenBank Accession No. EF589481.
GenBank Accession No. EF589488.
GenBank Accession No. EF589492.
GenBank Accession No. EF589502.
GenBank Accession No. EF589555.
GenBank Accession No. EF589569.
GenBank Accession No. EU599329.
Graham et al. "Characteristics of a Human Cell Line Transformed by DNA from Human Adenovirus Type 5." *J. Virol.* 36(1977):59-72.
Gruber et al. "Efficient Tumor Cell Lysis Mediated by a Bispecific Single Chain Antibody Expressed in *Escherichia coli*." *J. Immunol.* 152(1994):5368-5374.
Guss et al. "Structure of the IgG-Binding Regions of Streptococcal Protein G." *EMBO J.* 5.7(1986):1567-1575.
Guyer et al. "Immunoglobulin Binding by Mouse Intestinal Epithelial Cell Receptors." *J. Immunol.* 117.2(1976):587-593.
Hamilton et al. "Stimulation of Macrophage Plasminogen Activator Activity by Colony-Stimulating Factors." *J. Cell Physiol.* 103.3(1980):435-445.
Hamilton. "GM-CSF in Inflammation and Autoimmunity." *Trends Immun.* 23.8(2002):403-408.
Hancock et al. "Recombinant Granulocyte-Macrophage Colony-Stimulating Factor Down-Regulates Expression of IL-2 Receptor on Human Mononuclear Phagocytes by Induction of Prostaglandin E." *J. Immunol.* 140.9(1988):3021-3025.
Handman et al. "Stimulation by Granulocyte-Macrophage Colony-Stimulating Factor of *Leishmania Tropica* Killing by Macrophages." *J. Immunol.* 122.3(1979):1134-1137.
Hart et al. "Synergistic Activation of Human Monocytes by Granulocyte-Macrophage Colony-Stimulating Factor and IFN-γ." *J. Immunol.* 141.5(1988):1516-1521.
Hartman et al. "Two Dominant-Acting Selectable Markers for Gene Transfer Studies in Mammalian Cells." *PNAS.* 85.21(1988):8047-8051.
Hazenberg et al. "Correction of Granulocytopenia in Felty's Syndrome by Granulocyte-Macrophage Colony-Stimulating Factor." *Blood.* 74.8(1989):2769-2773.
Hein. "Unified Approach to Alignment and Phylogenes." *Meth. Enzymol.* 183(1990):626-645.
Hellström et al. "Antibodies for Drug Delivery." *Controlled Drug Delivery.* New York: Marcel Dekker, Inc. 29(1987):623-653.
Henikoff et al. "Amino Acid Substitution Matrices from Protein Blocks." *PNAS.* 89(1992):10915-10919.
Higgins et al. "Fast and Sensitive Multiple Sequence Alignments on a Microcomputer." *CABIOS.* 5.2(1989):151-153.
Hobbs et al. "Genetic Engineering." *McGraw Hill Yearbook of Science and Technology.* New York: McGraw Hill. (1992):189-196.
Holliger et al. "'Diabodies': Small Bivalent and Bispecific Antibody Fragments." *PNAS.* 90(1993):6444-6448.
Honegger et al. "Yet Another Numbering Scheme for Immunoglobulin Variable Domains: An Automatic Modeling and Analysis Tool." *J. Mol. Biol.* 309.3(2001):657-670.
Hwang et al. "Hepatic Uptake and Degradation of Unilamellar Sphingomyelin/Cholesterol Liposomes: A Kinetic Study." *PNAS.* 77.7(1980):4030-4034.
Jakobovits et al. "Analysis of Homozygous Mutant Chimeric Mice: Deletion of the Immunoglobulin Heavy-Chain Joining Region Blocks B-Cell Development and Antibody Production." *PNAS.* 90.6(1993):2551-2555.
Jakobovits et al. "Germ-Line Transmission and Expression of a Human-Derived Yeast Artificial Chromosome." *Nature.* 362(1993):255-258.
Jones et al. "Replacing the Complementarity-Determining Regions in a Human Antibody With Those from a Mouse." *Nature.* 321(1986):522-525.
Karpas et al. "A Human Myeloma Cell Line Suitable for the Generation of Human Monoclonal Antibodies." *PNAS.* 98.4(2001):1799-1804.
Khapli et al. "IL-3 Acts Directly on Osteoclast Precursors and Irreversibly Inhibits Receptor Activator of NF-κB Ligand-Induced Osteoclast Differentiation by Diverting the Cells to Macrophage Lineage." *J. Immunol.* 171(2003):142-151.
Kim et al. "Localization of the Site of the Murine IgG1 Molecule that is Involved in Binding to the Murine Intestinal Fc Receptor." *Eur. J. Immunol.* 24(1994):2429-2434.
Kim et al. "MCP-1 is Induced by Receptor Activator of Nuclear Factor-κb Ligand, Promotes Human Osteoclast Fusion, and Rescues Granulocyte Macrophage Colony-Stimulating Factor Suppression of Osteoclast Formation." *J. Biol. Chem.* 280.16(2005):16163-16169.
Kostelny et al. "Formation of a Bispecific Antibody by the Use of Leucine Zippers." *J. Immunol.* 148.5(1992):1547-1553.

(56) References Cited

OTHER PUBLICATIONS

Kroll et al. "A Multifunctional Prokaryotic Protein Expression System: Overproduction, Affinity Purification and Selective Detection." *DNA Cell Biol.* 12.5(1993):441-453.

Kurland et al. "Induction of Prostaglandin E Synthesis in Normal and Neoplastic Macrophages: Role for Colony-Stimulating Factor(s) Distinct From Effects on Myeloid Progenitor Cell Proliferation." *PNAS.* 76.5(1979):2326-2330.

Kyte et al. "A Simple Method for Displaying the Hydropathic Character of a Protein." *J. Mol. Biol.* 157.1(1982):105-132.

Köhler et al. "Continuous Cultures of Fused Cells Secreting Antibody of Predefined Specificity." *Nature.* 256(1975):495-497.

Lang et al. "Transgenic Mice Expressing a Hemopoietic Growth Factor Gene (GM-CSF) Develop Accumulations of Macrophages, Blindness, and a Fatal Syndrome of Tissue Damage." *Cell.* 51(1987):675-686.

Larkin et al. "Clustal W and Clustal X Version 2.0." *Bioinformatics.* 23.21(2007):2947-2948.

Latzin et al. "Anti-GM-CSF Antibodies in Paediatric Pulmonary Alveolar Proteinosis." *Thorax.* 60.1(2005):39-44.

Lefranc et al. "IMGT Unique Numbering for Immunoglobulin and T Cell Receptor Variable Domains and Ig Superfamily V-Like Domains." *Dev. Comp. Immunol.* 27.1(2003):55-77.

Lefranc et al. "IMGT, The International ImMunoGeneTics Database." *Nucl. Acids Res.* 27.1(1999):209-212.

Lefranc et al. "The IMGT Unique Numbering for Immunoglobulins, T Cell Receptors and Ig-Like Domains." *The Immunologist.* 7.4(1999):132-136.

Lefranc et al. "Unique Database Numbering System for Immunogenetic Analysis." *Immunol. Today.* 18.11(1997):509-510.

Li et al. "Human Antibodies for Immunotherapy Development Generated via a Human B Cell Hybridoma Technology." *PNAS.* 103.10(2006):3557-3562.

Lindmark et al. "Binding of Immunoglobulins to Protein A and Immunoglobulin Levels in Mammalian sera." *J. Immunol. Meth.* 62.10(1983):1-13.

Liu et al. "Eradication of Large Colon Tumor Xenografts by Targeted Delivery of Maytansinoids." *PNAS.* 93.16(1996):8618-8623.

Logan et al. "Adenovirus Tripartite Leader Sequence Enhances Translation of mRNAs Late After Infection." *PNAS.* 81.12(1984):3655-3659.

Lowy et al. "Isolation of Transforming DNA: Cloning the Hamster aprt Gene." *Cell.* 22.3(1980):817-823.

Maddox et al. "Elevated Serum Levels in Human Pregnancy of a Molecule Immunochemically Similar to Eosinophil Granule Major Basic Protein." *J. Exp. Med.* 158(1983):1211-1226.

Manczak et al. "Neutralization of Granulocyte Macrophage Colony-Stimulating Factor Decreases Amyloid Beta 1-42 and Suppresses Microglial Activity in a Transgenic Mouse Model of Alzheimer's Disease." *Hum. Mol. Genet.* 18.20(2009):3876-3893.

Marks et al. "By-Passing Immunization: Human Antibodies from V-Gene Libraries Displayed on Phage." *J. Mol. Biol.* 222.3(1991):581-597.

Martin et al. "Irreversible Coupling of Immunoglobulin Fragments to Preformed Vesicles." *J. Biol. Chem.* 257.1(1982):286-288.

Massey. "Catalytic Antibodies Catching On." *Nature.* 328(1987):457-458.

Mather et al. "Culture of Testicular Cells in Hormone-Supplemented Serum-Free Medium." *Ann. N.Y. Acad. Sci.* 383(1982):44-68.

Mather. "Establishment and Characterization of Two Distince Mouse Testicular Epithelial Cell Lines." *Biol. Reprod.* 23.1(1980):243-252.

McQualter et al. "Granulocyte Macrophage Colony-Stimulating Factor: A New Putative Therapeutic Target in Multiple Sclerosis." *J. Exp. Med.* 194.7(2001):873-881.

Metcalf. "The Granulocyte-Macrophage Colony-Stimulating Factors." *Science.* 229(1985):16-22.

Metcalf. "The Molecular Biology and Functions of the Granulocyte-Macrophage Colony-Stimulating Factors." *Blood.* 67.2(1987):257-267.

Milstein et al. "Hybrid Hybridomas and Their Use in Immunohistochemistry." *Nature.* 305(1983):537-540.

Miyamoto et al. "Bifurcation of Osteoclasts and Dendritic Cells from Common Progenitors." *Blood.* 98.8(2001):2544-2554.

Morimoto et al. "Single-Step Purification of F(ab')$_2$ Fragments of Mouse Monoclonal Antibodies (Immunoglobulins G1) by Hydrophobic Interaction High Performance Liquid Chromatography using TSKgel Phenyl-5PW." *J. Biochem. Biophys. Methods.* 24.1-2(1992):107-117.

Morrison et al. "Chimeric Human Antibody Molecules: Mouse Antigen-Binding Domains with Human Constant Region Domains." *PNAS.* 81.21(1984):6851-6855.

Morrison. "The Determination of the Exposed Proteins on Membranes by the Use of Lactoperoxidase." *Methods in Enzymology: Biomembranes: Part B.* New York: Academic Press. Fleischer et al., eds. 3.2(1974):103-109.

Morstyn et al. "Early Clinical Trials with Colony-Stimulating Factors." *Cancer Invest.* 7.5(1989):443-456.

Murakami et al. "Cell Cycle Regulation, Oncogenes, and Antineoplastic Drugs." The Molecular Basis of Cancer. Mendelsohn et al., eds. Philadelphia: WB Saunders. (1995)1-17.

Muster et al. "A Conserved Neutralizing Epitope on gp41 of Human Immunodeficiency Virus Type 1." *J. Virol.* 67.11(1993):6642-6647.

Myers et al. "Optimal Alignments in Linear Space." *CABIOS.* 4.1(1988):11-17.

Myint et al. "Granulocyte/Macrophage Colony-Stimulating Factor and Interleukin-3 Correct Osteopetrosis in Mice with Osteopetrosis Mutation." *Am. J. Pathol.* 154.2(1999):553-556.

Needleman et al. "A General Method Applicable to the Search for Similarities in the Amino Acid Sequence of Two Proteins." *J. Mol. Biol.* 48.3(1970):443-453.

Neuberger et al. "Recombinant Antibodies Possessing Novel Effctor Functions." *Nature.* 312(1984):604-608.

Nimer et al. "Serum Cholesterol-Lowering Activity of Granulocyte-Macrophage Colony-Stimulating Factor." *JAMA.* 260.22(1988):3297-3300.

Order. "Analysis, Results, and Future Prespoective of the Therapeutic Use of Radiolabeled Antibody in Cancer Therapy." *Monoclonal Antibodies for Cancer Detection and Therapy.* New York: Academic Press. (1985):303-316.

Pearson et al. "Improved Tools for Biological Sequence Comparison." *PNAS.* 85(1988):2444-2448.

Plückthun et al. "Expression of Functional Antibody Fv and Fab Fragments in *Escherichia coli.*" *Meth. Enzymol.* 178(1989):497-515.

Plückthun. "Antibodies from *Escherichia coli.*" *The Pharmacology of Monoclonal Antibodies.* New York: Springer-Verlag. Rosenberg et al., eds. 113(1994):269-315.

Porath. "Immobilized Metal Ion Affinity Chromatography." *Prot. Exp. Purif.* 3.4(1992):263-281.

Presta. "Antibody Engineering." *Curr. Op. Struct. Biol.* 3.4(1992):593-596.

Ravetch et al. "Fc Receptors." *Annu. Rev. Immunol.* 9(1991):457-492.

Rhodes et al. "Transformation of Maize by Electroporation of Embryos." *Methods Mol. Biol.* 55(1995):121-131.

Riechmann et al. "Reshaping Human Antibodies for Therapy." *Nature.* 332(1988):323-327.

Robinson. "Comparison of Label Tree with Valency Three." *J. Combin. Ther. Ser. B.* 11(1971):105-119.

Ruiz et al. "IMGT, The International ImMunoGeneTics Database." *Nucl. Acids Res.* 28.1(2000):219-221.

Sachs. "The Molecular Control of Blood Cell Development." *Science.* 238(1987):1374-1379.

Saitou et al. "The Neighbor-Joining Method: A New Method for Reconstructing Phylogenetic Trees." *Mol. Biol. Evol.* 4.4(1987):406-425.

Sanger et al. "DNA Sequencing with Chain-Terminating Inhibitors." *PNAS.* 74.12(1977):5463-5467.

Scatchard. "The Attractions of Proteins for Small Molecules and Ions." *Ann. N.Y. Acad. Sci.* 51(1949):660-672.

Selgas et al. "Immunomodulation of Peritoneal Macrophages by Granulocyte-Macrophage Colony-Stimulating Factor in Humans." *Kidney Int.* 50(1996):2070-2078.

(56) References Cited

OTHER PUBLICATIONS

Shalaby et al. "Development of Humanized Bispecific Antibodies Reactive with Cytotoxic Lumphocytes and Tumor Cells Overexpressing the *HER2* Protooncogene." *J. Exp. Med.* 175(1992):217-225.

Shopes. "A Genetically Engineered Human IgG Mutant with Enhanced Cytolytic Activity." *J. Immunol.* 148.9(1992):2918-2922.

Shuto et al. "Dexamethasone Stimulates Osteoclast-Like Cell Formation by Inhibiting Granulocyte-Macrophage Colony-Stimulating Factor Production in Mouse Bone Marrow Cultures." *Endocrinol.* 134.3(1994):1121-1126.

Smith et al. "Comparison of Biosequences." *Adv. Appl. Math.* 2.4(1981):482-489.

Stevenson et al. "A Chimeric Antibody with Dual Fc Receptor Regions (*bis*FabFc) Prepared b Manipulations at the IgG Hinge." *Anti-Cancer Drug Des.* 3.4(10989):219-230, 1989.

Stites et al., ed. *Basic and Clinical Immunology*. Norwalk, CT: Appleton & Lange. 8(1994):71.

Suresh et al. "Bispecific Monoclonal Antibodies from Hybrid Hybridomas." *Meth. Enzymol.* 121(1986):210-228.

Syvanen et al. "Preparation of 125I-Catalytic Subunit of Aspartate Transcarbamylase and Its Use in Studies of the Regulatory Subunit." *J. Biol. Chem.* 248.11(1973):3762-3768.

Takamatsu et al. "Expression of Bacterial Chloramphenicol Acetyltransferase Gene in Tobacco Plants Mediated by TMV-RNA." *EMBO J.* 6.2(1987):307-311.

Tarkowski et al. "Local and Systemic GM-CSF Increase in Alzheimer's Disease and Vascular Dementia." *Acta Neurol. Scand.* 103.3(2001):166-174.

Thompson et al. "Clustal W: Improving the Sensitivity of Progressive Multiple Sequence Alignment Through Sequence Weighting, Position-Specific Gap Penalties and Weight Matric Choice." *Nucl. Acids Res.* 22.22(1994):4673-4680.

Thorpe et al. "The Preparation and Cytotoxic Properties of Antibody-Toxin Conjugates." *Immunol Rev.* 62.1(1982):119-158.

Thorpe. "Antibody Carriers of Cytotoxic Agents in Cancer Therapy: A Review." *Monoclonal Antibodies '84: Biological and Clinical Applications*. (1985):475-506.

Traggiai et al. "An Efficient Method to Make Human Monoclonal Antibodies from Memory B Cells: Potent Neutralization of SARS Coronavirus." *Nat. Med.* 10.8(2004):871-875.

Traunecker et al. "Bispecific Single Chain Molecules (Janusins) Target Cytotoxic Lymphocytes on HIV Infected Cells." *EMBO J.* 10.12(1991):3655-3659.

Tutt et al. "Trispecific F(ab')3 Derivatives that Use Cooperative Signaling via the TCR/CD3 Complex and CD2 to Activate and Redirect Resting Cytotoxic T Cells." *J. Immunol.* 147.1(1991):60-69.

Urlaub et al. "Isolation of Chinese Hamster Cell Mutants Deficient in Dihydrofolate Reductase Activity." *PNAS.* 77.7(1980):4216-4220.

Van Heeke et al. "Expression of Human Asparagine Synthetase in *Escherichia coli.*" *J. Biol. Chem.* 264.10(1989):5503-5509.

Verhoeyen et al. "Reshaping Human Antibodies: Grafting an Antilysozyme Activity." *Science.* 239(1988):1534-1536.

Vitetta et al. "Redesigning Nature's Poisons to Create Anti-Tumor Reagents." *Science.* 238(1987):1098-1104.

Volmar et al. "The Granulocyte Macrophage Colony Stimulating Factor (GM-CSF) Regulates Amyloid $\beta(A\beta)$ Production." *Cytokine.* 42.3(2008):336-344.

Weisbart et al. "GM-CSF Induces Human Neutrophil IgA-Mediated Phagocytosis by an IgA Fc Receptor Activation Mechanism." *Nature.* 332(1988):647-648.

Weitkamp et al. "Infant and Human B Cell Responses to Rotavirus Share Common Immunodeficient Variable Gene Repertoires." *J. Immunol.* 171(2003):4680-4688.

Wigler et al. "Transfer of Purified Herpes Virus Thymidine Kinase Gene to Cultured Mouse Cells." *Cell.* 11.1(1977):223-232.

Wigler et al. "Transformation of Mammalian Cells with an Amplifiable Dominant-Acting Gene." *PNAS.* 77.6(1980):3567-3570.

Wilbur et al. "Rapid Similarity Searches of Nucleic Acid and Protein Data Banks." *PNAS.* 80.3(1983):726-730.

Winter et al. "The Expression of Heat Shock Protein and Cognate Genes During Plant Development." *Results Probl. Cell Differ.* 17(1991):85-105.

Wolff et al. "Monoclonal Antibody Homodimers: Enhanced Antitumor Activity in Nude Mice." *Cancer Res.* 53(1993):2560-2565.

Wong et al. "Human GM-CSF: Molecular Cloning of the Complementary DNA and Purification of the Natural and Recombinant Proteins." *Science.* 228(1985):810-815.

Yamashita et al. "Attenuation of Airway Hyperresponsiveness in a Murine Asthma Model by Neutralization of Granulocyte-Macrophage Colony-Stimulating Factor (GM-CSF)." *Cell. Immunol.* 219. 2(2002):92-97.

Yaniv. "Enhancing Elements for Activation of Eukaryotic Promoters." *Nature.* 297(1982):17-18.

Zapata et al. "Engineering Linear F(ab')2 Fragments for Efficient Production in *Escherichia coli* and Enhanced Antiproliferative Actvity." *Protein Eng.* 8.10(1995):1057-1062.

Zsengeller et al. "Adenovirus-Mediated Granulocyte-Macrophage Colony-Stimulating Factor Improves Lung Pathology of Pulmonary Alveolar Proteinosis in Granulocyte-Macrophage Colony-Stimulating Factor-Deficient Mice." *Hum. Gene Ther.* 9(1998):2101-2109.

\* cited by examiner

SEQUENCE LISTING

<160> NUMBER OF SEQ ID NOS: 16

<210> SEQ ID NO 1
<211> LENGTH: 1419
<212> TYPE: DNA
<213> ORGANISM: Homo sapiens

<400> SEQUENCE: 1

| | | | | | |
|---|---|---|---|---|---|
| atggagtttg | ggctgagctg | gcttttctt | gtgactgttc | taaaaggtgt | ccactgtgag | 60 |
| gtccaattat | tgcagtcggg | ggggggcctg | acacatcctg | ggggtccct | gagactctca | 120 |
| tgtgcggcgt | ctggcttccc | ctttcacaaa | tataccatga | cttgggtccg | ccagcctcca | 180 |
| gggaagggcc | tggagtgggt | ctcaagtgtt | agtggtgtca | acggcaagac | atattatagt | 240 |
| ccctccgtga | ggggccgcgc | catcgtctcc | agagacgact | ccaacagtat | gttgttttg | 300 |
| gaaatcaaga | acatgacagc | cggggacacg | gccctctact | tctgcgccaa | agggccgggt | 360 |
| ggccatcttc | attattacta | tggtctagac | gtctggggcc | atgggacctc | ggtcaccgtc | 420 |
| tcgagcgcct | ccaccaaggg | cccatcggtc | ttccccctgg | caccctcctc | caagagcacc | 480 |
| tctgggggca | cagcggccct | gggctgcctg | gtcaaggact | acttccccga | accggtgacg | 540 |
| gtgtcgtgga | actcaggcgc | cctgaccagc | ggcgtgcaca | ccttcccggc | tgtcctacag | 600 |
| tcctcaggac | tctactccct | cagcagcgtg | gtgaccgtgc | cctccagcag | cttgggcacc | 660 |
| cagacctaca | tctgcaacgt | gaatcacaag | cccagcaaca | ccaaggtgga | caagagagtt | 720 |
| gagcccaaat | cttgtgacaa | aactcacaca | tgcccaccgt | gcccagcacc | tgaactcctg | 780 |
| gggggaccgt | cagtcttcct | cttccccca | aaacccaagg | acaccctcat | gatctcccgg | 840 |
| accccctgagg | tcacatgcgt | ggtggtggac | gtgagccacg | aagaccctga | ggtcaagttc | 900 |
| aactggtacg | tggacggcgt | ggaggtgcat | aatgccaaga | caaagccgcg | ggaggagcag | 960 |
| tacaacagca | cgtaccgtgt | ggtcagcgtc | ctcaccgtcc | tgcaccagga | ctggctgaat | 1020 |
| ggcaaggagt | acaagtgcaa | ggtctccaac | aaagccctcc | cagcccccat | cgagaaaacc | 1080 |
| atctccaaag | ccaaagggca | gccccgagaa | ccacaggtgt | acaccctgcc | cccatcccgg | 1140 |
| gaggagatga | ccaagaacca | ggtcagcctg | acctgcctgg | tcaaaggctt | ctatcccagc | 1200 |
| gacatcgccg | tggagtggga | gagcaatggg | cagccggaga | caactacaa | gaccacgcct | 1260 |
| cccgtgctgg | actccgacgg | ctccttcttc | ctctatagca | agctcaccgt | ggacaagagc | 1320 |
| aggtggcagc | aggggaacgt | cttctcatgc | tccgtgatgc | atgaggctct | gcacaaccac | 1380 |
| tacacgcaga | agagcctctc | cctgtctccg | ggtaaatga | | | 1419 |

<210> SEQ ID NO 2
<211> LENGTH: 453
<212> TYPE: PRT
<213> ORGANISM: Homo sapiens

<400> SEQUENCE: 2

Glu Val Gln Leu Leu Gln Ser Gly Gly Gly Leu Thr His Pro Gly Gly
1               5                   10                  15

Ser Leu Arg Leu Ser Cys Ala Ala Ser Gly Phe Pro Phe His Lys Tyr
            20                  25                  30

Thr Met Thr Trp Val Arg Gln Pro Pro Gly Lys Gly Leu Glu Trp Val
        35                  40                  45

```
Ser Ser Val Ser Gly Val Asn Gly Lys Thr Tyr Tyr Ser Pro Ser Val
     50                  55                  60

Arg Gly Arg Ala Ile Val Ser Arg Asp Asp Asn Ser Met Leu Phe
 65              70                  75                  80

Leu Glu Ile Lys Asn Met Thr Ala Gly Asp Thr Ala Leu Tyr Phe Cys
                 85                  90                  95

Ala Lys Gly Pro Gly Gly His Leu His Tyr Tyr Gly Leu Asp Val
             100             105                 110

Trp Gly His Gly Thr Ser Val Thr Val Ser Ser Ala Ser Thr Lys Gly
         115                 120             125

Pro Ser Val Phe Pro Leu Ala Pro Ser Ser Lys Ser Thr Ser Gly Gly
     130             135                 140

Thr Ala Ala Leu Gly Cys Leu Val Lys Asp Tyr Phe Pro Glu Pro Val
145             150                 155                 160

Thr Val Ser Trp Asn Ser Gly Ala Leu Thr Ser Gly Val His Thr Phe
                 165                 170                 175

Pro Ala Val Leu Gln Ser Ser Gly Leu Tyr Ser Leu Ser Ser Val Val
             180                 185                 190

Thr Val Pro Ser Ser Ser Leu Gly Thr Gln Thr Tyr Ile Cys Asn Val
         195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
             260                 265                 270

Ser His Glu Asp Pro Glu Val Lys Phe Asn Trp Tyr Val Asp Gly Val
         275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
             340                 345                 350

Gln Val Tyr Thr Leu Pro Pro Ser Arg Glu Glu Met Thr Lys Asn Gln
         355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
             420                 425                 430

Val Met His Glu Ala Leu His Asn His Tyr Thr Gln Lys Ser Leu Ser
         435                 440                 445

Leu Ser Pro Gly Lys
    450

<210> SEQ ID NO 3
```

<211> LENGTH: 123
<212> TYPE: PRT
<213> ORGANISM: Homo sapiens

<400> SEQUENCE: 3

Glu Val Gln Leu Leu Gln Ser Gly Gly Gly Leu Thr His Pro Gly Gly
1               5                   10                  15

Ser Leu Arg Leu Ser Cys Ala Ala Ser Gly Phe Pro Phe His Lys Tyr
            20                  25                  30

Thr Met Thr Trp Val Arg Gln Pro Pro Gly Lys Gly Leu Glu Trp Val
        35                  40                  45

Ser Ser Val Ser Gly Val Asn Gly Lys Thr Tyr Tyr Ser Pro Ser Val
    50                  55                  60

Arg Gly Arg Ala Ile Val Ser Arg Asp Asp Ser Asn Ser Met Leu Phe
65                  70                  75                  80

Leu Glu Ile Lys Asn Met Thr Ala Gly Asp Thr Ala Leu Tyr Phe Cys
                85                  90                  95

Ala Lys Gly Pro Gly Gly His Leu His Tyr Tyr Tyr Gly Leu Asp Val
            100                 105                 110

Trp Gly His Gly Thr Ser Val Thr Val Ser Ser
        115                 120

<210> SEQ ID NO 4
<211> LENGTH: 711
<212> TYPE: DNA
<213> ORGANISM: Homo sapiens
<220> FEATURE:
<221> NAME/KEY: misc_feature
<222> LOCATION: (4)..(5)
<223> OTHER INFORMATION: n is a, c, g, or t

<400> SEQUENCE: 4
atgnncatga gagtcctcgc tcagctcctg gggctcctgc tgctctgttt cccaggtgcc      60
agatgtgaca tccagatgac ccaatcccca tcctcactgt ctgcatctat ggagataga     120
gtcaccatct cttgtcgggc gagtcaggcc atcaacaatt atgttgcctg gtttcagcag    180
tctgcaggaa aagcccctaa gtctctcatc tatggtgcgt cgaatttgca acctggtgtc    240
ccaccaaggt tcagcggcag tgtatctggg acaaatttct ctctcaccat cgacggtctg    300
cagtccgaag actttgcaac ttatttctgt caaaattact tggttatcc cctcacttc    360
ggcggtggga ccacactgga gatcaaacgt acggtggctg caccatctgt cttcatcttc    420
ccgccatctg atgagcagtt gaaatctgga actgcctctg ttgtgtgcct gctgaataac    480
ttctatccca gagaggccaa agtacagtgg aaggtggata acgcctcca atcgggtaac    540
tcccaggaga gtgtcacaga gcaggacagc aaggacagca cctacagcct cagcagcacc    600
ctgacgctga gcaaagcaga ctacgagaaa cacaaagtct acgcctgcga agtcacccat    660
cagggcctga ctcgcccgt cacaaagagc ttcaacaggg gagagtgtta g              711

<210> SEQ ID NO 5
<211> LENGTH: 214
<212> TYPE: PRT
<213> ORGANISM: Homo sapiens

<400> SEQUENCE: 5

Asp Ile Gln Met Thr Gln Ser Pro Ser Ser Leu Ser Ala Ser Ile Gly
1               5                   10                  15

Asp Arg Val Thr Ile Ser Cys Arg Ala Ser Gln Ala Ile Asn Asn Tyr
            20                  25                  30

Val Ala Trp Phe Gln Gln Ser Ala Gly Lys Ala Pro Lys Ser Leu Ile
         35                  40                  45

Tyr Gly Ala Ser Asn Leu Gln Pro Gly Val Pro Pro Arg Phe Ser Gly
     50                  55                  60

Ser Val Ser Gly Thr Asn Phe Ser Leu Thr Ile Asp Gly Leu Gln Ser
 65                  70                  75                  80

Glu Asp Phe Ala Thr Tyr Phe Cys Gln Asn Tyr Phe Gly Tyr Pro Leu
                 85                  90                  95

Thr Phe Gly Gly Gly Thr Thr Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 6
<211> LENGTH: 107
<212> TYPE: PRT
<213> ORGANISM: Homo sapiens

<400> SEQUENCE: 6

Asp Ile Gln Met Thr Gln Ser Pro Ser Ser Leu Ser Ala Ser Ile Gly
 1               5                  10                  15

Asp Arg Val Thr Ile Ser Cys Arg Ala Ser Gln Ala Ile Asn Asn Tyr
             20                  25                  30

Val Ala Trp Phe Gln Gln Ser Ala Gly Lys Ala Pro Lys Ser Leu Ile
         35                  40                  45

Tyr Gly Ala Ser Asn Leu Gln Pro Gly Val Pro Pro Arg Phe Ser Gly
     50                  55                  60

Ser Val Ser Gly Thr Asn Phe Ser Leu Thr Ile Asp Gly Leu Gln Ser
 65                  70                  75                  80

Glu Asp Phe Ala Thr Tyr Phe Cys Gln Asn Tyr Phe Gly Tyr Pro Leu
                 85                  90                  95

Thr Phe Gly Gly Gly Thr Thr Leu Glu Ile Lys
            100                 105

<210> SEQ ID NO 7
<211> LENGTH: 369
<212> TYPE: DNA
<213> ORGANISM: Homo sapiens

<400> SEQUENCE: 7
gaggtccaat tattgcagtc ggggggggc ctgacacatc ctgggggtc cctgagactc      60 tcatgtgcgg cgtctggctt ccccttcac aaatatacca tgacttgggt ccgccagcct    120
ccagggaagg gcctggagtg gtctcaagt gttagtggtg tcaacggcaa gacatattat    180
agtccctccg tgagggggccg cgccatcgtc tccagagacg actccaacag tatgttgttt    240

```
ttggaaatca agaacatgac agccggggac acggccctct acttctgcgc caaagggccg      300
ggtggccatc ttcattatta ctatggtcta gacgtctggg gccatgggac ctcggtcacc      360
gtctcgagc                                                              369
```

<210> SEQ ID NO 8
<211> LENGTH: 9
<212> TYPE: PRT
<213> ORGANISM: Homo sapiens

<400> SEQUENCE: 8

```
Phe Pro Phe His Lys Tyr Thr Met Thr
1               5
```

<210> SEQ ID NO 9
<211> LENGTH: 16
<212> TYPE: PRT
<213> ORGANISM: Homo sapiens

<400> SEQUENCE: 9

```
Val Ser Gly Val Asn Gly Lys Thr Tyr Tyr Ser Pro Ser Val Arg Gly
1               5                   10                  15
```

<210> SEQ ID NO 10
<211> LENGTH: 14
<212> TYPE: PRT
<213> ORGANISM: Homo sapiens

<400> SEQUENCE: 10

```
Gly Pro Gly Gly His Leu His Tyr Tyr Tyr Gly Leu Asp Val
1               5                   10
```

<210> SEQ ID NO 11
<211> LENGTH: 10
<212> TYPE: PRT
<213> ORGANISM: Homo sapiens

<400> SEQUENCE: 11

```
Gly Phe Pro Phe His Lys Tyr Thr Met Thr
1               5                   10
```

<210> SEQ ID NO 12
<211> LENGTH: 9
<212> TYPE: PRT
<213> ORGANISM: Homo sapiens

<400> SEQUENCE: 12

```
Val Ser Gly Val Asn Gly Lys Thr Tyr
1               5
```

<210> SEQ ID NO 13
<211> LENGTH: 322
<212> TYPE: DNA
<213> ORGANISM: Homo sapiens

<400> SEQUENCE: 13

```
gacatccaga tgacccaatc cccatcctca ctgtctgcat ctattggaga tagagtcacc       60
atctcttgtc gggcgagtca ggccatcaac aattatgttg cctggtttca gcagtctgca     120
ggaaaagccc ctaagtctct catctatggt gcgtcgaatt tgcaacctgg tgtcccacca     180
aggttcagcg gcagtgtatc tgggacaaat ttctctctca ccatcgacgg tctgcagtcc     240
gaagactttg caacttattt ctgtcaaaat tactttggtt atcccctcac tttcggcggt     300
```

```
-continued gggaccacac tggagatcaa ac                                              322

<210> SEQ ID NO 14
<211> LENGTH: 11
<212> TYPE: PRT
<213> ORGANISM: Homo sapiens

<400> SEQUENCE: 14

Arg Ala Ser Gln Ala Ile Asn Asn Tyr Val Ala
1               5                   10

<210> SEQ ID NO 15
<211> LENGTH: 7
<212> TYPE: PRT
<213> ORGANISM: Homo sapiens

<400> SEQUENCE: 15

Gly Ala Ser Asn Leu Gln Pro
1               5

<210> SEQ ID NO 16
<211> LENGTH: 9
<212> TYPE: PRT
<213> ORGANISM: Homo sapiens

<400> SEQUENCE: 16

Gln Asn Tyr Phe Gly Tyr Pro Leu Thr
1               5
```

GRANULOCYTE-MACROPHAGE COLONY-STIMULATING FACTOR (GM-CSF) NEUTRALIZING ANTIBODIES

RELATED APPLICATIONS

This application claims the benefit of provisional applications U.S. Ser. No. 61/172,120, filed Apr. 23, 2009 and U.S. Ser. No. 61/234,946, filed Aug. 18, 2009, the contents of which are each herein incorporated by reference in their entirety.

INCORPORATION OF SEQUENCE LISTING

The contents of the text file named "37418-508001USSeqList.txt," which was created on Jun. 11, 2010 and is 14 KB in size, are hereby incorporated by reference in their entirety.

FIELD OF THE INVENTION

The invention relates generally to the fields of immunology and medicine. Specifically, the invention relates to compositions containing the GM-CSF neutralizing human monoclonal antibody 1783J22, as well as methods of making and using this antibody.

BACKGROUND OF THE INVENTION

Much of the control of blood-cell formation is mediated by a group of interacting glycoproteins termed colony stimulating factors (CSFs). Granulocyte macrophage-colony stimulating factor ("GM-CSF"), a soluble secreted glycoprotein, is a potent immunomodulatory cytokine known to facilitate development and prolongation of both humoral and cellular mediated immunity.

GM-CSF also plays a role in the genesis and progression of a plurality of human diseases, such as cancer, inflammatory and autoimmune diseases, and degenerative diseases.

Therefore a long-felt need exists in the field for therapeutic compositions and methods capable of antagonizing or inhibiting the activity of GM-CSF. Despite multiple attempts to generate antibodies specific for GM-CSF, for instance, through the creation of polyclonal and monoclonal antibodies, no one has succeeded in creating a therapeutically-effective human antibody composition that inhibits the activity of GM-CSF. The invention provides compositions and methods for inhibiting, or neutralizing, the activity of GM-CSF, and, therefore, succeeds in addressing the long-felt need in the art.

SUMMARY OF THE INVENTION

The invention provides an isolated human monoclonal antibody that specifically binds and neutralizes GM-CSF. Anti-GM-CSF monoclonal antibodies of the invention are obtained by a process including (a) screening memory B cell cultures from a donor Peripheral Blood Mononuclear Cell (PBMC) sample for neutralization activity against GM-CSF and (b) rescuing the monoclonal antibody from a memory B cell culture that neutralizes GM-CSF. Optionally, the method further includes culturing an immortalized B cell clone expressing an antibody and isolating antibodies from said B cell.

The invention provides an isolated fully human monoclonal antibody, wherein the monoclonal antibody has the following characteristics: (a) specifically binds to an epitope of a GM-CSF protein; and (b) neutralizes GM-CSF bioactivity in vitro. In some embodiments, this antibody is isolated from a B cell from a human donor. In some embodiments, wherein this antibody is operably-linked to a therapeutic agent or a detectable label.

In some embodiments, the epitope is linear, non-linear, or discontinuous. For example, the epitope is a linear amino acid polypeptide or a folded polypeptide that reflects that native configuration of a GM-CSF protein. Alternatively, the epitope is a conformational or discontinuous epitope that is recognizable by the antibody only when the GM-CSF antibody is folded, arranged as a homodimer, or a discontinuous portion of the GM-CSF amino acid sequence is maintained in a particular three-dimensional form using an accessory structure to mimic the native surface (for instance, by use of a CLIP). The epitope is an immunogenic polypeptide or a glycopeptide that is bound an antibody of the invention.

In a preferred embodiment, the antibody is 1783J22. Alternatively, or in addition, the antibody is a sister clone of the 1783J22 antibody. For instance, the sister clone contains a distinct heavy or light chain nucleic acid sequence that results in a heavy or light chain amino acid sequence that is identical to the 1783J22 antibody. In other aspects of the invention, the amino acid sequences of the heavy and light chains of the sister clones are 70%, 75%, 80%, 85%, 90%, 95%, 100% or any percentage in between identical to the amino acid sequences of the heavy and light chains of the 1783J22 antibody.

The invention provides an antibody that binds the same epitope as 1783J22.

The invention provides an isolated fully human monoclonal anti-GM-CSF antibody or fragment thereof, wherein said antibody includes a variable heavy chain ($V_H$) region containing a CDR1 and a CDR2, wherein said region is encoded by a human IGHV3-23 $V_H$ germline sequence, or a nucleic acid sequence that is homologous to the IGHV3-23 $V_H$ germline gene sequence. In some embodiments, the nucleic acid sequence that is homologous to the IGHV3-23 $V_H$ germline sequence is at least 90% homologous to the IGHV3-23 $V_H$ germline sequence. This antibody further includes a variable light chain ($V_L$) region encoded by a human IGKV1-16 $V_L$ germline gene sequence, or a nucleic acid sequence that is homologous to the said $V_L$ germline gene sequence. In some embodiments, the nucleic acid sequence that is homologous to the IGKV1-16 $V_L$ germline sequence is at least 90% homologous to the said IGKV1-16 $V_L$ germline sequence.

The invention provides an isolated anti-GM-CSF antibody, wherein the antibody has a heavy chain with three CDRs including an amino acid sequence selected from the group consisting of the amino acid sequences of FPFHKYTMT (SEQ ID NO: 8), VSGVNGKTYYSPSVRG (SEQ ID NO: 9), and GPGGHLHYYYGLDV (SEQ ID NO: 10), and a light chain with three CDRs that include an amino acid sequence selected from the group consisting of the amino acid sequences of RASQAINNYVA (SEQ ID NO: 14), GASNLQP (SEQ ID NO: 15), and QNYFGYPLT (SEQ ID NO: 16).

The invention also provides an isolated anti-GM-CSF antibody, wherein the antibody has a heavy chain with three CDRs including an amino acid sequence selected from the group consisting of the amino acid sequences of GFPFHKYTMT (SEQ ID NO: 11), VSGVNGKTY (SEQ ID NO: 12), and GPGGHLHYYYGLDV (SEQ ID NO: 10), and a light chain with three CDRs that include an amino acid sequence selected from the group consisting of the amino acid sequences of RASQAINNYVA (SEQ ID NO: 14), GASNLQP (SEQ ID NO: 15), and QNYFGYPLT (SEQ ID NO: 16).

The invention provides an isolated anti-GM-CSF antibody, wherein the antibody has a heavy chain with three CDRs including an amino acid sequence selected from the group consisting of the amino acid sequences of FPFHKYTMT (SEQ ID NO: 8), VSGVNGKTYYSPSVRG (SEQ ID NO: 9), and GPGGHLHYYYGLDV (SEQ ID NO: 10), GFPFHKYTMT (SEQ ID NO: 11), VSGVNGKTY (SEQ ID NO: 12), wherein said antibody binds GM-CSF.

The invention provides an isolated anti-GM-CSF antibody, wherein the antibody has a light chain with three CDRs including an amino acid sequence selected from the group consisting of the amino acid sequences of RASQAINNYVA (SEQ ID NO: 14), GASNLQP (SEQ ID NO: 15), and QNYFGYPLT (SEQ ID NO: 16), wherein said antibody binds GM-CSF.

The invention provides an isolated anti-GM-CSF antibody, wherein the antibody includes a $V_H$ CDR1 region containing the amino acid sequence of FPFHKYTMT (SEQ ID NO: 8); a $V_H$ CDR2 region containing the amino acid sequence of VSGVNGKTYYSPSVRG (SEQ ID NO: 9); a $V_H$ CDR3 region containing the amino acid sequence of GPGGHLHYYYGLDV (SEQ ID NO: 10); a $V_L$ CDR1 region containing the amino acid sequence of RASQAINNYVA (SEQ ID NO: 14); a $V_L$ CDR2 region containing the amino acid sequence of GASNLQP (SEQ ID NO: 15); and a $V_L$ CDR3 region containing the amino acid sequence of QNYFGYPLT (SEQ ID NO: 16).

The invention provides an isolated anti-GM-CSF antibody, wherein the antibody includes a $V_H$ CDR1 region containing the amino acid sequence of GFPFHKYTMT (SEQ ID NO: 11); a $V_H$ CDR2 region containing the amino acid sequence of VSGVNGKTY (SEQ ID NO: 12); a $V_H$ CDR3 region containing the amino acid sequence of GPGGHLHYYYGLDV (SEQ ID NO: 10); a $V_L$ CDR1 region containing the amino acid sequence of RASQAINNYVA (SEQ ID NO: 14); a $V_L$ CDR2 region containing the amino acid sequence of GASNLQP (SEQ ID NO: 15); and a $V_L$ CDR3 region containing the amino acid sequence of QNYFGYPLT (SEQ ID NO: 16).

The invention provides an isolated anti-GM-CSF antibody or fragment thereof, wherein the antibody includes: (a) a $V_H$ CDR1 region containing the amino acid sequence of FPFHKYTMT (SEQ ID NO: 8) or GFPFHKYTMT (SEQ ID NO: 11); (b) a $V_H$ CDR2 region containing the amino acid sequence of VSGVNGKTYYSPSVRG (SEQ ID NO: 9) or VSGVNGKTY (SEQ ID NO: 12); and (c) a $V_H$ CDR3 region containing the amino acid sequence of GPGGHLHYYYGLDV (SEQ ID NO: 10), wherein the antibody binds GM-CSF. In some embodiments, this antibody further includes: (a) a $V_L$ CDR1 region containing the amino acid sequence of RASQAINNYVA (SEQ ID NO: 14); (b) a $V_L$ CDR2 region containing the amino acid sequence of GASNLQP (SEQ ID NO: 15); and (c) a $V_L$ CDR3 region containing the amino acid sequence of QNYFGYPLT (SEQ ID NO: 16).

The invention provides an isolated fully human monoclonal anti-GM-CSF antibody including a heavy chain sequence containing the amino acid sequence SEQ ID NO: 2 and a light chain sequence containing amino acid sequence SEQ ID NO: 5.

The invention provides a composition including an antibody described herein and a pharmaceutically acceptable carrier. Preferably, the antibody is an isolated fully human monoclonal antibody with the following characteristics: (a) specifically binds to an epitope of a GM-CSF protein; and (b) neutralizes GM-CSF bioactivity in vitro. In some embodiments, this antibody is isolated from a B cell from a human donor. In some embodiments of this composition, the antibody is operably-linked to a therapeutic agent or a detectable label. In some embodiments, the composition further includes a second anti-GM-CSF antibody. In some embodiments, an antibody or composition of the invention is administered in combination with other therapies. In some embodiments, an antibody or composition of the invention is manufactured for use as an adjuvant formulation.

The invention provides a fragment of an antibody described herein. Preferably, the antibody is an isolated fully human monoclonal antibody with the following characteristics: (a) specifically binds to an epitope of a GM-CSF protein; and (b) neutralizes GM-CSF bioactivity in vitro. In some embodiments, this antibody is isolated from a B cell from a human donor. In some embodiments, the fragment is selected from the group consisting of Fab, Fab', F(ab')$_2$, Fv, single chain Fv, diabody and domain antibody (dAb) fragments.

The invention provides a vector including the nucleic acid sequence of SEQ ID NOs: 1 or 4. Alternatively, or in addition, the vector includes a nucleic acid encoding a heavy or light chain of an antibody described herein. In other aspects, the vector includes a nucleic acid encoding a heavy or light chain of an anti-GM-CSF antibody administered simultaneously or sequentially with respect to an antibody described herein. The invention provides a cell including this vector.

The invention further provides a B cell clone expressing an antibody described herein. Preferably, the antibody is an isolated fully human monoclonal antibody with the following characteristics: (a) specifically binds to an epitope of a GM-CSF protein; and (b) neutralizes GM-CSF bioactivity in vitro. In some embodiments, this antibody is isolated from a B cell from a human donor. In some embodiments, the antibody is recombinant.

The invention provides a method of stimulating an immune response in a subject, comprising administering to a patient a composition of the invention. In some embodiments, the method further comprises administering a second anti-GM-CSF antibody. In one aspect, the second antibody is administered simultaneously or sequentially with respect to the composition.

The invention provides a method for the treatment or prevention of a GM-CSF-mediated disease in a subject including administering to the subject a composition of the invention. In some embodiments of this method, an antibody of the composition binds to GM-CSF and inhibits the biological activity of GM-CSF in the patient. In some embodiments, the CM-CSF mediated disease is an infectious disease, an inflammatory disease, an autoimmune disorder, Alzheimer's Disease, or cancer.

In a specific embodiment, the GM-CSF-mediated disease is Alzheimer's disease (AD) or vascular dementia (VAD). Administration of a composition of the invention to a subject with Alzheimer's disease (AD) or vascular dementia (VAD) down-regulates expression, translation, or activity of autologous beta-amyloid (Aβ) protein or autologous amyloid precursor protein (APP), thereby treating or preventing the GM-CSF-mediated disease.

In a specific embodiment, the GM-CSF-mediated disease is an inflammatory disease. Preferably, the inflammatory disease is selected from the group consisting of asthma, acute inflammation, chronic inflammation, type I diabetes, type II diabetes and all of the related pathologies, rheumatoid arthritis, autoimmune disease, inflammatory renal disease, inflammatory lung disorders such as asthma and chronic obstructive pulmonary disease (COPD), multiple sclerosis, and autoimmune encephalomyelitis.

In another specific embodiment, the GM-CSF-mediated disease is cancer. Although all forms are cancer are contemplated, in preferred embodiments of this method, the cancer is selected from the group consisting of colon cancer, lung cancer, breast cancer, pancreatic cancer, leukemia, and juvenile myelomonocytic leukemia. Some embodiments of this method further include administering a second anti-GM-CSF antibody. The second antibody is administered simultaneously or sequentially with respect to the composition.

The invention provides a method of inhibiting the biological activity of human GM-CSF in a patient with an infectious disease comprising administering to the patient a composition of the invention. In some embodiments of this method, the infectious disease is selected from the group consisting of sepsis, severe acute respiratory syndrome (SARS; caused by SARS-associated coronavirus), hepatitis type B or type C, influenza, varicella, adenovirus, herpes simplex virus type I or type II, rinderpest, rhinovirus, echovirus, rotavirus, respiratory syncytial virus, papilloma virus, papova virus, cytomegalovirus, echinovirus, arbovirus, hantavirus, coxsachie virus, mumps virus, measles virus, rubella virus, polio virus, human immunodeficiency virus (HIV) type I or type II, Meningitis, Septic arthritis, Peritonitis, Pneumonia, Epiglottitis, *E. coli*, Hemolytic uremic syndrome, thrombocytopenia, to, Ebola, *Staphylococcus* A-E, Plasmodium, Malaria, Dengue, hemorrhagic fever, Leishmaniasis, Leprosy, Toxic shock syndrome, *Streptococcal myositis*, Gas gangrene, *Mycobacterium*, Pneumocystis, Pelvic inflammatory disease, Orchitis/epidydimitis, *Legionella*, Lyme disease Influenza A, Epstein-Barr Virus, Viral associated hemiaphagocytic syndrome, viral encephalitis, aseptic meningitis, mycoplasma, *Neisseria, Legionella, Rickettsia*, and *Chlamydia*.

The invention further provides a vaccine including an epitope of an antibody of the invention. Preferably, the antibody is an isolated fully human monoclonal antibody with the following characteristics: (a) specifically binds to an epitope of a GM-CSF protein; and (b) neutralizes GM-CSF bioactivity in vitro. In some embodiments, this antibody is isolated from a B cell from a human donor.

The invention provides a vaccine including an epitope of the 1783J22 antibody.

The invention provides a therapeutic kit including an antibody of the invention. Preferably, the antibody is an isolated fully human monoclonal antibody with the following characteristics: (a) specifically binds to an epitope of a GM-CSF protein; and (b) neutralizes GM-CSF bioactivity in vitro. In some embodiments, this antibody is isolated from a B cell from a human donor.

The invention provides a therapeutic kit including a composition of the invention.

The invention provides a prophylactic kit including a vaccine containing an epitope of an antibody of the invention.

The invention provides a prophylactic kit including the vaccine containing an epitope of the 1783J22 antibody.

The invention provides a method for inhibiting a GM-CSF activity in a rabbit, the method including: (a) administering to a rabbit a monoclonal antibody according to the invention; and (b) determining the inhibition of a GM-CSF induced activity in the rabbit. In one embodiment, the method further includes: (c) determining the binding of GM-CSF to the monoclonal antibody in the rabbit.

In some aspects, the GM-CSF induced activity is a cell proliferative activity, or stimulation of early- and late-phase granulocyte and macrophage progenitor cells, or activation of mature neutrophils and macrophages; or enhanced peripheral anti-infection activity; or activation of mature neutrophils, macrophages, eosinophils and basophils; or stimulation of stem cells to produce granulocytes (neutrophils, eosinophils, and basophils) and monocytes.

Other features and advantages of the invention will be apparent from and are encompassed by the following detailed description and claims.

Figure 7:
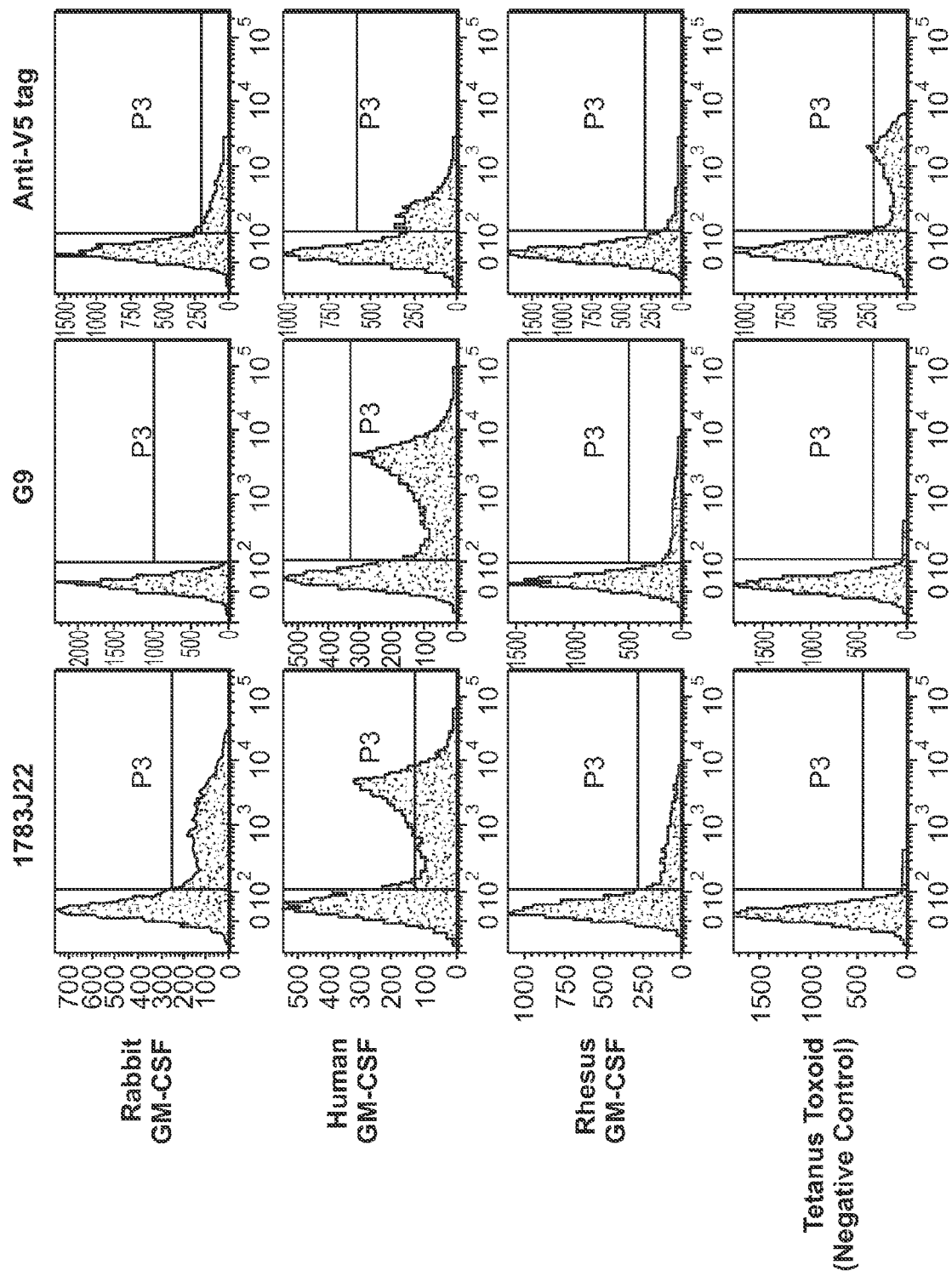

FIG. 7 is a series of graphs depicting the potential cross-reactivity of the 1782J22 antibody, the control antibody G9, and the anti-V5 tag alone with rabbit, human, and Rhesus GM-CSF. The 1782J22 antibody bound to rabbit, human and rhesus GM-CSF, whereas the G9 control antibody bound to only human and rhesus GM-CSF, but not rabbit GM-CSF.

Figure 8:
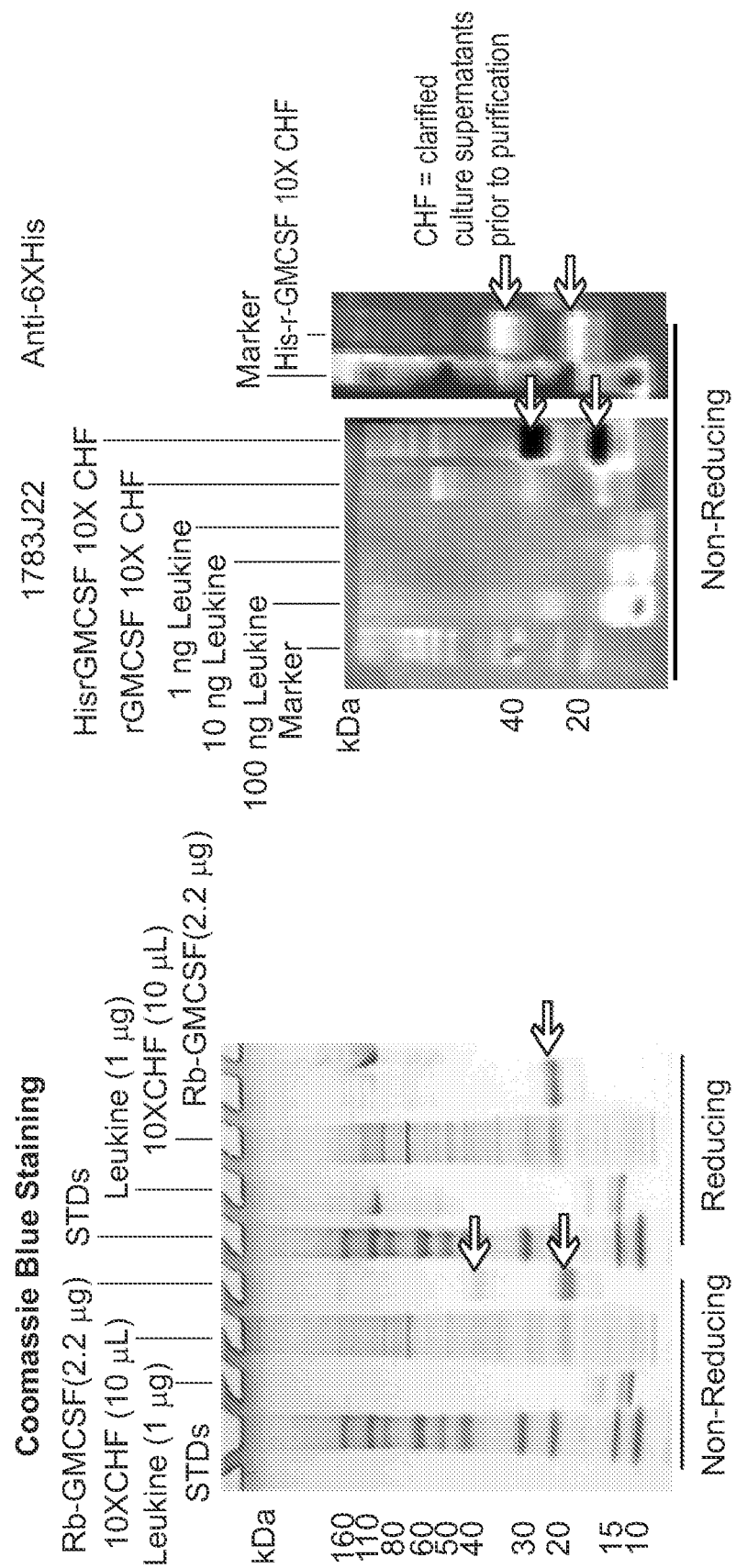

FIG. 8 is a series of photographs of Western Blot assays depicting the cross-reactivity of the 1783J22 antibody with rabbit GM-CSF, when secreted as a His-tagged protein from HEK293 transfectants.

Figure 9:
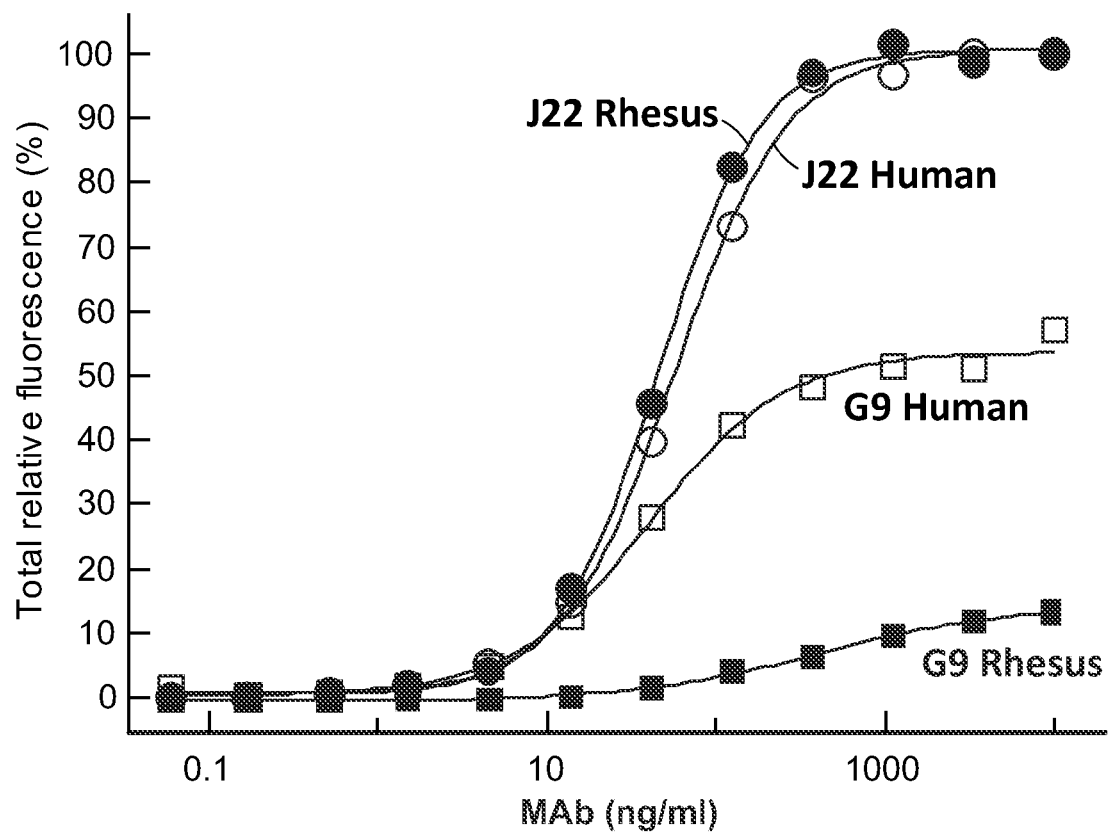

FIG. 9 is a graph depicting the human and rhesus GM-CSF binding reactivity of the 1783J22 and G9 antibodies, measured as the percent total relative fluorescence (%) as a function of monoclonal antibody (MAb) concentration (provided as nanograms per milliliter, or ng/ml). The results indicated that 1783J22 binds equally well to Rhesus GM-CSF and Human GM-CSF, when these proteins are expressed on the surface of HEK293 cells.

DETAILED DESCRIPTION OF THE INVENTION

GM-CSF

Blood cells in circulation are constantly replaced by newly developed cells. Replacement blood cells are formed in a process termed hematopoiesis which involves the production of at least eight mature blood cell types within two major lineages: (1) the myeloid lineage which includes red blood cells (erythrocytes), macrophages (monocytes), eosinophilic granulocytes, megakaryocytes (platelets), neutrophilic granulocytes, basophilic granulocytes (mast cells); and (2) the lymphoid lineage which includes T lymphocytes and B lymphocytes (Burgess and Nicola, Growth Factors and Stem Cells (Academic Press, New York, 1983)). Much of the control of blood-cell formation is mediated by a group of interacting glycoproteins termed colony stimulating factors (CSFs). The role of CSFs in hematopoiesis is the subject of many reviews, and is of great interest to clinical investigators who must treat blood diseases or deficiencies; e.g. Metcalf, The Hemopoietic Colony Stimulating Factors (Elsevier, N.Y., 1984); Clark and Kamen, Science, Vol. 236, pgs. 1229-1237 (1987); Sachs, Science, Vol. 238, pgs. 1374-1379 (1987); Dexter et al., eds., Colony Stimulating Factors (Dekker, N.Y., 1990); and Morstyn et al., Cancer Investigation, Vol. 7, pgs. 443-456 (1989).

Granulocyte macrophage-colony stimulating factor ("GM-CSF"), a soluble secreted glycoprotein, is a potent immunomodulatory cytokine known to facilitate development and prolongation of both humoral and cellular mediated immunity. GM-CSF was originally discovered as a protein with the capacity to generate both granulocyte and macrophage colonies from precursor cells in mouse bone marrow, and was accordingly named (Burgess et al. (1980) Blood 56:947-58.). GM-CSF stimulates stem cells to produce granulocytes (neutrophils, eosinophils, and basophils) and monocytes. Activities of GM-CSF include activation and enhanced maturation of antigen presenting cells, increasing the expression of MHC class II antigens, activation of mature granulocytes, macrophages and monocytes, and proliferation and differentiation of hematopoietic progenitor cells. The functions of GM-CSF are mediated by binding to CD116, the granulocyte-macrophage colony stimulating factor receptor, also known as colony stimulating factor 2 receptor alpha that binds GM-CSF with low affinity. The GM-CSF receptors are found on myeloid progenitors and mature myeloid cells including neutrophils, eosinophils, mononuclear phagocytes, and monocytes. In addition, GM-CSF receptor subunits have been shown to be present in normal, non-hematopoietic tissues such as human placenta, endothelium, and oligodendrocytes of the central nervous system.

Human granulocyte macrophage colony-stimulating factor (GM-CSF) is a glycoprotein with a molecular weight of about 23,000 daltons. The cDNA sequence and the expression of the glycoprotein in mammalian cells have already been disclosed (G. G. Wong et al., Science 228 (1985), 810-815, D. Metcalf, Science 229 (1985), 16-22). The active form of the protein is found extracellularly as a homodimer. The gene has been localized to a cluster of related genes at chromosome region 5q31, which is known to be associated with interstitial deletions in the 5q-syndrome and acute myelogenous leukemia. GM-CSF is also known as molgramostim or, when the protein is expressed in yeast cells, sargramostim (LEUKINE®; Berlex Laboratories).

GM-CSF stimulates the production of white blood cells. GM-CSF holds great promise as a biopharmaceutical for use in association with cancer treatment to aid in the restoration of white blood cells. Naturally occurring GM-CSF is a glycoprotein containing 127 amino acids and two disulphide bonds. GM-CSF is present in only trace quantities in the natural human source. GM-CSF holds great promise as a biopharmaceutical for use in association with cancer treatment to aid in the restoration of white blood cells. The diverse immunomodulatory activities of GM-CSF have made it an attractive investigational cytokine for use as a vaccine adjuvant for improving the immune response to vaccines, including those used for the treatment of cancer and HIV.

GM-CSF plays a role in the genesis and progression of leukemias, such as juvenile myelomonocytic leukemia (JMML). (Emanuel P D (2004) Curr. Hematol. Rep. 3:203-209). JMML is characterized by disruption of normal hematopoiesis resulting in excessive, inappropriate proliferation of immature myeloid cells in the bone marrow. Patients with JMML are hypersensitive to GM-CSF and exhibit pathologic features similar to those in transgenic mice that over-express GM-CSF (Lang et al. (1987) 51:675-86). Furthermore, GM-CSF has been shown to promote JMML cell growth and survival (Emanuel et al (1991) Blood 77:925-9).

There is recent evidence for a key role for GM-CSF in inflammatory and autoimmune diseases, therefore making it worthy of consideration for targeting. Such evidence includes disease exacerbation following its administration and amelioration of disease in animal models by GM-CSF gene targeting or by anti-GM-CSF antibody blockade. Hamilton J A, Trends in Immunology 23(8): 403-408 (2002). GM-CSF has been shown to play a role in potentiating the function of mature macrophages and granulocytes (Handman and Burgess (1979) J. Immunol. 122:1134-1137; Hamilton et al. (1980) J. Cell Physiol. 103:435-445; Gamble et al. (1985) Proc. Natl. Acad. Sci. USA 82:8667-8671), suggesting a role for GM-CSF in inflammatory responses (Hamilton et al. (1980) J. Cell Physiol. 103:435-445). In a clinical setting, administration of GM-CSF into peritoneal dialysis patients resulted in a marked recruitment of macrophages (Selgas et al., 1996, Kidney Int. 50:2070-2078).

GM-CSF may play a role in constitutional predisposition towards a multitude of human inflammatory pathologies, such as rheumatoid arthritis, autoimmune pathologies, inflammatory renal disease and inflammatory lung disorders such as asthma and chronic obstructive pulmonary disease (COPD). Patients with rheumatoid arthritis treated with GM-CSF had their arthritis was exacerbated (Hazenberg et al., 1991, Blood 74:2769-2770). Following cancer chemotherapy, GM-CSF treatment made rheumatoid arthritis worse (de Vries et al., (1991) J. Immunol. 163: 4985-4993).

GM-CSF is a lymphokine (stimulator of the immune system) that exhibits a broad spectrum of immune cell stimulation as described in Burgess and Metcalf, Blood, 56:947 (1980) and Metcalf, Blood 67:257 (1986). GM-CSF has been shown to increase the leukocyte count in patients with acquired immunodeficiency syndrome (Brandt et al., N. Engl. J. Med., 318:869 (1988)) and people suffering from chemotherapy-induced myelosuppression (Antman et al., New Engl. J. Med., 319:593 (1988)). It has been suggested that various colony stimulating factors alone or in combination with erythropoietin and/or an antiviral agent and/or interleukin-2 (IL-2) may be useful for the treatment of patients suffering from AIDS.

In addition to its ability to stimulate proliferation of hematopoietic precursor cells, GM-CSF is also able to stimulate a number of functional aspects of mature granulocytes and macrophages. These effects include synthesis of biologically active molecules such as prostaglandin E (Hancock et al., J. Immunol., 140:3021 (1988) and Kurland et al., Proc. Natl. Acad. Sci. USA, 76:2326 (1979)); increased phagocytic activity (Weisbart et al., Nature, 332:647 (1988)); expression and/or affinity of various membrane markers such as the IL-2 receptor (Hancock et al., J. Immunol., 140:3021 (1988)) and receptors on neutrophils which elicit the production of superoxide anions (Atkinson et al., Immunology, 64:519 (1988)); and the regulation of enzyme activity such as the stimulation of guanylate cyclase and the inhibition of adenylate cyclase (Coffey et al., J. Immunol., 140:2695 (1988)).

There may be a link between multiple sclerosis and GM-CSF (McQualter et al. (2001) J. Exp. Med., 194:873-881). In an experimental model of autoimmune encephalomyelitis, a model for multiple sclerosis, GM-CSF was found to be involved in the autoimmune-mediated demyelination.

It has been shown that GM-CSF can "prime" cells to respond in a synergistic manner to a second stimulus, such as LPS or interferon-gamma (Hart et al., 1988, J. Immunol. 141:1516-1521).

Aberrant expression of GM-CSF is associated with disease of the lung in humans. Up-regulation of GM-CSF in the lung by minor irritants, endotoxins or infections predisposes towards TH2 immune deviation and asthma (Eisenbarth et al. (2002) J. Exp. Med. 196:1645-1651). A role for GM-CSF in asthma has been suggested. The use of neutralizing antibodies in a mouse model of asthma has demonstrated the ability to suppress asthmatic phenotypes (Yamashita (2002) Cell Immunol. 219:92). Allergens, alone or in combination with other factors, can spontaneously induce GM-CSF production in the airway thus present a compelling etiological argument for the role of GM-CSF in allergic sensitization. (Gajewska (2003) Curr Drug Targets Inflamm Allergy 2:279).

Adult human pulmonary alveolar proteinosis (PAP) is a rare disease characterized by the accumulation of phospholipids and surfactant proteins in the alveoli. GM-CSF null mice have impaired surfactant clearance that leads to murine pulmonary alveolar proteinosis (PAP), which closely mimics the human condition as described herein. Moreover, the PAP phenotype can be corrected by lung-specific delivery of the GM-CSF gene (Zsengaller et al. (1998) Hum. Gene Ther. 9:2101-2109). Patients with PAP have been shown to have circulating, neutralizing antibodies to GM-CSF, thereby implicating this cytokine as causative of the disease. (Latzin P., et al., Thorax. (2005) 60(1):39-44).

GM-CSF has been used for lowering levels of lipoprotein cholesterol, serum cholesterol and other lipids. (U.S. Pat. No. 5,019,381). Profound decreases in serum cholesterol concentrations were observed during GM-CSF therapy in patients with aplastic anemia. (Nimer S D, et al. JAMA 260(22): 3297-3300 (1988).

Local and systemic GM-CSF release in patients with Alzheimer's disease (AD) and vascular dementia (VAD) has been reported. (Tarkowski, E. et al., Acta Neurol Scand. (2001) 103(3):166-174.) One of the hallmarks of AD is the accumulation of amyloid beta plaques in the brain parenchyma. Neutralization of GM-CSF has been shown to decrease amyloid-beta and suppress microglial activity in mouse models of AD. (Manczak M. et al., Hum. Mol. Genet. (2009, Jul. 19) Epub.) GM-CSF neutralizing antibodies have been shown to mitigate CD40L induced production of amyloid beta. (Volmar C H, et al., Cytokine (2008) 42(3):336-344.)

GM-CSF inhibits osteoclast differentiation by converting precursors into dendritic cells (see, e.g., Khapli et al., J. Immunol. 171:142-151, 2003; Miyamoto et al., Blood 98:2544-2554, 2001; Myint et al., Am. J. Pathol. 154:553-566, 1999; Shuto et al., Endocrinology 134:1121-1126, 1994; and Kim et al., J. Biol. Chem. 280:16163-16169, 2005). There have also been reports that under certain conditions, GM-CSF may promote the formation of osteoclastic cells in vitro (e.g., U.S. Pat. No. 6,331,562) and that colony stimulating factors may be therapeutic targets in particular circumstances (U.S. Patent Application Publication No. 20020141994).

Therefore it is desirable to antagonize the activity of GM-CSF by developing an antibody to the cytokine. Such a compound may be a valuable human therapeutic. Several polyclonal and monoclonal antibodies have been generated to recombinant GM-CSF. For example, Beffy et al. ((1994), Hybridoma 13:457-468), generated polyclonal antibodies to recombinant human GM-CSF in New Zealand White rabbits and monoclonal antibodies in Balb/c mice. These rabbit and some of the murine monoclonal antibodies were capable of neutralizing the activity of GM-CSF in an in vitro cell proliferation assay with MO7c cells. Three murine antibodies to human GM-CSF were generated by Dempsey et al. (1990, Hybridoma 9, 545-558) that neutralized GM-CSF in an in vitro assay system. While these antibodies are useful reagents for the detection of GM-CSF in human serum as well as for in vitro assays to inhibit GM-CSF signaling, they have little value as therapeutics due to the fact that they are derived from either a murine or rabbit system. Attempts have been made to generate chimeric antibodies from murine counterparts by subcloning the variable domain from the murine anti-GM-CSF antibody into a human backbone. (WO 03/068924 A2). A human monoclonal antibody, i.e. G9, that specifically binds to GM-CSF has been reported. (Li J, et al, 2006, PNAS, 103:3557-62; WO 2007/092939); US Pat. App. Pub. No. 20080292641A1)

There is a need for therapeutic human antibodies for the treatment of inflammation associated with infectious diseases, inflammatory diseases, autoimmune disorders, and other diseases such as cancer associated with GM-CSF. It is further desired that such antibodies would elicit immune effector functions, as well as be well-tolerated in human patients. There is therefore a need for the efficient identification and production of neutralizing antibodies effective against GM-CSF as well as the elucidation of the target and antigenic determinants to which such antibodies bind. The invention addresses these and other long felt needs.

Anti-GM-CSF Antibodies

The anti-GM-CSF antibodies of the present invention are isolated by an In-Situ Therapeutic Antibody Rescue method (I-STAR™; Theraclone Sciences, Seattle Wash.) which involves discovery and synthesis of human therapeutic monoclonal antibodies directly from human memory B cells. B cells are screened for neutralization activity prior to rescue of antibodies. Novel neutralizing antibodies are obtained by emphasizing neutralization as the initial screen.

Peripheral Blood Mononuclear Cells (PBMCs) are obtained from a human donor selected for GM-CSF neutralizing activity in the plasma. Memory B cells are isolated and B cell culture supernatants are subjected to a primary screen of neutralization assay in a high throughput format. Optionally, GM-CSF antigen binding assays using ELISA or like methods are also used as a screen. B cell lysates corresponding to supernatants exhibiting neutralizing activity are selected for rescue of monoclonal antibodies by standard recombinant methods.

In one embodiment, the recombinant rescue of the monoclonal antibodies involves use of a B cell culture system as described in Weitcamp J-H et al., *J. Immunol.* 171:4680-4688 (2003). Any other method for rescue of single B cells clones known in the art also may be employed such as EBV immortalization of B cells (Traggiai E., et al., *Nat. Med.* 10(8):871-875 (2004)), electrofusion (Buchacher, A., et al., 1994. *AIDS Res. Hum. Retroviruses* 10:359-369), and B cell hybridoma (Karpas A. et al., *Proc. Natl. Acad. Sci. USA* 98:1799-1804 (2001).

In some embodiments, monoclonal antibodies were rescued from the B cell cultures using variable chain gene-specific RT-PCR, and transfectant with combinations of H and L chain clones were screened again for neutralization and GM-CSF antigen binding activities. mAbs with neutralization properties were selected for further characterization.

A human monoclonal antibody, 1783J22, identified according to these methods is disclosed herein. The antibody has been shown to neutralize GM-CSF in vitro.

Figure 2:
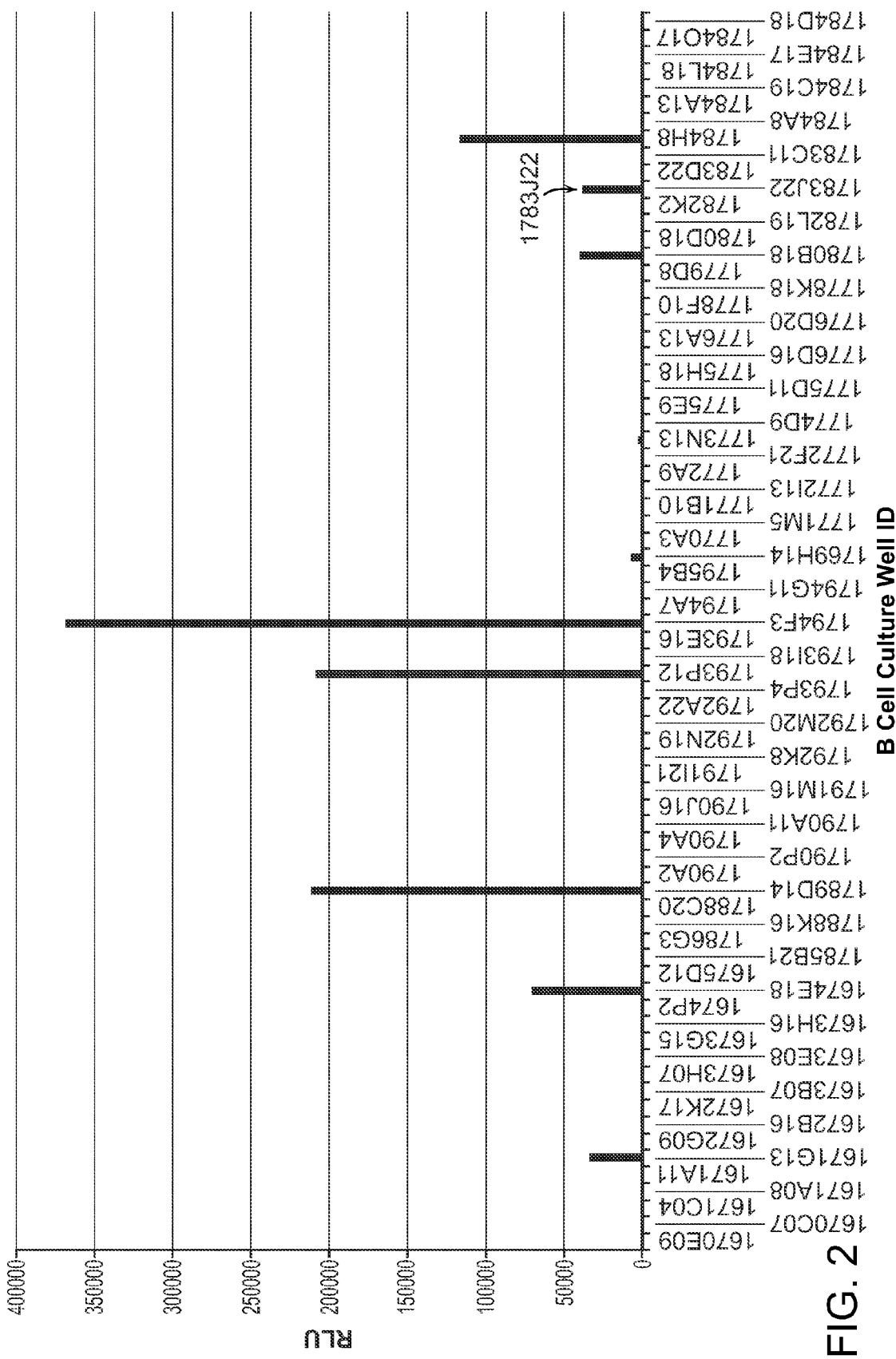
FIG. 2 is a graph depicting the binding activity of 1783J22 to human GM-CSF as the amount of relative luminescence units (RLU) per B Cell Culture Well Identification (ID). The assay confirms that 1783J22 binds human GM-CSF.

The monoclonal antibody 1783J22 exhibits strong binding to human GM-CSF among a panel of B cell supernatants, most of which have no GM-CSF neutralizing activity, as shown in FIG. 2 and Example 2 below. 1783J22 also exhibits neutralization activity in TF1 proliferation assays as shown in Examples 4 and 5 and FIGS. 4B and 5 below.

The binding and neutralization characteristics of 1783J22 were compared to those of a known human monoclonal GM-CSF antibody, G9. (Li J, et al, 2006, PNAS, 103:3557-62; WO 2007/092939); US Pat. App. Pub. No. 20080292641A1). 1783J22 displays a higher potency for neutralizing GM-CSF derived from yeast as compared to G9. (See FIG. 5 and Example 5).

1783J22 and G9 bind to different epitopes on GM-CSF. 1783J22 Fab does not compete with G9 whole antibody binding to human GM-CSF and G9 Fab does not compete with 1783J22 whole antibody binding to human GM-CSF. (See FIG. 6 and Example 6). It was also observed that 1782J22 bound to rabbit, human and rhesus GM-CSF, whereas G9 bound to only human and rhesus GM-CSF but not rabbit GM-CSF. (See FIG. 7 and Example 8). Therefore, it is postulated that the MAbs 1783J22 and G9 also can have differences in biological and therapeutic activities.

The invention is based on novel monoclonal antibodies and antibody fragments that neutralize GM-CSF. In some embodiments, these monoclonal antibodies and antibody fragments have a particularly high potency in neutralizing GM-CSF in vitro. Such antibodies are desirable, as only low concentrations are required in order to neutralize a given amount of GM-CSF. This facilitates higher levels of therapeutic potency while administering lower amounts of antibody. Human monoclonal antibodies and the immortalized B cell clones that secrete such antibodies are also included within the scope of the invention.

Antibodies of the invention also include antibody fragments. A "fragment" refers to polypeptide sequences which are at least about 10, 15, 20, 30, 40, 50, 60, 70, 80 90 or about 100 amino acids in length, and which retain some biological activity or immunological activity of the full-length sequence, for example, binding affinity or avidity and immune effector activity.

The invention also relates to the characterization of the epitope to which the antibodies bind and the use of that epitope in raising an immune response.

The invention also relates to various methods and uses involving the antibodies of the invention and the epitopes to which they bind.

The invention provides novel monoclonal or recombinant antibodies having particularly high potency in neutralizing GM-CSF. The invention also provides fragments of these recombinant or monoclonal antibodies, particularly fragments that retain the antigen-binding activity of the antibodies, for example which retain at least one complementarity determining region (CDR) specific for GM-CSF. In this specification, by "high potency in neutralizing GM-CSF" is meant that an antibody molecule of the invention neutralizes GM-CSF in a standard assay at a concentration ($IC_{50}$) lower than that required by antibodies known in the art.

Preferably, the antibody molecule of the present invention can neutralize at a concentration of 0.16 µg/ml or lower (i.e. 0.15, 0.125, 0.1, 0.075, 0.05, 0.025, 0.02, 0.016, 0.015, 0.0125, 0.01, 0.0075, 0.005, 0.004 or lower), preferably 0.016 µg/ml or lower (an antibody concentration of $10^{-8}$ or lower, preferably $10^{-9}$ M or lower, preferably $10^{-10}$ M or lower, i.e. $10^{-11}$ M, $10^{-12}$ M, $10^{-13}$ M or lower). This means that only very low concentrations of antibody are required for 50% neutralization of GM-CSF in vitro. Potency can be measured using a standard neutralization assay as described in the art.

The antibodies of the invention are able to neutralize GM-CSF. Monoclonal antibodies can be produced by known procedures, e.g., as described by R. Kennet et al. in "Monoclonal Antibodies and Functional Cell Lines; Progress and Applications". Plenum Press (New York), 1984. Further materials and methods applied are based on known procedures, e.g., such as described in J. Virol. 67:6642-6647, 1993.

These antibodies can be used as prophylactic or therapeutic agents upon appropriate formulation, or as a diagnostic tool.

A "neutralizing antibody" is one that can neutralize an activity of that antigen in vivo or in vitro. The invention provides a neutralizing monoclonal human antibody, wherein the antibody recognizes an antigen from GM-CSF.

The CDRs of the antibody heavy chains are referred to as CDRH1, CDRH2 and CDRH3, respectively. Similarly, the CDRs of the antibody light chains are referred to as CDRL1, CDRL2 and CDRL3, respectively. The positions of the CDR amino acids are defined according to the IMGT numbering system as: CDR1—IMGT positions 27 to 38, CDR2—IMGT positions 56 to 65 and CDR3—IMGT positions 105 to 117. (Lefranc, M P. et al. 2003 IMGT unique numbering for immunoglobulin and T cell receptor variable domains and Ig superfamily V-like domains. Dev Comp Immunol. 27(1):55-77; Lefranc, M P. 1997. Unique database numbering system for immunogenetic analysis. Immunology Today, 18:509; Lefranc, M P. 1999. The IMGT unique numbering for Immunoglobulins, T cell receptors and Ig-like domains. The Immunologist, 7:132-136.)

A phylogram is a branching diagram (tree) assumed to be an estimate of phylogeny, branch lengths are proportional to the amount of inferred evolutionary change. Tree diagrams of the five heavy chains and the five light chains were prepared using ClustalW (Larkin M. A., Blackshields G., Brown N. P., Chenna R., McGettigan P. A., McWilliam H., Valentin F., Wallace I. M., Wilm A., Lopez R., Thompson J. D., Gibson T. J. and Higgins D. G. *Bioinformatics* 23(21): 2947-2948 (2007); Higgins D G et al. Nucleic Acids Research 22: 4673-4680. (1994)) and are shown in FIGS. 3A and 3B respectively.

Preferably an antibody according to the invention is a novel monoclonal antibody referred to herein as 1783J22.

The 1783J22 antibody includes a heavy chain variable region (SEQ ID NO: 3), encoded by the nucleic acid sequence shown below in SEQ ID NO: 7, and a light chain variable region (SEQ ID NO: 6) encoded by the nucleic acid sequence shown in SEQ ID NO: 13.

The amino acids encompassing the CDRs as defined by Chothia, C. et al. (1989, Nature, 342: 877-883) are underlined and those defined by Kabat E. A. et al. (1991, Sequences of Proteins of Immunological Interest, 5$^{th}$ edit., NIH Publication no. 91-3242 U.S. Department of Health and Human Services.) are highlighted in bold in the sequences below.

The heavy chain CDRs of the 1783J22 antibody have the following sequences per Kabat definition: FPFHKYTMT (SEQ ID NO: 8), VSGVNGKTYYSPSVRG (SEQ ID NO: 9), and GPGGHLHYYYGLDV (SEQ ID NO: 10). The light chain CDRs of the 1783J22 antibody have the following sequences per Kabat definition: RASQAINNYVA (SEQ ID NO: 14), GASNLQP (SEQ ID NO: 15), and QNYFGYPLT (SEQ ID NO: 16).

The heavy chain CDRs of the 1783J22 antibody have the following sequences per Chothia definition: GFPFHKYTMT (SEQ ID NO: 11), VSGVNGKTY (SEQ ID NO: 12), and GPGGHLHYYYGLDV (SEQ ID NO: 10). The light chain CDRs of the 1783J22 antibody have the following sequences per Chothia definition: RASQAINNYVA (SEQ ID NO: 14), GASNLQP (SEQ ID NO: 15), and QNYFGYPLT (SEQ ID NO: 16).

1783J22 gamma heavy chain nucleotide sequence (variable region in bold):

(SEQ ID NO: 1)
ATGGAGTTTGGGCTGAGCTGGCTTTTTCTTGTGACTGTTCTAAAAGGTGT

CCACTGTGAGGTCCAATTATTGCAGTCGGGGGGGGGCCTGACACATCCTG

GGGGGTCCCTGAGACTCTCATGTGCGGCGTCTGGCTTCCCCTTTCACAAA

TATACCATGACTTGGGTCCGCCAGCCTCCAGGGAAGGGCCTGGAGTGGGT

CTCAAGTGTTAGTGGTGTCAACGGCAAGACATATTATAGTCCCTCCGTGA

GGGGCCGCGCCATCGTCTCCAGAGACGACTCCAACAGTATGTTGTTTTTG

GAAATCAAGAACATGACAGCCGGGACACGGCCCTCTACTTCTGCGCCAA

AGGGCCGGGTGGCCATCTTCATTATTACTATGGTCTAGACGTCTGGGCC

ATGGGACCTCGGTCACCGTCTCGAGCGCCTCCACCAAGGGCCCATCGGTC

TTCCCCCTGGCACCCTCCTCCAAGAGCACCTCTGGGGGCACAGCGGCCCT

GGGCTGCCTGGTCAAGGACTACTTCCCCGAACCGGTGACGGTGTCGTGGA

ACTCAGGCGCCCTGACCAGCGGCGTGCACACCTTCCCGGCTGTCCTACAG

TCCTCAGGACTCTACTCCCTCAGCAGCGTGGTGACCGTGCCCTCCAGCAG

CTTGGGCACCCAGACCTACATCTGCAACGTGAATCACAAGCCCAGCAACA

CCAAGGTGGACAAGAGAGTTGAGCCCAAATCTTGTGACAAAACTCACACA

TGCCCACCGTGCCCAGCACCTGAACTCCTGGGGGGACCGTCAGTCTTCCT

-continued

CTTCCCCCCAAAACCCAAGGACACCCTCATGATCTCCCGGACCCCTGAGG

TCACATGCGTGGTGGTGGACGTGAGCCACGAAGACCCTGAGGTCAAGTTC

AACTGGTACGTGGACGGCGTGGAGGTGCATAATGCCAAGACAAAGCCGCG

GGAGGAGCAGTACAACAGCACGTACCGTGTGGTCAGCGTCCTCACCGTCC

TGCACCAGGACTGGCTGAATGGCAAGGAGTACAAGTGCAAGGTCTCCAAC

AAAGCCCTCCCAGCCCCCATCGAGAAAACCATCTCCAAAGCCAAAGGGCA

GCCCCGAGAACCACAGGTGTACACCCTGCCCCCATCCCGGGAGGAGATGA

CCAAGAACCAGGTCAGCCTGACCTGCCTGGTCAAAGGCTTCTATCCCAGC

GACATCGCCGTGGAGTGGGAGAGCAATGGGCAGCCGGAGAACAACTACAA

GACCACGCCTCCCGTGCTGGACTCCGACGGCTCCTTCTTCCTCTATAGCA

AGCTCACCGTGGACAAGAGCAGGTGGCAGCAGGGGAACGTCTTCTCATGC

TCCGTGATGCATGAGGCTCTGCACAACCACTACACGCAGAAGAGCCTCTC

CCTGTCTCCGGGTAAATGA

1783J22 gamma heavy chain variable region nucleotide sequence:

(SEQ ID NO: 7)
GAGGTCCAATTATTGCAGTCGGGGGGGGGCCTGACACATCCTGGGGGGTC

CCTGAGACTCTCATGTGCGGCGTCTGGCTTCCCCTTTCACAAATATACCA

TGACTTGGGTCCGCCAGCCTCCAGGGAAGGGCCTGGAGTGGGTCTCAAGT

GTTAGTGGTGTCAACGGCAAGACATATTATAGTCCCTCCGTGAGGGGCCG

CGCCATCGTCTCCAGAGACGACTCCAACAGTATGTTGTTTTTGGAAATCA

AGAACATGACAGCCGGGACACGGCCCTCTACTTCTGCGCCAAAGGGCCG

GGTGGCCATCTTCATTATTACTATGGTCTAGACGTCTGGGGCCATGGGAC

CTCGGTCACCGTCTCGAGC

1783J22 gamma heavy chain amino acid sequence (variable region in bold):

(SEQ ID NO: 2)
EVQLLQSGGGLTHPGGSLRLSCAASGFPFHKYTMTWVRQPPGKGLEWVSS

VSGVNGKTYYSPSVRGRAIVSRDDSNSMLFLEIKNMTAGDTALYFCAKGP

GGHLHYYYGLDVWGHGTSVTVSSASTKGPSVFPLAPSSKSTSGGTAALGC

LVKDYFPEPVTVSWNSGALTSGVHTFPAVLQSSGLYSLSSVVTVPSSSLG

TQTYICNVNHKPSNTKVDKRVEPKSCDKTHTCPPCPAPELLGGPSVFLFP

PKPKDTLMISRTPEVTCVVVDVSHEDPEVKFNWYVDGVEVHNAKTKPREE

QYNSTYRVVSVLTVLHQDWLNGKEYKCKVSNKALPAPIEKTISKAKGQPR

EPQVYTLPPSREEMTKNQVSLTCLVKGFYPSDIAVEWESNGQPENNYKTT

PPVLDSDGSFFLYSKLTVDKSRWQQGNVFSCSVMHEALHNHYTQKSLSLS

PGK

1783J22 gamma heavy chain variable region amino acid sequence (Kabat CDRs underlined, Chothia CDRs in bold italics):

(SEQ ID NO: 3)
EVQLLQSGGGLTHPGGSLRLSCAAS*GFPFHKYT*MTWVRQPPGKGLEWVSS

*VSGVNGKTY*YSPSVRGRAIVSRDDSNSMLFLEIKNMTAGDTALYFCAK

*GPGGHLHYYYGLDV*WGHGTSVTVSS

1783J22 gamma heavy chain Kabat CDRs:

(SEQ ID NO: 8)
CDR1: FPFHKYTMT

```
                                          (SEQ ID NO: 9)
CDR2: VSGVNGKTYYSPSVRG (SEQ ID NO: 10)
CDR3: GPGGHLHYYYGLDV

1783J22 gamma heavy chain Chothia CDRs:
                                          (SEQ ID NO: 11)
CDR1: GFPFHKYTMT (SEQ ID NO: 12)
CDR2: VSGVNGKTY (SEQ ID NO: 10)
CDR3: GPGGHLHYYYGLDV 1783J22 kappa light chain nucleic acid sequence
(variable region in bold):
                                          (SEQ ID NO: 4)
ATGNNCATGAGAGTCCTCGCTCAGCTCCTGGGGCTCCTGCTGCTCTGTTT

CCCAGGTGCCAGATGTGACATCCAGATGACCCAATCCCCATCCTCACTGT

CTGCATCTATTGGAGATAGAGTCACCATCTCTTGTCGGGCGAGTCAGGCC

ATCAACAATTATGTTGCCTGGTTTCAGCAGTCTGCAGGAAAAGCCCCTAA

GTCTCTCATCTATGGTGCGTCGAATTTGCAACCTGGTGTCCCACCAAGGT

TCAGCGGCAGTGTATCTGGGACAAATTTCTCTCTCACCATCGACGGTCTG

CAGTCCGAAGACTTTGCAACTTATTTCTGTCAAAATTACTTTGGTTATCC

CCTCACTTTCGGCGGTGGGACCACACTGGAGATCAAACGTACGGTGGCTG

CACCATCTGTCTTCATCTTCCCGCCATCTGATGAGCAGTTGAAATCTGGA

ACTGCCTCTGTTGTGTGCCTGCTGAATAACTTCTATCCCAGAGAGGCCAA

AGTACAGTGGAAGGTGGATAACGCCCTCCAATCGGGTAACTCCCAGGAGA

GTGTCACAGAGCAGGACAGCAAGGACAGCACCTACAGCCTCAGCAGCACC

CTGACGCTGAGCAAAGCAGACTACGAGAAACACAAAGTCTACGCCTGCGA

AGTCACCCATCAGGGCCTGAGCTCGCCCGTCACAAAGAGCTTCAACAGGG

GAGAGTGTTAG

1783J22 kappa light chain variable region nucleic
acid sequence:
                                          (SEQ ID NO: 13)
GACATCCAGATGACCCAATCCCCATCCTCACTGTCTGCATCTATTGGAGA

TAGAGTCACCATCTCTTGTCGGGCGAGTCAGGCCATCAACAATTATGTTG

CCTGGTTTCAGCAGTCTGCAGGAAAAGCCCCTAAGTCTCTCATCTATGGT

GCGTCGAATTTGCAACCTGGTGTCCCACCAAGGTTCAGCGGCAGTGTATC

TGGGACAAATTTCTCTCTCACCATCGACGGTCTGCAGTCCGAAGACTTTG

CAACTTATTTCTGTCAAAATTACTTTGGTTATCCCCTCACTTTCGGCGGT

GGGACCACACTGGAGATCAAAC

1783J22 kappa light chain amino acid sequence
(variable region in bold):
                                          (SEQ ID NO: 5)
DIQMTQSPSSLSASIGDRVTISCRASQAINNYVAWFQQSAGKAPKSLIYG

ASNLQPGVPPRFSGSVSGTNFSLTIDGLQSEDFATYFCQNYFGYPLTFGG

GTTLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

1783J22 kappa light chain variable region amino acid sequence (Kabat CDRs underlined, Chothia CDRs
in bold italics):
                                          (SEQ ID NO: 6)
DIQMTQSPSSLSASIGDRVTISC*RASQAINNYVA*WFQQSAGKAPKSLIY

*GASNLQP*GVPPRFSGSVSGTNFSLTIDGLQSEDFATYFC*QNYFGYPLT*F

GGGTTLEIK

1783J22 kappa light chain Kabat CDRs:
                                          (SEQ ID NO: 14)
CDR1: RASQAINNYVA (SEQ ID NO: 15)
CDR2: GASNLQP (SEQ ID NO: 16)
CDR3: QNYFGYPLT 1783J22 kappa light chain Chothia CDRs:
                                          (SEQ ID NO: 14)
CDR1: RASQAINNYVA (SEQ ID NO: 15)
CDR2: GASNLQP (SEQ ID NO: 16)
CDR3: QNYFGYPLT
```

In one aspect, an antibody according to the invention contains a heavy chain having the amino acid sequence of SEQ ID NOs: 2 or 3 and a light chain having the amino acid sequence of SEQ ID NOs: 5 or 6. Alternatively, an antibody according to the invention contains a heavy chain variable region having the amino acid sequence of SEQ ID NO: 3 and a light chain variable region having the amino acid sequence of SEQ ID NO: 6.

In another aspect, an antibody according to the invention contains a heavy chain having the amino acid sequence encoded by the nucleic acid sequence of SEQ ID NOs: 1 or 7 and a light chain having the amino acid sequence encoded by the nucleic acid sequence of SEQ ID NOs: 4 or 13. Alternatively, an antibody according to the invention contains a heavy chain variable region having the amino acid sequence encoded by the nucleic acid sequence of SEQ ID NO: 7 and a light chain variable region having the amino acid sequence encoded by the nucleic acid sequence of SEQ ID NO: 13. Furthermore, an antibody according to the invention contains a heavy chain having the amino acid sequence encoded by a nucleic acid sequence of SEQ ID NO: 1, which contains a silent or degenerate mutation, and a light chain having the amino acid sequence encoded by the nucleic acid sequence of SEQ ID NO: 4, which contains a silent or degenerate mutation. Silent and degenerate mutations alter the nucleic acid sequence, but do not alter the resultant amino acid sequence.

Preferably the three heavy chain CDRs include an amino acid sequence of at least 90%, 92%, 95%, 97%, 98%, 99%, or more identical to the amino acid sequence of FPFHKYTMT (SEQ ID NO: 8), VSGVNGKTYYSPSVRG (SEQ ID NO: 9), or GPGGHLHYYYGLDV (SEQ ID NO: 10) (as determined by the Kabat method) or GFPFHKYTMT (SEQ ID NO: 11), VSGVNGKTY (SEQ ID NO: 12), and GPGGHLHYYYGLDV (SEQ ID NO: 10) (as determined by the Chothia method) and a light chain with three CDRs that include an amino acid sequence of at least 90%, 92%, 95%, 97%, 98%, 99%, or more identical to the amino acid sequence of RASQAINNYVA (SEQ ID NO: 14), GASNLQP (SEQ ID NO: 15), and QNYFGYPLT (SEQ ID NO: 16) (as determined by the Kabat method) or RASQAINNYVA (SEQ ID NO: 14), GASNLQP (SEQ ID NO: 15), and QNYFGYPLT (SEQ ID NO: 16) (as determined by the Chothia method).

The heavy chain of the anti-GM-CSF monoclonal antibody is derived from a germ line variable (V) gene such as, for example, the IGHV3 germline gene.

The anti-GM-CSF antibodies of the invention include a variable heavy chain ($V_H$) region encoded by human IGHV3-23 germline gene sequences. Preferably, the anti-GM-CSF antibodies of the invention include a variable heavy chain ($V_H$) region encoded by human IGHV3-23 germline gene sequences having the IGHV3-23*02 allele. The anti-GM-CSF antibodies of the invention also include constant regions encoded by human IGHJ6 and IGHD3-22 germline gene sequences, and preferably, having the IGHJ6*02 and IGHD3-22*01 alleles, respectively. A human IGHV3-23 germline gene sequences is shown, e.g., in Accession number AY998715. A human IGHJ6 germline gene sequences is shown, e.g., in Accession number AY998715. The anti-GM-CSF antibodies of the invention include a $V_H$ region that is encoded by a nucleic acid sequence that is at least 75% homologous to the IGHV3-23 germline gene sequence. Preferably, the nucleic acid sequence is at least 90%, 95%, 96%, 97% homologous to the IGHV3-23 germline gene sequence, and more preferably, at least 98%, 99% homologous to the IGHV3-23 germline gene sequence. The $V_H$ region of the anti-GM-CSF antibody is at least 75% homologous to the amino acid sequence of the $V_H$ region encoded by the IGHV3-23 $V_H$ germline gene sequence. Preferably, the amino acid sequence of $V_H$ region of the anti-GM-CSF antibody is at least 90%, 95%, 96%, 97% homologous to the amino acid sequence encoded by the IGHV3-23 germline gene sequence, and more preferably, at least 98%, 99% homologous to the sequence encoded by the IGHV3-23 germline gene sequence.

The light chain of the anti-GM-CSF monoclonal antibody is derived from a germ line variable (V) gene such as, for example, the IGKV1 germline gene.

The anti-GM-CSF antibodies of the invention include a variable light chain ($V_L$) region encoded by human IGKV1-16 germline gene sequences. Preferably, the anti-GM-CSF antibodies of the invention include a variable light chain ($V_L$) region encoded by human IGKV1-16 germline gene sequences having the IGKV1-16*01 allele. The anti-GM-CSF antibodies of the invention also include constant regions encoded by human IGKJ4 germline gene sequences, and preferably, having the IGKJ4*01 allele. A human IGKV1-16 $V_L$ germline gene sequence is shown, e.g., Accession numbers EU599329, EF589394, EF589555, EF589492, EF589439, EF589569, and EF589393. A human IGKJ4 germline gene sequence is shown, e.g., Accession numbers AY998691, AY998685, AY998683, AF168801, EF589383, EF589502, EF589488, EF589481, EF589472, EF589464, EF589441, EF589477, and EF589385. The anti-GM-CSF antibodies include a $V_L$ region that is encoded by a nucleic acid sequence that is at least 80% homologous to the IGKV1-16 germline gene sequence. Preferably, the nucleic acid sequence is at least 90%, 95%, 96%, 97% homologous to the IGKV1-16 germline gene sequence, and more preferably, at least 98%, 99% homologous to the IGKV1-16 germline gene sequence. The $V_L$ region of the anti-GM-CSF antibody is at least 80% homologous to the amino acid sequence of the $V_L$ region encoded the IGKV1-16 germline gene sequence. Preferably, the amino acid sequence of $V_L$ region of the anti-GM-CSF antibody is at least 90%, 95%, 96%, 97% homologous to the amino acid sequence encoded by the IGKV1-16 germline gene sequence, and more preferably, at least 98%, 99% homologous to the sequence encoded by the IGKV1-16 germline gene sequence.

It is to be understood that because of the natural sequence variation likely to exist among heavy and light chains and the genes encoding them, one skilled in the art would expect to find some level of variation within the amino acid sequences or the genes encoding them, while still maintaining the unique binding properties (e.g., specificity and affinity) of the antibodies of the present invention. Accordingly, such variants and homologs are considered substantially the same as one another and are included within the scope of the present invention.

Monoclonal and recombinant antibodies are particularly useful in identification and purification of the individual polypeptides or other antigens against which they are directed. The antibodies of the invention have additional utility in that they may be employed as reagents in immunoassays, radioimmunoassays (RIA) or enzyme-linked immunosorbent assays (ELISA). In these applications, the antibodies can be labeled with an analytically-detectable reagent such as a radioisotope, a fluorescent molecule or an enzyme. The antibodies may also be used for the molecular identification and characterization (epitope mapping) of antigens.

As mentioned above, the antibodies of the invention can be used to map the epitopes to which they bind. Applicants have discovered that the antibody 1783J22 neutralizes GM-CSF. Although the Applicant does not wish to be bound by this theory, it is postulated that the 1783J22 antibody may bind to one or more conformational epitopes formed by GM-CSF.

The epitopes recognized by these antibodies may have a number of uses. The epitopes and mimotopes in purified or synthetic form can be used to raise immune responses (i.e. as a vaccine, or for the production of antibodies for other uses) or for screening patient serum for antibodies that immunoreact with the epitopes or mimotopes. Preferably, such an epitope or mimotope, or antigen comprising such an epitope or mimotope is used as a vaccine for raising an immune response. The antibodies of the invention can also be used in a method to monitor the quality of vaccines in particular to check that the antigen in a vaccine contains the correct immunogenic epitope in the correct conformation.

The epitopes may also be useful in screening for ligands that bind to said epitopes. Such ligands preferably block the epitopes and thus prevent infection. Such ligands are encompassed within the scope of the invention.

Methods of Making and Using Anti-GM-CSF Antibodies

As will be understood by the skilled artisan, general description of antibodies herein and methods of preparing and using the same also apply to individual antibody polypeptide constituents and antibody fragments.

Standard techniques of molecular biology may be used to prepare DNA sequences coding for the antibodies or fragments of the antibodies of the present invention. Desired DNA sequences may be synthesized completely or in part using oligonucleotide synthesis techniques. Site-directed mutagenesis and polymerase chain reaction (PCR) techniques may be used as appropriate.

Any suitable host cell/vector system may be used for expression of the DNA sequences encoding the antibody molecules of the present invention or fragments thereof. Bacterial, for example *E. coli*, and other microbial systems may be used, in part, for expression of antibody fragments such as Fab and F(ab')$_2$ fragments, and especially Fv fragments and single chain antibody fragments, for example, single chain Fvs. Eukaryotic, e.g. mammalian, host cell expression systems may be used for production of larger antibody molecules, including complete antibody molecules. Suitable mammalian host cells include CHO, HEK293T, PER.C6, myeloma or hybridoma cells.

The present invention also provides a process for the production of an antibody molecule according to the present invention comprising culturing a host cell comprising a vector of the present invention under conditions suitable for leading to expression of protein from DNA encoding the antibody molecule of the present invention, and isolating the antibody molecule.

The antibody molecule may comprise only a heavy or light chain polypeptide, in which case only a heavy chain or light chain polypeptide coding sequence needs to be used to transfect the host cells. For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

Alternatively, antibodies according to the invention may be produced by i) expressing a nucleic acid sequence according to the invention in a cell, and ii) isolating the expressed antibody product. Additionally, the method may include iii) purifying the antibody.

Transformed B cells are screened for those producing antibodies of the desired antigen specificity, and individual B cell clones can then be produced from the positive cells. The screening step may be carried out by ELISA, by staining of tissues or cells (including transfected cells), a neutralization assay or one of a number of other methods known in the art for identifying desired antigen specificity. The assay may select on the basis of simple antigen recognition, or may select on the additional basis of a desired function e.g. to select neutralizing antibodies rather than just antigen-binding antibodies, to select antibodies that can change characteristics of targeted cells, such as their signaling cascades, their shape, their growth rate, their capability of influencing other cells, their response to the influence by other cells or by other reagents or by a change in conditions, their differentiation status, etc.

The cloning step for separating individual clones from the mixture of positive cells may be carried out using limiting dilution, micromanipulation, single cell deposition by cell sorting or another method known in the art. Preferably the cloning is carried out using limiting dilution.

The immortalized B cell clones of the invention can be used in various ways e.g. as a source of monoclonal antibodies, as a source of nucleic acid (DNA or mRNA) encoding a monoclonal antibody of interest, for research, etc.

The antibodies of the present invention may be polyclonal or monoclonal antibodies. However, in preferred embodiments, they are monoclonal. In particular embodiments, antibodies of the present invention are human antibodies. Methods of producing polyclonal and monoclonal antibodies are known in the art and described generally, e.g., in U.S. Pat. No. 6,824,780. Typically, the antibodies of the present invention are produced recombinantly, using vectors and methods available in the art, as described further below. Human antibodies may also be generated by in vitro activated B cells (see U.S. Pat. Nos. 5,567,610 and 5,229,275).

Human antibodies may also be produced in transgenic animals (e.g., mice) that are capable of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice results in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggemann et al., Year in Immuno., 7:33 (1993); U.S. Pat. Nos. 5,545,806, 5,569,825, 5,591,669 (all of GenPharm); U.S. Pat. No. 5,545,807; and WO 97/17852. Such animals may be genetically engineered to produce human antibodies comprising a polypeptide of the present invention.

In certain embodiments, antibodies of the present invention are chimeric antibodies that comprise sequences derived from both human and non-human sources. In particular embodiments, these chimeric antibodies are humanized or primatized. In practice, humanized antibodies are typically human antibodies in which some hypervariable region residues and possibly some FR residues are substituted by residues from analogous sites in rodent antibodies.

In the context of the present invention, chimeric antibodies also include human antibodies wherein the human hypervariable region or one or more CDRs are retained, but one or more other regions of sequence have been replaced by corresponding sequences from a non-human animal.

The choice of non-human sequences, both light and heavy, to be used in making the chimeric antibodies is important to reduce antigenicity and human anti-non-human antibody responses when the antibody is intended for human therapeutic use. It is further important that chimeric antibodies retain high binding affinity for the antigen and other favorable biological properties. To achieve this goal, according to a preferred method, chimeric antibodies are prepared by a process of analysis of the parental sequences and various conceptual chimeric products using three-dimensional models of the parental human and non-human sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

As noted above, antibodies (or immunoglobulins) can be divided into five different classes, based on differences in the amino acid sequences in the constant region of the heavy chains. All immunoglobulins within a given class have very similar heavy chain constant regions. These differences can be detected by sequence studies or more commonly by serological means (i.e. by the use of antibodies directed to these differences). Antibodies, or fragments thereof, of the present invention may be any class, and may, therefore, have a gamma, mu, alpha, delta, or epsilon heavy chain. A gamma chain may be gamma 1, gamma 2, gamma 3, or gamma 4; and an alpha chain may be alpha 1 or alpha 2.

In a preferred embodiment, an antibody of the present invention, or fragment thereof, is an IgG. IgG is considered the most versatile immunoglobulin, because it is capable of carrying out all of the functions of immunoglobulin molecules. IgG is the major Ig in serum, and the only class of Ig that crosses the placenta. IgG also fixes complement, although the IgG4 subclass does not. Macrophages, monocytes, PMN's and some lymphocytes have Fc receptors for the Fc region of IgG. Not all subclasses bind equally well; IgG2 and IgG4 do not bind to Fc receptors. A consequence of binding to the Fc receptors on PMN's, monocytes and macrophages is that the cell can now internalize the antigen better. IgG is an opsonin that enhances phagocytosis. Binding of IgG to Fc receptors on other types of cells results in the activation of other functions. Antibodies of the present invention may be of any IgG subclass.

In another preferred embodiment, an antibody, or fragment thereof, of the present invention is an IgE. IgE is the least common serum Ig since it binds very tightly to Fc receptors on basophils and mast cells even before interacting with antigen. As a consequence of its binding to basophils and mast cells, IgE is involved in allergic reactions. Binding of the allergen to the IgE on the cells results in the release of various pharmacological mediators that result in allergic symptoms. IgE also plays a role in parasitic helminth diseases. Eosinophils have Fc receptors for IgE and binding of eosinophils to IgE-coated helminths results in killing of the parasite. IgE does not fix complement.

In various embodiments, antibodies of the present invention, and fragments thereof, comprise a variable light chain that is either kappa or lambda. The lambda chain may be any of subtype, including, e.g., lambda 1, lambda 2, lambda 3, and lambda 4.

As noted above, the present invention further provides antibody fragments comprising a polypeptide of the present invention. In certain circumstances there are advantages of using antibody fragments, rather than whole antibodies. For example, the smaller size of the fragments allows for rapid clearance, and may lead to improved access to certain tissues, such as solid tumors. Examples of antibody fragments include: Fab, Fab', F(ab')$_2$ and Fv fragments; diabodies; linear antibodies; single-chain antibodies; and multispecific antibodies formed from antibody fragments.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from E. coli, thus allowing the facile production of large amounts of these fragments. Fab'-SH fragments can be directly recovered from E. coli and chemically coupled to form F(ab')$_2$ fragments (Carter et al., Bio/Technology 10:163-167 (1992)). According to another approach, F(ab')$_2$ fragments can be isolated directly from recombinant host cell culture. Fab and F(ab')$_2$ fragment with increased in vivo half-life comprising a salvage receptor binding epitope residues are described in U.S. Pat. No. 5,869,046. Other techniques for the production of antibody fragments will be apparent to the skilled practitioner.

In other embodiments, the antibody of choice is a single chain Fv fragment (scFv). See WO 93/16185; U.S. Pat. Nos. 5,571,894; and 5,587,458. Fv and sFv are the only species with intact combining sites that are devoid of constant regions. Thus, they are suitable for reduced nonspecific binding during in vivo use. sFv fusion proteins may be constructed to yield fusion of an effector protein at either the amino or the carboxy terminus of an sFv. See Antibody Engineering, ed. Borrebaeck, supra. The antibody fragment may also be a "linear antibody", e.g., as described in U.S. Pat. No. 5,641,870 for example. Such linear antibody fragments may be monospecific or bispecific.

In certain embodiments, antibodies of the present invention are bispecific or multispecific. Bispecific antibodies are antibodies that have binding specificities for at least two different epitopes. Exemplary bispecific antibodies may bind to two different epitopes of a single antigen. Other such antibodies may combine a first antigen binding site with a binding site for a second antigen. Alternatively, an anti-GM-CSF arm may be combined with an arm that binds to Fc receptors for IgG (FcγR), such as FcγRI (CD64), FcγRII (CD32) and FcγRIII (CD16), so as to focus and localize cellular defense mechanisms to the target cell. Bispecific antibodies may also be used to localize cytotoxic agents to infected cells. These antibodies possess an GM-CSF-binding arm and an arm that binds the cytotoxic agent (e.g., saporin, anti-interferon-α, vinca alkaloid, ricin A chain, methotrexate or radioactive isotope hapten). Bispecific antibodies can be prepared as full length antibodies or antibody fragments (e.g., F(ab')$_2$ bispecific antibodies). WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fcα antibody is shown in WO98/02463. U.S. Pat. No. 5,821,337 teaches a bispecific anti-ErbB2/anti-CD3 antibody.

Methods for making bispecific antibodies are known in the art. Traditional production of full length bispecific antibodies is based on the co-expression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of ten different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J., 10:3655-3659 (1991).

According to a different approach, antibody variable domains with the desired binding specificities (antibody-antigen combining sites) are fused to immunoglobulin constant domain sequences. Preferably, the fusion is with an Ig heavy chain constant domain, comprising at least part of the hinge, $C_H2$, and $C_H3$ regions. It is preferred to have the first heavy-chain constant region ($C_H1$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant affect on the yield of the desired chain combination.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121:210 (1986).

According to another approach described in U.S. Pat. No. 5,731,168, the interface between a pair of antibody molecules can be engineered to maximize the percentage of heterodimers that are recovered from recombinant cell culture. The preferred interface comprises at least a part of the $C_H3$ domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229: 81 (1985) describe a procedure wherein intact antibodies are proteolytically cleaved to generate F(ab')$_2$ fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., J. Exp. Med., 175: 217-225 (1992) describe the production of a humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol., 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA, 90:6444-6448 (1993) has provided an alternative mechanism for making bispecific antibody fragments. The fragments comprise a $V_H$ connected to a $V_L$ by a linker that is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., J. Immunol., 152:5368 (1994).

Antibodies with more than two valencies are contemplated. For example, trispecific antibodies can be prepared. Tutt et al., J. Immunol. 147: 60 (1991). A multivalent antibody may be internalized (and/or catabolized) faster than a bivalent antibody by a cell expressing an antigen to which the antibodies bind. The antibodies of the present invention can be multivalent antibodies with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-(X1)$_n$-VD2-(X2)$_n$-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a $C_L$ domain.

Antibodies of the present invention further include single chain antibodies.

In particular embodiments, antibodies of the present invention are internalizing antibodies.

Amino acid sequence modification(s) of the antibodies described herein are contemplated. For example, it may be desirable to improve the binding affinity and/or other biological properties of the antibody. Amino acid sequence variants of the antibody may be prepared by introducing appropriate nucleotide changes into a polynucleotide that encodes the antibody, or a chain thereof, or by peptide synthesis. Such modifications include, for example, deletions from, and/or insertions into and/or substitutions of, residues within the amino acid sequences of the antibody. Any combination of deletion, insertion, and substitution may be made to arrive at the final antibody, provided that the final construct possesses the desired characteristics. The amino acid changes also may alter post-translational processes of the antibody, such as changing the number or position of glycosylation sites. Any of the variations and modifications described above for polypeptides of the present invention may be included in antibodies of the present invention.

A useful method for identification of certain residues or regions of an antibody that are preferred locations for mutagenesis is called "alanine scanning mutagenesis" as described by Cunningham and Wells in Science, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with PSCA antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed anti-antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of an antibody include the fusion to the N- or C-terminus of the antibody to an enzyme (e.g., for ADEPT) or a polypeptide that increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative and non-conservative substitutions are contemplated.

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain.

Any cysteine residue not involved in maintaining the proper conformation of the antibody also may be substituted, generally with serine, to improve the oxidative stability of the molecule and prevent aberrant crosslinking Conversely, cysteine bond(s) may be added to the antibody to improve its stability (particularly where the antibody is an antibody fragment such as an Fv fragment).

One type of substitutional variant involves substituting one or more hypervariable region residues of a parent antibody. Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and an antigen or infected cell. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetyl-galactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

The antibody of the invention is modified with respect to effector function, e.g., so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med. 176: 1191-1195 (1992) and Shopes, B. J. Immunol. 148:2918-2922 (1992). Homodimeric antibodies with enhanced anti-infection activity may also be prepared using heterobifunctional cross-linkers as described in Wolff et al., Cancer Research 53:2560-2565 (1993). Alternatively, an antibody can be engineered which has dual Fc regions and may thereby have enhanced complement lysis and ADCC capabilities. See Stevenson et al., Anti-Cancer Drug Design 3:219-230 (1989).

To increase the serum half-life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

Antibodies of the present invention may also be modified to include an epitope tag or label, e.g., for use in purification or diagnostic applications. The invention also pertains to therapy with immunoconjugates comprising an antibody conjugated to an anti-cancer agent such as a cytotoxic agent or a growth inhibitory agent. Chemotherapeutic agents useful in the generation of such immunoconjugates have been described above.

Conjugates of an antibody and one or more small molecule toxins, such as a calicheamicin, maytansinoids, a trichothene, and CC1065, and the derivatives of these toxins that have toxin activity, are also contemplated herein.

In one preferred embodiment, an antibody (full length or fragments) of the invention is conjugated to one or more maytansinoid molecules. Maytansinoids are mitotic inhibitors that act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

In an attempt to improve their therapeutic index, maytansine and maytansinoids have been conjugated to antibodies specifically binding to tumor cell antigens. Immunoconjugates containing maytansinoids and their therapeutic use are disclosed, for example, in U.S. Pat. Nos. 5,208,020, 5,416,064 and European Patent EP 0 425 235 B1. Liu et al., Proc. Natl. Acad. Sci. USA 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay.

Antibody-maytansinoid conjugates are prepared by chemically linking an antibody to a maytansinoid molecule without significantly diminishing the biological activity of either the antibody or the maytansinoid molecule. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody conjugates, including, for example, those disclosed in U.S. Pat. No. 5,208,020 or EP Patent 0 425 235 B1, and Chari et al., Cancer Research 52: 127-131 (1992). The linking groups include disufide groups, thioether groups, acid labile groups, photolabile groups, peptidase labile groups, or esterase labile groups, as disclosed in the above-identified patents, disulfide and thioether groups being preferred.

Immunoconjugates may be made using a variety of bifunctional protein coupling agents such as N-succinimidyl-3-(2-pyridyldithio)propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio)propionate (SPDP) (Carlsson et al., Biochem. J. 173:723-737 [1978]) and N-succinimidyl-4-(2-pyridylthio)pentanoate (SPP) to provide for a disulfide linkage. For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, Cancer Research 52: 127-131 (1992); U.S. Pat. No. 5,208, 020) may be used.

Another immunoconjugate of interest comprises an antibody conjugated to one or more calicheamicin molecules. The calicheamicin family of antibiotics is capable of producing double-stranded DNA breaks at sub-picomolar concentrations. For the preparation of conjugates of the calicheamicin family, see U.S. Pat. Nos. 5,712,374, 5,714,586, 5,739, 116, 5,767,285, 5,770,701, 5,770,710, 5,773,001, 5,877,296 (all to American Cyanamid Company). Another drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Examples of other agents that can be conjugated to the antibodies of the invention include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Enzymatically active toxins and fragments thereof that can be used include, e.g., diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolacca americana* proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes. See, for example, WO 93/21232.

The present invention further includes an immunoconjugate formed between an antibody and a compound with nucleolytic activity (e.g., a ribonuclease or a DNA endonuclease such as a deoxyribonuclease (DNase)).

For selective destruction of infected cells, the antibody includes a highly radioactive atom. A variety of radioactive isotopes are available for the production of radioconjugated anti-PSCA PSCA antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for diagnosis, it may comprise a radioactive atom for scintigraphic studies, for example $tc^{99m}$ or $I^{123}$, or a spin label for nuclear magnetic resonance (NMR) imaging (also known as magnetic resonance imaging, MRI), such as iodine-123, iodine-131, indium-111, fluorine-19, carbon-13, nitrogen-15, oxygen-17, gadolinium, manganese or iron.

The radio- or other label is incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN™ method (Fraker et al. (1978) Biochem. Biophys. Res. Commun. 80: 49-57) can be used to incorporate iodine-123. "Monoclonal Antibodies in Immunoscintigraphy" (Chatal, CRC Press 1989) describes other methods in detail.

Alternatively, a fusion protein comprising the antibody and cytotoxic agent is made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

The antibodies of the present invention are also used in antibody dependent enzyme mediated prodrug therapy (ADET) by conjugating the antibody to a prodrug-activating enzyme which converts a prodrug (e.g., a peptidyl chemotherapeutic agent, see WO81/01145) to an active anti-cancer drug (see, e.g., WO 88/07378 and U.S. Pat. No. 4,975,278).

The enzyme component of the immunoconjugate useful for ADEPT includes any enzyme capable of acting on a prodrug in such a way so as to convert it into its more active, cytotoxic form. Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, Nature 328: 457-458 (1987)). Antibody-abzyme conjugates can be prepared as described herein for delivery of the abzyme to an infected cell population.

The enzymes of this invention can be covalently bound to the antibodies by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., Nature, 312: 604-608 (1984).

Other modifications of the antibody are contemplated herein. For example, the antibody may be linked to one of a variety of nonproteinaceous polymers, e.g., polyethylene glycol, polypropylene glycol, polyoxyalkylenes, or copolymers of polyethylene glycol and polypropylene glycol. The antibody also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, 16th edition, Oslo, A., Ed., (1980).

The antibodies disclosed herein are also formulated as immunoliposomes. A "liposome" is a small vesicle composed of various types of lipids, phospholipids and/or surfactant that is useful for delivery of a drug to a mammal. The components of the liposome are commonly arranged in a bilayer formation, similar to the lipid arrangement of biological membranes. Liposomes containing the antibody are prepared by methods known in the art, such as described in Epstein et al., Proc. Natl. Acad. Sci. USA, 82:3688 (1985); Hwang et al., Proc. Natl Acad. Sci. USA, 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired a diameter. Fab' fragments of the antibody of the present invention can be conjugated to the liposomes as described in Martin et al., J. Biol. Chem. 257: 286-288 (1982) via a disulfide interchange reaction. A chemotherapeutic agent is optionally contained within the liposome. See Gabizon et al., J. National Cancer Inst. 81(19)1484 (1989).

In particular embodiments, an antibody of the present invention is an antagonist antibody, which partially or fully blocks or inhibits a biological activity of a polypeptide or cell to which it specifically or preferentially binds. In other embodiments, an antibody of the present invention is a growth inhibitory antibody, which partially or fully blocks or inhibits the growth of an infected cell to which it binds. In another embodiment, an antibody of the present invention induces apoptosis. In yet another embodiment, an antibody of the present invention induces or promotes antibody-dependent cell-mediated cytotoxicity or complement dependent cytotoxicity.

GM-CSF-expressing cells described above are used to screen the biological sample obtained from a patient for the presence of antibodies that preferentially bind to the cell expressing GM-CSF using standard biological techniques. For example, in certain embodiments, the antibodies may be labeled, and the presence of label associated with the cell detected, e.g., using FMAT or FACs analysis. In particular embodiments, the biological sample is blood, serum, plasma, bronchial lavage, or saliva. Methods of the present invention may be practiced using high throughput techniques.

Identified human antibodies may then be characterized further. For example the particular conformational epitopes with in the GM-CSF polypeptide that are necessary or sufficient for binding of the antibody may be determined, e.g., using site-directed mutagenesis of expressed GM-CSF polypeptide. These methods may be readily adapted to identify human antibodies that bind any protein expressed on a cell surface.

Polynucleotide sequences encoding the antibodies, variable regions thereof, or antigen-binding fragments thereof may be subcloned into expression vectors for the recombinant production of human anti-GM-CSF antibodies. In one embodiment, this is accomplished by obtaining mononuclear cells from the patient from the serum containing the identified GM-CSF antibody was obtained; producing B cell clones from the mononuclear cells; inducing the B cells to become antibody-producing plasma cells; and screening the supernatants produced by the plasma cells to determine if it contains the GM-CSF antibody. Once a B cell clone that produces a GM-CSF antibody is identified, reverse-transcription polymerase chain reaction (RT-PCR) is performed to clone the DNAs encoding the variable regions or portions thereof of the GM-CSF antibody. These sequences are then subcloned into expression vectors suitable for the recombinant production of human GM-CSF antibodies.

In particular embodiments of the methods described herein, B cells isolated from peripheral blood or lymph nodes are sorted, e.g., based on their being CD19 positive, and plated, e.g., as low as a single cell specificity per well, e.g., in 96, 384, or 1536 well configurations. The cells are induced to differentiate into antibody-producing cells, e.g., plasma cells, and the culture supernatants are harvested and tested for binding to cells expressing the infectious agent polypeptide on their surface using, e.g., FMAT or FACS analysis. Positive wells are then subjected to whole well RT-PCR to amplify heavy and light chain variable regions of the IgG molecule expressed by the clonal daughter plasma cells. The resulting PCR products encoding the heavy and light chain variable regions, or portions thereof, are subcloned into human antibody expression vectors for recombinant expression. The resulting recombinant antibodies are then tested to confirm their original binding specificity and may be further tested for pan-specificity across various strains of isolates of the infectious agent.

Thus, in one embodiment, a method of identifying GM-CSF antibodies is practiced as follows. First, full length or approximately full length GM-CSF cDNA is transfected into a cell line for expression of GM-CSF polypeptide. Secondly, individual human plasma or sera samples are tested for antibodies that bind the cell-expressed GM-CSF polypeptide. And lastly, mAbs derived from plasma- or serum-positive individuals are characterized for binding to the same cell-expressed GM-CSF polypeptide. Further definition of the fine specificities of the mAbs can be performed at this point.

Polynucleotides that encode GM-CSF antibodies or portions thereof of the present invention may be isolated from cells expressing GM-CSF antibodies, according to methods available in the art and described herein, including amplification by polymerase chain reaction using primers specific for conserved regions of human antibody polypeptides. For example, light chain and heavy chain variable regions may be cloned from the B cell according to molecular biology techniques described in WO 92/02551; U.S. Pat. No. 5,627,052; or Babcook et al., *Proc. Natl. Acad. Sci. USA* 93:7843-48 (1996). In certain embodiments, polynucleotides encoding all or a region of both the heavy and light chain variable regions of the IgG molecule expressed by the clonal daughter plasma cells expressing GM-CSF antibody are subcloned and sequenced. The sequence of the encoded polypeptide may be readily determined from the polynucleotide sequence.

Isolated polynucleotides encoding a polypeptide of the present invention may be subcloned into an expression vector to recombinantly produce antibodies and polypeptides of the present invention, using procedures known in the art and described herein.

Binding properties of an antibody (or fragment thereof) to GM-CSF polypeptide may generally be determined and assessed using immunodetection methods including, for example, immunofluorescence-based assays, such as immuno-histochemistry (IHC) and/or fluorescence-activated cell sorting (FACS). Immunoassay methods may include controls and procedures to determine whether antibodies bind specifically to GM-CSF, and do not recognize or cross-react with normal control cells.

Following pre-screening of serum to identify patients that produce antibodies to GM-CSF, the methods of the present invention typically include the isolation or purification of B cells from a biological sample previously obtained from a patient or subject. The patient or subject may be currently or previously diagnosed with or suspect or having a particular disease or infection, or the patient or subject may be considered free or a particular disease or infection. Typically, the patient or subject is a mammal and, in particular embodiments, a human. The biological sample may be any sample that contains B cells, including but not limited to, lymph node or lymph node tissue, pleural effusions, peripheral blood, ascites, tumor tissue, or cerebrospinal fluid (CSF). In various embodiments, B cells are isolated from different types of biological samples, such as a biological sample affected by a particular disease or infection. However, it is understood that any biological sample comprising B cells may be used for any of the embodiments of the present invention.

Once isolated, the B cells are induced to produce antibodies, e.g., by culturing the B cells under conditions that support B cell proliferation or development into a plasmacyte, plasmablast, or plasma cell. The antibodies are then screened, typically using high throughput techniques, to identify an antibody that specifically binds to a target antigen, e.g., a particular tissue, cell, infectious agent, or polypeptide. In certain embodiments, the specific antigen, e.g., cell surface polypeptide bound by the antibody is not known, while in other embodiments, the antigen specifically bound by the antibody is known.

According to the present invention, B cells may be isolated from a biological sample, e.g., a tumor, tissue, peripheral blood or lymph node sample, by any means known and available in the art. B cells are typically sorted by FACS based on the presence on their surface of a B cell-specific marker, e.g., CD19, CD138, and/or surface IgG. However, other methods known in the art may be employed, such as, e.g., column purification using CD19 magnetic beads or IgG-specific magnetic beads, followed by elution from the column. However, magnetic isolation of B cells utilizing any marker may result in loss of certain B cells. Therefore, in certain embodiments, the isolated cells are not sorted but, instead, phicol-purified mononuclear cells isolated from tumor are directly plated to the appropriate or desired number of specificities per well.

In order to identify B cells that produce an infectious agent-specific antibody, the B cells are typically plated at low density (e.g., a single cell specificity per well, 1-10 cells per well, 10-100 cells per well, 1-100 cells per well, less than 10 cells per well, or less than 100 cells per well) in multi-well or microtiter plates, e.g., in 96, 384, or 1536 well configurations. When the B cells are initially plated at a density greater than one cell per well, then the methods of the present invention may include the step of subsequently diluting cells in a well identified as producing an antigen-specific antibody, until a single cell specificity per well is achieved, thereby facilitating the identification of the B cell that produces the antigen-specific antibody. Cell supernatants or a portion thereof and/or cells may be frozen and stored for future testing and later recovery of antibody polynucleotides.

In certain embodiments, the B cells are cultured under conditions that favor the production of antibodies by the B cells. For example, the B cells may be cultured under conditions favorable for B cell proliferation and differentiation to yield antibody-producing plasmablast, plasmacytes, or plasma cells. In particular embodiments, the B cells are cultured in the presence of a B cell mitogen, such as lipopolysaccharide (LPS) or CD40 ligand. In one specific embodiment, B cells are differentiated to antibody-producing cells by culturing them with feed cells and/or other B cell activators, such as CD40 ligand.

Cell culture supernatants or antibodies obtained therefrom may be tested for their ability to bind to a target antigen, using routine methods available in the art, including those described herein. In particular embodiments, culture supernatants are tested for the presence of antibodies that bind to a target antigen using high-throughput methods. For example, B cells may be cultured in multi-well microtiter dishes, such that robotic plate handlers may be used to simultaneously sample multiple cell supernatants and test for the presence of antibodies that bind to a target antigen. In particular embodiments, antigens are bound to beads, e.g., paramagnetic or latex beads) to facilitate the capture of antibody/antigen complexes. In other embodiments, antigens and antibodies are fluorescently labeled (with different labels) and FACS analysis is performed to identify the presence of antibodies that bind to target antigen. In one embodiment, antibody binding is determined using FMAT™ analysis and instrumentation (Applied Biosystems, Foster City, Calif.). FMAT™ is a fluorescence macro-confocal platform for high-throughput screening, which mix-and-read, non-radioactive assays using live cells or beads.

In the context of comparing the binding of an antibody to a particular target antigen (e.g., a biological sample such as infected tissue or cells, or infectious agents) as compared to a control sample (e.g., a biological sample such as uninfected cells, or a different infectious agent), in various embodiments, the antibody is considered to preferentially bind a particular target antigen if at least two-fold, at least three-fold, at least five-fold, or at least ten-fold more antibody binds to the particular target antigen as compared to the amount that binds a control sample.

Polynucleotides encoding antibody chains, variable regions thereof, or fragments thereof, may be isolated from cells utilizing any means available in the art. In one embodiment, polynucleotides are isolated using polymerase chain reaction (PCR), e.g., reverse transcription-PCR (RT-PCR) using oligonucleotide primers that specifically bind to heavy or light chain encoding polynucleotide sequences or complements thereof using routine procedures available in the art. In one embodiment, positive wells are subjected to whole well RT-PCR to amplify the heavy and light chain variable regions of the IgG molecule expressed by the clonal daughter plasma cells. These PCR products may be sequenced.

The resulting PCR products encoding the heavy and light chain variable regions or portions thereof are then subcloned into human antibody expression vectors and recombinantly expressed according to routine procedures in the art (see, e.g., U.S. Pat. No. 7,112,439). The nucleic acid molecules encoding a tumor-specific antibody or fragment thereof, as described herein, may be propagated and expressed according to any of a variety of well-known procedures for nucleic acid excision, ligation, transformation, and transfection. Thus, in certain embodiments expression of an antibody fragment may be preferred in a prokaryotic host cell, such as *Escherichia coli* (see, e.g., Pluckthun et al., *Methods Enzymol.* 178:497-515 (1989)). In certain other embodiments, expression of the antibody or an antigen-binding fragment thereof may be preferred in a eukaryotic host cell, including yeast (e.g., *Saccharomyces cerevisiae, Schizosaccharomyces pombe,* and *Pichia pastoris*); animal cells (including mammalian cells); or plant cells. Examples of suitable animal cells include, but are not limited to, myeloma, COS, CHO, or hybridoma cells. Examples of plant cells include tobacco, corn, soybean, and rice cells. By methods known to those having ordinary skill in the art and based on the present disclosure, a nucleic acid vector may be designed for expressing foreign sequences in a particular host system, and then polynucleotide sequences encoding the tumor-specific antibody (or fragment thereof) may be inserted. The regulatory elements will vary according to the particular host.

One or more replicable expression vectors containing a polynucleotide encoding a variable and/or constant region may be prepared and used to transform an appropriate cell line, for example, a non-producing myeloma cell line, such as a mouse NSO line or a bacteria, such as *E. coli,* in which production of the antibody will occur. In order to obtain efficient transcription and translation, the polynucleotide sequence in each vector should include appropriate regulatory sequences, particularly a promoter and leader sequence operatively linked to the variable domain sequence. Particular methods for producing antibodies in this way are generally well known and routinely used. For example, molecular biology procedures are described by Sambrook et al. (*Molecular Cloning, A Laboratory Manual,* 2nd ed., Cold Spring Harbor Laboratory, New York, 1989; see also Sambrook et al., 3rd ed., Cold Spring Harbor Laboratory, New York, (2001)). While not required, in certain embodiments, regions of polynucleotides encoding the recombinant antibodies may be sequenced. DNA sequencing can be performed as described in Sanger et al. (*Proc. Natl. Acad. Sci. USA* 74:5463 (1977)) and the Amersham International plc sequencing handbook and including improvements thereto.

In particular embodiments, the resulting recombinant antibodies or fragments thereof are then tested to confirm their original specificity and may be further tested for pan-specificity, e.g., with related infectious agents. In particular embodiments, an antibody identified or produced according to methods described herein is tested for cell killing via antibody dependent cellular cytotoxicity (ADCC) or apoptosis, and/or well as its ability to internalize.

The present invention, in other aspects, provides polynucleotide compositions. In preferred embodiments, these polynucleotides encode a polypeptide of the invention, e.g., a region of a variable chain of an antibody that binds to GM-CSF. Polynucleotides of the invention are single-stranded (coding or antisense) or double-stranded DNA (genomic, cDNA or synthetic) or RNA molecules. RNA molecules include, but are not limited to, HnRNA molecules, which contain introns and correspond to a DNA molecule in a one-to-one manner, and mRNA molecules, which do not contain introns. Alternatively, or in addition, coding or non-coding sequences are present within a polynucleotide of the present invention. Also alternatively, or in addition, a polynucleotide is linked to other molecules and/or support materials of the invention. Polynucleotides of the invention are used, e.g., in hybridization assays to detect the presence of a GM-CSF antibody in a biological sample, and in the recombinant production of polypeptides of the invention. Further, the invention includes all polynucleotides that encode any polypeptide of the present invention.

In other related embodiments, the invention provides polynucleotide variants having substantial identity to the sequences to 1783J22, for example those comprising at least 70% sequence identity, preferably at least 75%, 80%, 85%, 90%, 95%, 96%, 97%, 98%, or 99% or higher, sequence identity compared to a polynucleotide sequence of this invention, as determined using the methods described herein, (e.g., BLAST analysis using standard parameters). One skilled in this art will recognize that these values can be appropriately adjusted to determine corresponding identity of proteins encoded by two nucleotide sequences by taking into account codon degeneracy, amino acid similarity, reading frame positioning, and the like.

Typically, polynucleotide variants contain one or more substitutions, additions, deletions and/or insertions, preferably such that the immunogenic binding properties of the polypeptide encoded by the variant polynucleotide is not substantially diminished relative to a polypeptide encoded by a polynucleotide sequence specifically set forth herein.

In additional embodiments, the present invention provides polynucleotide fragments comprising various lengths of contiguous stretches of sequence identical to or complementary to one or more of the sequences disclosed herein. For example, polynucleotides are provided by this invention that comprise at least about 10, 15, 20, 30, 40, 50, 75, 100, 150, 200, 300, 400, 500 or 1000 or more contiguous nucleotides of one or more of the sequences disclosed herein as well as all intermediate lengths there between. As used herein, the term "intermediate lengths" is meant to describe any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200-500; 500-1,000, and the like.

In another embodiment of the invention, polynucleotide compositions are provided that are capable of hybridizing under moderate to high stringency conditions to a polynucleotide sequence provided herein, or a fragment thereof, or a complementary sequence thereof. Hybridization techniques are well known in the art of molecular biology. For purposes of illustration, suitable moderately stringent conditions for testing the hybridization of a polynucleotide of this invention with other polynucleotides include prewashing in a solution of 5×SSC, 0.5% SDS, 1.0 mM EDTA (pH 8.0); hybridizing at 50° C.-60° C., 5×SSC, overnight; followed by washing twice at 65° C. for 20 minutes with each of 2×, 0.5× and 0.2×SSC containing 0.1% SDS. One skilled in the art will understand that the stringency of hybridization can be readily manipulated, such as by altering the salt content of the hybridization solution and/or the temperature at which the hybridization is performed. For example, in another embodiment, suitable highly stringent hybridization conditions include those described above, with the exception that the temperature of hybridization is increased, e.g., to 60-65° C. or 65-70° C.

In preferred embodiments, the polypeptide encoded by the polynucleotide variant or fragment has the same binding specificity (i.e., specifically or preferentially binds to the same GM-CSF epitope) as the polypeptide encoded by the native polynucleotide. In certain preferred embodiments, the polynucleotides described above, e.g., polynucleotide variants, fragments and hybridizing sequences, encode polypeptides that have a level of binding activity of at least about 50%, preferably at least about 70%, and more preferably at least about 90% of that for a polypeptide sequence specifically set forth herein.

The polynucleotides of the present invention, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. A nucleic acid fragment of almost any length is employed, with the total length preferably being limited by the ease of preparation and use in the intended recombinant DNA protocol. For example, illustrative polynucleotide segments with total lengths of about 10,000, about 5000, about 3000, about 2,000, about 1,000, about 500, about 200, about 100, about 50 base pairs in length, and the like, (including all intermediate lengths) are included in many implementations of this invention.

It will be appreciated by those of ordinary skill in the art that, as a result of the degeneracy of the genetic code, there are multiple nucleotide sequences that encode a polypeptide as described herein. Some of these polynucleotides bear minimal homology to the nucleotide sequence of any native gene. Nonetheless, polynucleotides that encode a polypeptide of the present invention but which vary due to differences in codon usage are specifically contemplated by the invention. Further, alleles of the genes including the polynucleotide sequences provided herein are within the scope of the invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

In certain embodiments of the present invention, mutagenesis of the disclosed polynucleotide sequences is performed in order to alter one or more properties of the encoded polypeptide, such as its binding specificity or binding strength. Techniques for mutagenesis are well-known in the art, and are widely used to create variants of both polypeptides and polynucleotides. A mutagenesis approach, such as site-specific mutagenesis, is employed for the preparation of variants and/or derivatives of the polypeptides described herein. By this approach, specific modifications in a polypeptide sequence are made through mutagenesis of the underlying polynucleotides that encode them. These techniques provides a straightforward approach to prepare and test sequence variants, for example, incorporating one or more of the foregoing considerations, by introducing one or more nucleotide sequence changes into the polynucleotide.

Site-specific mutagenesis allows the production of mutants through the use of specific oligonucleotide sequences include the nucleotide sequence of the desired mutation, as well as a sufficient number of adjacent nucleotides, to provide a primer sequence of sufficient size and sequence complexity to form a stable duplex on both sides of the deletion junction being traversed. Mutations are employed in a selected polynucleotide sequence to improve, alter, decrease, modify, or otherwise change the properties of the polynucleotide itself, and/or alter the properties, activity, composition, stability, or primary sequence of the encoded polypeptide.

In other embodiments of the present invention, the polynucleotide sequences provided herein are used as probes or primers for nucleic acid hybridization, e.g., as PCR primers. The ability of such nucleic acid probes to specifically hybridize to a sequence of interest enables them to detect the presence of complementary sequences in a given sample. However, other uses are also encompassed by the invention, such as the use of the sequence information for the preparation of mutant species primers, or primers for use in preparing other genetic constructions. As such, nucleic acid segments of the invention that include a sequence region of at least about 15 nucleotide long contiguous sequences that has the same sequence as, or is complementary to, a 15 nucleotide long contiguous sequence disclosed herein is particularly useful. Longer contiguous identical or complementary sequences, e.g., those of about 20, 30, 40, 50, 100, 200, 500, 1000

(including all intermediate lengths) including full length sequences, and all lengths in between, are also used in certain embodiments.

Polynucleotide molecules having sequence regions consisting of contiguous nucleotide stretches of 10-14, 15-20, 30, 50, or even of 100-200 nucleotides or so (including intermediate lengths as well), identical or complementary to a polynucleotide sequence disclosed herein, are particularly contemplated as hybridization probes for use in, e.g., Southern and Northern blotting, and/or primers for use in, e.g., polymerase chain reaction (PCR). The total size of fragment, as well as the size of the complementary stretch(es), ultimately depends on the intended use or application of the particular nucleic acid segment. Smaller fragments are generally used in hybridization embodiments, wherein the length of the contiguous complementary region may be varied, such as between about 15 and about 100 nucleotides, but larger contiguous complementarity stretches may be used, according to the length complementary sequences one wishes to detect.

The use of a hybridization probe of about 15-25 nucleotides in length allows the formation of a duplex molecule that is both stable and selective. Molecules having contiguous complementary sequences over stretches greater than 12 bases in length are generally preferred, though, in order to increase stability and selectivity of the hybrid, and thereby improve the quality and degree of specific hybrid molecules obtained. Nucleic acid molecules having gene-complementary stretches of 15 to 25 contiguous nucleotides, or even longer where desired, are generally preferred.

Hybridization probes are selected from any portion of any of the sequences disclosed herein. All that is required is to review the sequences set forth herein, or to any continuous portion of the sequences, from about 15-25 nucleotides in length up to and including the full length sequence, that one wishes to utilize as a probe or primer. The choice of probe and primer sequences is governed by various factors. For example, one may wish to employ primers from towards the termini of the total sequence.

Polynucleotide of the present invention, or fragments or variants thereof, are readily prepared by, for example, directly synthesizing the fragment by chemical means, as is commonly practiced using an automated oligonucleotide synthesizer. Also, fragments are obtained by application of nucleic acid reproduction technology, such as the PCR technology of U.S. Pat. No. 4,683,202, by introducing selected sequences into recombinant vectors for recombinant production, and by other recombinant DNA techniques generally known to those of skill in the art of molecular biology.

The invention provides vectors and host cells comprising a nucleic acid of the present invention, as well as recombinant techniques for the production of a polypeptide of the present invention. Vectors of the invention include those capable of replication in any type of cell or organism, including, e.g., plasmids, phage, cosmids, and mini chromosomes. In various embodiments, vectors comprising a polynucleotide of the present invention are vectors suitable for propagation or replication of the polynucleotide, or vectors suitable for expressing a polypeptide of the present invention. Such vectors are known in the art and commercially available.

Polynucleotides of the present invention are synthesized, whole or in parts that are then combined, and inserted into a vector using routine molecular and cell biology techniques, including, e.g., subcloning the polynucleotide into a linearized vector using appropriate restriction sites and restriction enzymes. Polynucleotides of the present invention are amplified by polymerase chain reaction using oligonucleotide primers complementary to each strand of the polynucleotide. These primers also include restriction enzyme cleavage sites to facilitate subcloning into a vector. The replicable vector components generally include, but are not limited to, one or more of the following: a signal sequence, an origin of replication, and one or more marker or selectable genes.

In order to express a polypeptide of the present invention, the nucleotide sequences encoding the polypeptide, or functional equivalents, are inserted into an appropriate expression vector, i.e., a vector that contains the necessary elements for the transcription and translation of the inserted coding sequence. Methods well known to those skilled in the art are used to construct expression vectors containing sequences encoding a polypeptide of interest and appropriate transcriptional and translational control elements. These methods include in vitro recombinant DNA techniques, synthetic techniques, and in vivo genetic recombination. Such techniques are described, for example, in Sambrook, J., et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York. N.Y.

A variety of expression vector/host systems are utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

Within one embodiment, the variable regions of a gene expressing a monoclonal antibody of interest are amplified from a hybridoma cell using nucleotide primers. These primers are synthesized by one of ordinary skill in the art, or may be purchased from commercially available sources (see, e.g., Stratagene® (La Jolla, Calif.), which sells primers for amplifying mouse and human variable regions. The primers are used to amplify heavy or light chain variable regions, which are then inserted into vectors such as ImmunoZAP™ H or ImmunoZAP™ L (Stratagene®), respectively. These vectors are then introduced into *E. coli*, yeast, or mammalian-based systems for expression. Large amounts of a single-chain protein containing a fusion of the $V_H$ and $V_L$ domains are produced using these methods (see Bird et al., *Science* 242:423-426 (1988)).

The "control elements" or "regulatory sequences" present in an expression vector are those non-translated regions of the vector, e.g., enhancers, promoters, 5' and 3' untranslated regions, that interact with host cellular proteins to carry out transcription and translation. Such elements may vary in their strength and specificity. Depending on the vector system and host utilized, any number of suitable transcription and translation elements, including constitutive and inducible promoters, is used.

Examples of promoters suitable for use with prokaryotic hosts include the phoa promoter, β-lactamase and lactose promoter systems, alkaline phosphatase promoter, a tryptophan (trp) promoter system, and hybrid promoters such as the tac promoter. However, other known bacterial promoters are suitable. Promoters for use in bacterial systems also usually contain a Shine-Dalgarno sequence operably linked to the DNA encoding the polypeptide. Inducible promoters such as the hybrid lacZ promoter of the PBLUESCRIPT® phagemid (Stratagene®, La Jolla, Calif.) or PSPORT1 plasmid (Gibco® BRL, Gaithersburg, Md.) and the like are used.

A variety of promoter sequences are known for eukaryotes and any are used according to the present invention. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

In mammalian cell systems, promoters from mammalian genes or from mammalian viruses are generally preferred. Polypeptide expression from vectors in mammalian host cells are controlled, for example, by promoters obtained from the genomes of viruses such as polyoma virus, fowlpox virus, adenovirus (e.g., Adenovirus 2), bovine papilloma virus, avian sarcoma virus, cytomegalovirus (CMV), a retrovirus, hepatitis-B virus and most preferably Simian Virus 40 (SV40), from heterologous mammalian promoters, e.g., the actin promoter or an immunoglobulin promoter, and from heat-shock promoters, provided such promoters are compatible with the host cell systems. If it is necessary to generate a cell line that contains multiple copies of the sequence encoding a polypeptide, vectors based on SV40 or EBV may be advantageously used with an appropriate selectable marker. One example of a suitable expression vector is pcDNA-3.1 (Invitrogen™, Carlsbad, Calif.), which includes a CMV promoter.

A number of viral-based expression systems are available for mammalian expression of polypeptides. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus that is capable of expressing the polypeptide in infected host cells (Logan, J. and Shenk, T. (1984) Proc. Natl. Acad. Sci. 81:3655-3659). In addition, transcription enhancers, such as the Rous sarcoma virus (RSV) enhancer, may be used to increase expression in mammalian host cells.

In bacterial systems, any of a number of expression vectors are selected depending upon the use intended for the expressed polypeptide. For example, when large quantities are desired, vectors that direct high level expression of fusion proteins that are readily purified are used. Such vectors include, but are not limited to, the multifunctional *E. coli* cloning and expression vectors such as BLUESCRIPT® (Stratagene®), in which the sequence encoding the polypeptide of interest may be ligated into the vector in frame with sequences for the amino-terminal Met and the subsequent 7 residues of β-galactosidase, so that a hybrid protein is produced; pIN vectors (Van Heeke, G. and S. M. Schuster (1989) J. Biol. Chem. 264:5503-5509); and the like. pGEX Vectors (Promega®, Madison, Wis.) are also used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH are used. Examples of other suitable promoter sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. For reviews, see Ausubel et al. (supra) and Grant et al. (1987) Methods Enzymol. 153:516-544. Other yeast promoters that are inducible promoters having the additional advantage of transcription controlled by growth conditions include the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

In cases where plant expression vectors are used, the expression of sequences encoding polypeptides are driven by any of a number of promoters. For example, viral promoters such as the 35S and 19S promoters of CaMV are used alone or in combination with the omega leader sequence from TMV (Takamatsu, N. (1987) *EMBO J.* 6:307-311. Alternatively, plant promoters such as the small subunit of RUBISCO or heat shock promoters are used (Coruzzi, G. et al. (1984) EMBO J. 3:1671-1680; Broglie, R. et al. (1984) Science 224:838-843; and Winter, J., et al. (1991) Results Probl. Cell Differ. 17:85-105). These constructs can be introduced into plant cells by direct DNA transformation or pathogen-mediated transfection. Such techniques are described in a number of generally available reviews (see, e.g., Hobbs, S. or Murry, L. E. in McGraw Hill Yearbook of Science and Technology (1992) McGraw Hill, New York, N.Y.; pp. 191-196).

An insect system is also used to express a polypeptide of interest. For example, in one such system, *Autographa californica* nuclear polyhedrosis virus (AcNPV) is used as a vector to express foreign genes in *Spodoptera frugiperda* cells or in *Trichoplusia* larvae. The sequences encoding the polypeptide are cloned into a non-essential region of the virus, such as the polyhedrin gene, and placed under control of the polyhedrin promoter. Successful insertion of the polypeptide-encoding sequence renders the polyhedrin gene inactive and produce recombinant virus lacking coat protein. The recombinant viruses are then used to infect, for example, *S. frugiperda* cells or *Trichoplusia* larvae, in which the polypeptide of interest is expressed (Engelhard, E. K. et al. (1994) Proc. Natl. Acad. Sci. 91: 3224-3227).

Specific initiation signals are also used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon are provided. Furthermore, the initiation codon is in the correct reading frame to ensure correct translation of the inserted polynucleotide. Exogenous translational elements and initiation codons are of various origins, both natural and synthetic.

Transcription of a DNA encoding a polypeptide of the invention is often increased by inserting an enhancer sequence into the vector. Many enhancer sequences are known, including, e.g., those identified in genes encoding globin, elastase, albumin, α-fetoprotein, and insulin. Typically, however, an enhancer from a eukaryotic cell virus is used. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer is spliced into the vector at a position 5' or 3' to the polypeptide-encoding sequence, but is preferably located at a site 5' from the promoter.

Expression vectors used in eukaryotic host cells (yeast, fungi, insect, plant, animal, human, or nucleated cells from other multicellular organisms) typically also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding anti-PSCA antibody. One useful transcription termination component is the bovine growth hormone polyadenylation region. See WO94/11026 and the expression vector disclosed therein.

Suitable host cells for cloning or expressing the DNA in the vectors herein are the prokaryote, yeast, plant or higher eukaryote cells described above. Examples of suitable prokaryotes for this purpose include eubacteria, such as Gram-negative or Gram-positive organisms, for example, *Enterobacteriaceae* such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

*Saccharomyces cerevisiae*, or common baker's yeast, is the most commonly used among lower eukaryotic host microorganisms. However, a number of other genera, species, and strains are commonly available and used herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris*. (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

In certain embodiments, a host cell strain is chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing that cleaves a "prepro" form of the protein is also used to facilitate correct insertion, folding and/or function. Different host cells such as CHO, COS, HeLa, MDCK, HEK293, and WI38, which have specific cellular machinery and characteristic mechanisms for such post-translational activities, are chosen to ensure the correct modification and processing of the foreign protein.

Methods and reagents specifically adapted for the expression of antibodies or fragments thereof are also known and available in the art, including those described, e.g., in U.S. Pat. Nos. 4,816,567 and 6,331,415. In various embodiments, antibody heavy and light chains, or fragments thereof, are expressed from the same or separate expression vectors. In one embodiment, both chains are expressed in the same cell, thereby facilitating the formation of a functional antibody or fragment thereof.

Full length antibody, antibody fragments, and antibody fusion proteins are produced in bacteria, in particular when glycosylation and Fc effector function are not needed, such as when the therapeutic antibody is conjugated to a cytotoxic agent (e.g., a toxin) and the immunoconjugate by itself shows effectiveness in infected cell destruction. For expression of antibody fragments and polypeptides in bacteria, see, e.g., U.S. Pat. Nos. 5,648,237, 5,789,199, and 5,840,523, which describes translation initiation region (TIR) and signal sequences for optimizing expression and secretion. After expression, the antibody is isolated from the *E. coli* cell paste in a soluble fraction and can be purified through, e.g., a protein A or G column depending on the isotype. Final purification can be carried out using a process similar to that used for purifying antibody expressed e.g., in CHO cells.

Suitable host cells for the expression of glycosylated polypeptides and antibodies are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopicius* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses are used as the virus herein according to the present invention, particularly for transfection of *Spodoptera frugiperda* cells. Plant cell cultures of cotton, corn, potato, soybean, petunia, tomato, and tobacco are also utilized as hosts.

Methods of propagation of antibody polypeptides and fragments thereof in vertebrate cells in culture (tissue culture) are encompassed by the invention. Examples of mammalian host cell lines used in the methods of the invention are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., Annals N.Y. Acad. Sci. 383:44-68 (1982)); MRC 5 cells; FS4 cells; and a human hepatoma line (Hep G2).

Host cells are transformed with the above-described expression or cloning vectors for polypeptide production and cultured in conventional nutrient media modified as appropriate for inducing promoters, selecting transformants, or amplifying the genes encoding the desired sequences.

For long-term, high-yield production of recombinant proteins, stable expression is generally preferred. For example, cell lines that stably express a polynucleotide of interest are transformed using expression vectors that contain viral origins of replication and/or endogenous expression elements and a selectable marker gene on the same or on a separate vector. Following the introduction of the vector, cells are allowed to grow for 1-2 days in an enriched media before they are switched to selective media. The purpose of the selectable marker is to confer resistance to selection, and its presence allows growth and recovery of cells that successfully express the introduced sequences. Resistant clones of stably transformed cells are proliferated using tissue culture techniques appropriate to the cell type.

A plurality of selection systems are used to recover transformed cell lines. These include, but are not limited to, the herpes simplex virus thymidine kinase (Wigler, M. et al. (1977) *Cell* 11:223-32) and adenine phosphoribosyltransferase (Lowy, I. et al. (1990) Cell 22:817-23) genes that are employed in tk$^-$ or aprt$^-$ cells, respectively. Also, antimetabolite, antibiotic or herbicide resistance is used as the basis for selection; for example, dhfr, which confers resistance to methotrexate (Wigler, M. et al. (1980) *Proc. Natl. Acad. Sci.* 77:3567-70); npt, which confers resistance to the aminoglycosides, neomycin and G-418 (Colbere-Garapin, F. et al. (1981) *J. Mol. Biol.* 150:1-14); and als or pat, which confer resistance to chlorsulfuron and phosphinotricin acetyltransferase, respectively (Murry, supra). Additional selectable genes have been described. For example, trpB allows cells to utilize indole in place of tryptophan, and hisD allows cells to utilize histinol in place of histidine (Hartman, S. C. and R. C. Mulligan (1988) *Proc. Natl. Acad. Sci.* 85:8047-51). The use of visible markers has gained popularity with such markers as anthocyanins, beta-glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) *Methods Mol. Biol.* 55:121-131).

Although the presence/absence of marker gene expression suggests that the gene of interest is also present, its presence and expression is confirmed. For example, if the sequence encoding a polypeptide is inserted within a marker gene sequence, recombinant cells containing sequences are identified by the absence of marker gene function. Alternatively, a marker gene is placed in tandem with a polypeptide-encoding sequence under the control of a single promoter. Expression of the marker gene in response to induction or selection usually indicates expression of the tandem gene as well.

Alternatively, host cells that contain and express a desired polynucleotide sequence are identified by a variety of procedures known to those of skill in the art. These procedures include, but are not limited to, DNA-DNA or DNA-RNA hybridizations and protein bioassay or immunoassay techniques which include, for example, membrane, solution, or chip based technologies for the detection and/or quantification of nucleic acid or protein.

A variety of protocols for detecting and measuring the expression of polynucleotide-encoded products, using either polyclonal or monoclonal antibodies specific for the product are known in the art. Nonlimiting examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on a given polypeptide is preferred for some applications, but a competitive binding assay may also be employed. These and other assays are described, among other places, in Hampton, R. et al. (1990; Serological Methods, a Laboratory Manual, APS Press, St Paul. Minn.) and Maddox, D. E. et al. (1983; J. Exp. Med. 158:1211-1216).

Various labels and conjugation techniques are known by those skilled in the art and are used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof are cloned into a vector for the production of an mRNA probe. Such vectors are known in the art, are commercially available, and are used to synthesize RNA probes in vitro by addition of an appropriate RNA polymerase such as T7, T3, or SP6 and labeled nucleotides. These procedures are conducted using a variety of commercially available kits. Suitable reporter molecules or labels, which are used include, but are not limited to, radionuclides, enzymes, fluorescent, chemiluminescent, or chromogenic agents as well as substrates, cofactors, inhibitors, magnetic particles, and the like.

The polypeptide produced by a recombinant cell is secreted or contained intracellularly depending on the sequence and/or the vector used. Expression vectors containing polynucleotides of the invention are designed to contain signal sequences that direct secretion of the encoded polypeptide through a prokaryotic or eukaryotic cell membrane.

In certain embodiments, a polypeptide of the invention is produced as a fusion polypeptide further including a polypeptide domain that facilitates purification of soluble proteins. Such purification-facilitating domains include, but are not limited to, metal chelating peptides such as histidine-tryptophan modules that allow purification on immobilized metals, protein A domains that allow purification on immobilized immunoglobulin, and the domain utilized in the FLAGS® extension/affinity purification system (Amgen™, Seattle, Wash.). The inclusion of cleavable linker sequences such as those specific for Factor XA or enterokinase (Invitrogen™, San Diego, Calif.) between the purification domain and the encoded polypeptide are used to facilitate purification. An exemplary expression vector provides for expression of a fusion protein containing a polypeptide of interest and a nucleic acid encoding 6 histidine residues preceding a thioredoxin or an enterokinase cleavage site. The histidine residues facilitate purification on IMIAC (immobilized metal ion affinity chromatography) as described in Porath, J. et al. (1992, Prot. Exp. Purif. 3:263-281) while the enterokinase cleavage site provides a means for purifying the desired polypeptide from the fusion protein. A discussion of vectors used for producing fusion proteins is provided in Kroll, D. J. et al. (1993; *DNA Cell Biol.* 12:441-453).

In certain embodiments, a polypeptide of the present invention is fused with a heterologous polypeptide, which may be a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells, the signal sequence is selected, for example, from the group of the alkaline phosphatase, penicillinase, 1pp, or heat-stable enterotoxin II leaders. For yeast secretion, the signal sequence is selected from, e.g., the yeast invertase leader, α factor leader (including *Saccharomyces* and *Kluyveromyces* α factor leaders), or acid phosphatase leader, the *C. albicans* glucoamylase leader, or the signal described in WO 90/13646. In mammalian cell expression, mammalian signal sequences as well as viral secretory leaders, for example, the herpes simplex gD signal, are available.

When using recombinant techniques, the polypeptide or antibody is produced intracellularly, in the periplasmic space, or directly secreted into the medium. If the polypeptide or antibody is produced intracellularly, as a first step, the particulate debris, either host cells or lysed fragments, are removed, for example, by centrifugation or ultrafiltration. Carter et al., Bio/Technology 10:163-167 (1992) describe a procedure for isolating antibodies that are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris is removed by centrifugation. Where the polypeptide or antibody is secreted into the medium, supernatants from such expression systems are generally first concentrated using a commercially available protein concentration filter, for example, an Amicon® or Millipore® Pellicon® ultrafiltration unit. Optionally, a protease inhibitor such as PMSF is included in any of the foregoing steps to inhibit proteolysis and antibiotics are included to prevent the growth of adventitious contaminants.

The polypeptide or antibody composition prepared from the cells are purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the polypeptide or antibody. Protein A is used to purify antibodies or fragments thereof that are based on human $\gamma_1$, $\gamma_2$, or $\gamma_4$ heavy chains (Lindmark et al., J. Immunol. Meth. 62:1-13 (1983)). Protein G is recommended for all mouse isotypes and for human $\gamma_3$ (Guss et al., EMBO J. 5:15671575 (1986)). The matrix to which the affinity ligand is attached is most often agarose, but other matrices are available. Mechanically stable matrices such as controlled pore glass or poly(styrenedivinyl) benzene allow for faster flow rates and shorter processing times than can be achieved with agarose. Where the polypeptide or antibody comprises a $C_H 3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the polypeptide or antibody to be recovered.

Following any preliminary purification step(s), the mixture comprising the polypeptide or antibody of interest and contaminants are subjected to low pH hydrophobic interaction chromatography using an elution buffer at a pH between about 2.5-4.5, preferably performed at low salt concentrations (e.g., from about 0-0.25M salt).

Compositions of the invention further includes pharmaceutical formulations including a polypeptide, antibody, or modulator of the present invention, at a desired degree of purity, and a pharmaceutically acceptable carrier, excipient, or stabilizer (Remingion's Pharmaceutical Sciences 16th edition, Osol, A. Ed. (1980)). In certain embodiments, pharmaceutical formulations are prepared to enhance the stability of the polypeptide or antibody during storage, e.g., in the form of lyophilized formulations or aqueous solutions.

The pharmaceutical compositions of antibodies of the invention may be used to treat a disease, for example, cancer, an infectious disease, or an inflammatory disease in a patient. In prophylactic applications, pharmaceutical compositions are administered to a patient susceptible to, or otherwise at risk of a disease or condition (e.g., cancer, an infectious disease, or an inflammatory disease) in a prophylactically effective amount. At-risk individuals include, but are not limited to, individuals with a family history of cancer, an infectious disease, or an inflammatory disease, individuals who have previously been treated for cancer, an infectious disease, or an inflammatory disease, and individuals presenting any other clinical indicia suggesting that they have an increased likelihood of developing cancer, an infectious disease, or an inflammatory disease. Alternatively stated, an at-risk individual is any individual who is believed to be at a higher risk than the general population for developing cancer, an infectious disease, or an inflammatory disease. The term "prophylactically effective amount" is meant to refer to an amount of a formulation which produces an effect observed as the prevention of the onset or recurrence of cancer, an infectious disease, or an inflammatory disease. Prophylactically effective amounts of a formulation are typically determined by the effect they have compared to the effect observed when a second formulation lacking the active agent is administered to a similarly situated individual.

In therapeutic applications, compositions are administered to a patient suspected of, or already suffering from such a disease in a therapeutically effective amount sufficient to cure, or at least partially arrest, the symptoms of the disease (biochemical and/or histological), including its complications and intermediate pathological phenotypes in development of the disease.

In both prophylactic and therapeutic regimes, agents are usually administered in several dosages until a sufficient response has been achieved. Typically, the response is monitored and repeated dosages are given if the response starts to wane. Effective doses of a monoclonal antibody for the treatment of disease, e.g., cancer, an infectious disease, or an inflammatory disease, as described herein, vary depending upon many different factors, including means of administration, target site, physiological state of the patient, whether the patient is human or an animal, other medications administered, and whether treatment is prophylactic or therapeutic. Usually, the patient is a human but nonhuman mammals can also be treated.

The invention provides pharmaceutical compositions comprising one or more MAbs for the treatment of disease, such as but not limited to cancer, an infectious disease, or an inflammatory disease, formulated together with a pharmaceutically acceptable carrier. Acceptable carriers, excipients, or stabilizers are nontoxic to recipients at the dosages and concentrations employed, and include, e.g., buffers such as acetate, Tris, phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; tonicifiers such as trehalose and sodium chloride; sugars such as sucrose, mannitol, trehalose or sorbitol; surfactant such as polysorbate; salt-forming counter-ions such as sodium; metal complexes (e.g. Zn-protein complexes); and/or non-ionic surfactants such as TWEEN™, PLURONICS™ or polyethylene glycol (PEG).

In certain embodiments, the therapeutic formulation preferably comprises the polypeptide or antibody at a concentration of between 5-200 mg/ml, preferably between 10-100 mg/ml.

The compositions of the invention also contain one or more additional therapeutic agents suitable for the treatment of the particular indication, e.g., infection being treated, or to prevent undesired side-effects. Preferably, the additional therapeutic agent has an activity complementary to the polypeptide or antibody of the resent invention, and the two do not adversely affect each other. For example, in addition to the polypeptide or antibody of the invention, an additional or second antibody, anti-viral agent, anti-infective agent and/or cardioprotectant is added to the formulation. Such molecules are suitably present in the pharmaceutical formulation in amounts that are effective for the purpose intended.

The active ingredients, e.g., polypeptides and antibodies of the invention and other therapeutic agents, are also entrapped in microcapsules prepared, for example, by coacervation techniques or by interfacial polymerization, for example, hydroxymethylcellulose or gelatin-microcapsules and poly-methylmethacylate) microcapsules, respectively, in colloidal drug delivery systems (for example, liposomes, albumin microspheres, microemulsions, nano-particles and nanocapsules) or in macroemulsions. Such techniques are disclosed in Remingion's Pharmaceutical Sciences 16th edition, Osol, A. Ed. (1980).

Sustained-release preparations are prepared. Suitable examples of sustained-release preparations include, but are not limited to, semi-permeable matrices of solid hydrophobic polymers containing the antibody, which matrices are in the form of shaped articles, e.g., films, or microcapsules. Non-limiting examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxyburyric acid.

Compositions or formulations to be used for in vivo administration are preferably sterile. This is readily accomplished by filtration through sterile filtration membranes.

Antibodies of the invention can be coupled to a drug for delivery to a treatment site or coupled to a detectable label to facilitate imaging of a site comprising cells of interest. Methods for coupling antibodies to drugs and detectable labels are well known in the art, as are methods for imaging using detectable labels. Labeled antibodies may be employed in a wide variety of assays, employing a wide variety of labels. Detection of the formation of an antibody-antigen complex between an antibody of the invention and an epitope of interest (GM-CSF epitope) can be facilitated by attaching a detectable substance to the antibody. Suitable detection means include the use of labels such as radionucleotides, enzymes, coenzymes, fluorescers, chemiluminescers, chromogens, enzyme substrates or co-factors, enzyme inhibitors, prosthetic group complexes, free radicals, particles, dyes, and the like. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material is luminol; examples of bioluminescent materials include luciferase, luciferin, and aequorin; and examples of suitable radioactive material include $^{125}I$, $^{131}I$, $^{35}S$, or $^{3}H$. Such labeled reagents may be used in a variety of well-known assays, such as radioimmunoassays, enzyme immunoassays, e.g., ELISA, fluorescent immunoassays, and the like.

The antibodies are tagged with such labels by known methods. For instance, coupling agents such as aldehydes, carbodiimides, dimaleimide, imidates, succinimides, bid-diazotized benzandine and the like are used to tag the antibodies with the above-described fluorescent, chemiluminescent, and enzyme labels. An enzyme is typically combined with an antibody using bridging molecules such as carbodiimides, periodate, diisocyanates, glutaraldehyde and the like. Various labeling techniques are described in Morrison, Methods in Enzymology 32b, 103 (1974), Syvanen et al., J. Biol. Chem. 284, 3762 (1973) and Bolton and Hunter, Biochem J. 133, 529(1973).

An antibody according to the invention may be conjugated to a therapeutic moiety such as a cytotoxin, a therapeutic agent, or a radioactive metal ion or radioisotope. Examples of radioisotopes include, but are not limited to, I-131, I-123, I-125, Y-90, Re-188, Re-186, At-211, Cu-67, Bi-212, Bi-213, Pd-109, Tc-99, In-111, and the like. Such antibody conjugates can be used for modifying a given biological response; the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin.

Techniques for conjugating such therapeutic moiety to antibodies are well known. See, for example, Arnon et al. (1985) "Monoclonal Antibodies for Immunotargeting of Drugs in Cancer Therapy," in Monoclonal Antibodies and Cancer Therapy, ed. Reisfeld et al. (Alan R. Liss, Inc.), pp. 243-256; ed. Hellstrom et al. (1987) "Antibodies for Drug Delivery," in Controlled Drug Delivery, ed. Robinson et al. (2d ed; Marcel Dekker, Inc.), pp. 623-653; Thorpe (1985) "Antibody Carriers of Cytotoxic Agents in Cancer Therapy: A Review," in Monoclonal Antibodies '84: Biological and Clinical Applications, ed. Pinchera et al. pp. 475-506 (Editrice Kurds, Milano, Italy, 1985); "Analysis, Results, and Future Prospective of the Therapeutic Use of Radiolabeled Antibody in Cancer Therapy," in Monoclonal Antibodies for Cancer Detection and Therapy, ed. Baldwin et al. (Academic Press, New York, 1985), pp. 303-316; and Thorpe et al. (1982) Immunol. Rev. 62:119-158.

Diagnostic methods generally involve contacting a biological sample obtained from a patient, such as, e.g., blood, serum, saliva, urine, sputum, a cell swab sample, or a tissue biopsy, with a GM-CSF antibody and determining whether the antibody preferentially binds to the sample as compared to a control sample or predetermined cut-off value, thereby indicating the level of GM-CSF in the cells. In particular embodiments, at least two-fold, three-fold, or five-fold more GM-CSF antibody binds to a target cell as compared to an appropriate control normal cell or tissue sample. A pre-determined cut-off value is determined, e.g., by averaging the amount of GM-CSF antibody that binds to several different appropriate control samples under the same conditions used to perform the diagnostic assay of the biological sample being tested.

Bound antibody is detected using procedures described herein and known in the art. In certain embodiments, diagnostic methods of the invention are practiced using GM-CSF antibodies that are conjugated to a detectable label, e.g., a fluorophore, to facilitate detection of bound antibody. However, they are also practiced using methods of secondary detection of the GM-CSF antibody. These include, for example, RIA, ELISA, precipitation, agglutination, complement fixation and immunofluorescence.

The present invention also includes kits useful for the treatment of cancer, an infectious disease, an autoimmune disease, or an inflammatory disease in performing diagnostic and prognostic assays using the antibodies of the present invention. The kits of the invention comprise antibody or an antibody composition of the invention and instructions for using the kit in a method for treating cancer, an infectious disease, or an inflammatory disease in a patient or for inhibiting the biological activity of target antigen (e.g., GM-CSF). The kit may comprise at least one supplemental compound. Kits of the invention include a suitable container comprising a GM-CSF antibody of the invention in either labeled or unlabeled form. In addition, when the antibody is supplied in a labeled form suitable for an indirect binding assay, the kit further includes reagents for performing the appropriate indirect assay. For example, the kit includes one or more suitable containers including enzyme substrates or derivatizing agents, depending on the nature of the label. Control samples and/or instructions and/or means for administering the antibody or antibody composition are also included.

In various embodiments, antibodies of the invention are intrinsically therapeutically active. Alternatively, or in addition, antibodies of the invention are conjugated to a cytotoxic agent or growth inhibitory agent, e.g., a radioisotope or toxin, that is used in treating infected cells bound or contacted by the antibody. Therapeutic methods of the invention include methods of inhibiting the biological activity of a target antigen, for example, GM-CSF and methods of treating a disease such as but not limited to cancer, an infectious disease, an autoimmune disease or an inflammatory disease by administering the pharmaceutical compositions of the antibodies of the invention to a patient or subject in need thereof. Biological activity of GM-CSF includes but is not limited to binding to the GM-CSF receptor. The methods may be employed, for example, to effect prophylactic or therapeutic treatment of a disease.

For in vivo treatment of human and non-human patients, the patient is usually administered or provided a pharmaceutical formulation including a GM-CSF antibody of the invention. When used for in vivo therapy, the antibodies of the invention are administered to the patient in therapeutically effective amounts (i.e., amounts that eliminate or reduce the patient's viral burden). The antibodies are administered to a human patient, in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. The antibodies may be administered parenterally, when possible, at the target cell site, or intravenously. Intravenous or subcutaneous administration of the antibody is preferred in certain embodiments. Therapeutic compositions of the invention are administered to a patient or subject systemically, parenterally, or locally.

For parenteral administration, the antibodies are formulated in a unit dosage injectable form (solution, suspension, emulsion) in association with a pharmaceutically acceptable, parenteral vehicle. Examples of such vehicles are water, saline, Ringer's solution, dextrose solution, and 5% human serum albumin. Nonaqueous vehicles such as fixed oils and ethyl oleate are also used. Liposomes are used as carriers. The vehicle contains minor amounts of additives such as substances that enhance isotonicity and chemical stability, e.g., buffers and preservatives. The antibodies are typically formulated in such vehicles at concentrations of about 1 mg/ml to 10 mg/ml.

Effective doses of a monoclonal antibody for the treatment of disease, e.g., cancer, an infectious disease, or an inflammatory disease, or an autoimmune disease as described herein, vary depending upon many different factors, including means of administration, target site, physiological state of the patient, whether the patient is human or an animal, other medications administered, and whether treatment is prophylactic or therapeutic. The dose and dosage regimen depends upon a variety of factors readily determined by a physician, such as the nature of the infection and the characteristics of the particular cytotoxic agent or growth inhibitory agent conjugated to the antibody (when used), e.g., its therapeutic index, the patient, and the patient's history. Generally, a therapeutically effective amount of an antibody is administered to a patient. In general, dosage is from 0.01 µg to 100 g per kg of body weight and can be given once or more daily, weekly, monthly or yearly. In particular embodiments, the amount of antibody administered is in the range of about 0.1 mg/kg to about 50 mg/kg of patient body weight. Depending on the type and severity of the infection, about 0.1 mg/kg to about 50 mg/kg body weight (e.g., about 0.1-15 mg/kg/dose) of antibody is an initial candidate dosage for administration to the patient, whether, for example, by one or more separate administrations, or by continuous infusion. Optimum dosages can vary depending on the relative potency of individual antibodies and, in the case of concomitant administration, the relative potency of known drugs used in the treatment of disease. Optimum dosages can generally be estimated based on $EC_{50}$ found to be effective in in vitro and in vivo animal models. The progress of this therapy is readily monitored by conventional methods and assays and based on criteria known to the physician or other persons of skill in the art.

In one particular embodiment, an immunoconjugate including the antibody conjugated with a cytotoxic agent is administered to the patient. Preferably, the immunoconjugate is internalized by the cell, resulting in increased therapeutic efficacy of the immunoconjugate in killing the cell to which it binds. In one embodiment, the cytotoxic agent targets or interferes with the nucleic acid in the infected cell. Examples of such cytotoxic agents are described above and include, but are not limited to, maytansinoids, calicheamicins, ribonucleases and DNA endonucleases.

Other therapeutic regimens are combined with the administration of the GM-CSF antibody of the present invention. The combined administration includes co-administration, using separate formulations or a single pharmaceutical formulation, and consecutive administration in either order, wherein preferably there is a time period while both (or all) active agents simultaneously exert their biological activities. Preferably such combined therapy results in a synergistic therapeutic effect.

In certain embodiments, it is desirable to combine administration of an antibody of the invention with another antibody directed against another antigen associated with the infectious agent.

Aside from administration of the antibody protein to the patient, the invention provides methods of administration of the antibody by gene therapy. Such administration of nucleic acid encoding the antibody is encompassed by the expression "administering a therapeutically effective amount of an antibody". See, for example, PCT Patent Application Publication WO96/07321 concerning the use of gene therapy to generate intracellular antibodies.

In another embodiment, anti-GM-CSF antibodies of the invention are used to determine the structure of bound antigen, e.g., conformational epitopes, the structure of which is then used to develop a vaccine having or mimicking this structure, e.g., through chemical modeling and SAR methods. Such a vaccine could then be used for prevention or prophylaxis of GM-CSF related diseases and conditions.

Definitions

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., Sambrook, et al. Molecular Cloning: A Laboratory Manual (2nd Edition, 1989); Maniatis et al. Molecular Cloning: A Laboratory Manual (1982); DNA Cloning: A Practical Approach, vol. I & II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Animal Cell Culture (R. Freshney, ed., 1986); Perbal, A Practical Guide to Molecular Cloning (1984).

The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

The following definitions are useful in understanding the present invention:

It is to be understood that this invention is not limited to particular methods, reagents, compounds, compositions or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a cell" includes a combination of two or more cells, and the like.

Each range recited herein includes all combinations and sub-combinations of ranges, as well as specific numerals contained therein. The term "about" as used herein when referring to a measurable value such as an amount, a temporal duration, and the like, is meant to encompass variations of ±20% or 10%, or ±5%, or ±%, or ±0.1% from the specified value, as such variations are appropriate to perform the disclosed methods.

"GM-CSF" comprises a family of glycoprotein growth factors that control the production, differentiation and function of granulocytes and monocytes-macrophages. GM-CSF encompasses any protein encoded by a nucleic acid that codes for GM-CSF. (Cantrell et al. (September 1985) Proc. Natl. Acad. Sci., USA 82: 6250-6254; Wong et al. (May 1985) Science 228:810-815.)

"Infectious disease" includes, but is not limited to, infection with a pathogen, a virus, a bacterium, a fungus or a parasite. Infectious diseases include, or are caused by infection with, sepsis, severe acute respiratory syndrome (SARS; caused by SARS-associated coronavirus), hepatitis type B or type C, influenza, varicella, adenovirus, herpes simplex virus type I or type II, rinderpest, rhinovirus, echovirus, rotavirus, respiratory syncytial virus, papilloma virus, papova virus, cytomegalovirus, echinovirus, arbovirus, hantavirus, coxsachie virus, mumps virus, measles virus, rubella virus, polio virus, human immunodeficiency virus (HIV) type I or type II, Meningitis, Septic arthritis, Peritonitis, Pneumonia, Epiglottitis, *E. coli*, Hemolytic uremic syndrome, thrombocytopenia, to, Ebola, *Staphylococcus* A-E, Plasmodium, Malaria, Dengue, hemorrhagic fever, Leishmaniasis, Leprosy, Toxic shock syndrome, Streptococcal myositis, Gas gangrene, *Mycobacterium, Pneumocystis*, Pelvic inflammatory disease, Orchitis/epidydimitis, *Legionella*, Lyme disease Influenza A, Epstein-Barr Virus, Viral associated hemiaphagocytic syndrome, viral encephalitis, aseptic meningitis, mycoplasma, neisseria, legionella, rickettsia or Chlamydia.

"Inflammatory diseases" include, but are not limited to, inflammatory-mediated conditions or diseases such as, asthma, acute inflammation, chronic inflammation, type I diabetes or type II diabetes and all of the related pathologies, rheumatoid arthritis, autoimmune disease, inflammatory renal disease and inflammatory lung disorders such as asthma and chronic obstructive pulmonary disease (COPD), multiple sclerosis, and autoimmune encephalomyelitis. An inflammatory disease may also be a cancer including, but not limited to, colon cancer, lung cancer, breast cancer, pancreatic cancer, leukemia, or juvenile myelomonocytic leukemia (JML).

An "autoimmune disease" includes, but is not limited to, rheumatoid arthritis, osteoarthritis, juvenile chronic arthritis, Lyme arthritis, psoriatic arthritis, reactive arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, dermatitis scleroderma, atopic dermatitis, graft versus host disease, organ transplant rejection, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein purpurea, microscopic vasculitis of the kidneys, chronic active hepatitis, uveitis, septic shock, toxic shock syndrome, sepsis syndrome, cachexia, infectious diseases, parasitic diseases, acquired immunodeficiency syndrome, acute transverse myelitis, Huntington's chorea, Parkinson's disease, Alzheimer's disease, stroke, primary biliary cirrhosis, hemolytic anemia, malignancies, heart failure, myocardial infarction, Addison's disease, sporadic, polyglandular deficiency type I and polyglandular deficiency type II, Schmidt's syndrome, adult (acute) respiratory distress syndrome, alopecia, alopecia greata, seronegative arthopathy, arthropathy, Reiter's disease, psoriatic arthropathy, ulcerative colitic arthropathy, enteropathic synovitis, chlamydia, yersinia and salmonella associated arthropathy, spondyloarthopathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis C, common varied immunodeficiency (common variable hypogammaglobulinaemia), dilated cardiomyopathy, female infertility, ovarian failure, premature ovarian failure, fibrotic lung disease, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjogren's disease associated lung disease, ankylosing spondylitis associated lung disease, vasculitic diffuse lung disease, haemosiderosis associated lung disease, drug-induced interstitial lung disease, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycemia, type B insulin resistance with acanthosis nigricans, hypoparathyroidism, acute immune disease associated with organ transplantation, chronic immune disease associated with organ transplantation, osteoarthrosis, primary sclerosing cholangitis, idiopathic leucopenia, autoimmune neutropenia, renal disease NOS, glomerulonephritides, microscopic vasulitis of the kidneys, lyme disease, discoid lupus erythematosus, male infertility idiopathic or NOS, sperm autoimmunity, multiple sclerosis (all subtypes), insulin-dependent diabetes mellitus, sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Takayasu's disease/arteritis, autoimmune thrombocytopenia, idiopathic thrombocytopenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis and vitiligo. The human antibodies, and antibody portions of the invention can be used to treat autoimmune diseases, in particular those associated with inflammation, including, rheumatoid spondylitis, allergy, autoimmune diabetes, autoimmune uveitis.

Preferably, the antibodies of the invention or antigen-binding portions thereof, are used to treat rheumatoid arthritis, Crohn's disease, multiple sclerosis, insulin dependent diabetes mellitus and psoriasis. A human antibody, or antibody portion, of the invention also can be administered with one or more additional therapeutic agents useful in the treatment of autoimmune and inflammatory diseases.

The term "antibody" (Ab) as used herein includes monoclonal antibodies, polyclonal antibodies, multispecific antibodies (e.g., bispecific antibodies), and antibody fragments, so long as they exhibit the desired biological activity. The term "immunoglobulin" (Ig) is used interchangeably with "antibody" herein.

A "neutralizing antibody" may inhibit the activity of GM-CSF with a neutralization index >1.5 or >2.0. The inhibitory concentration of the monoclonal antibody may be less than about 25 mg/ml to neutralize about 50% of the input GM-CSF in the neutralization assay.

An "isolated antibody" is one that has been separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In preferred embodiments, the antibody is purified: (1) to greater than 95% by weight of antibody as determined by the Lowry method, and most preferably more than 99% by weight; (2) to a degree sufficient to obtain at least 15 residues of N-terminal or internal amino acid sequence by use of a spinning cup sequenator; or (3) to homogeneity by SDS-PAGE under reducing or non-reducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The basic four-chain antibody unit is a heterotetrameric glycoprotein composed of two identical light (L) chains and two identical heavy (H) chains. An IgM antibody consists of 5 basic heterotetramer units along with an additional polypeptide called J chain, and therefore contain 10 antigen binding sites, while secreted IgA antibodies can polymerize to form polyvalent assemblages comprising 2-5 of the basic 4-chain units along with J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain ($C_L$) at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see, e.g., Basic and Clinical Immunology, 8th edition, Daniel P. Stites, Abba I. Ten and Tristram G. Parslow (eds.), Appleton & Lange, Norwalk, Conn., 1994, page 71, and Chapter 6.

The L chain from any vertebrate species can be assigned to one of two clearly distinct types, called kappa (κ) and lambda (λ), based on the amino acid sequences of their constant domains ($C_L$). Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated alpha (α), delta (δ), epsilon (ε), gamma (γ) and mu (μ), respectively. The γ and α classes are further divided into subclasses on the basis of relatively minor differences in $C_H$ sequence and function, e.g., humans express the following subclasses: IgG1, IgG2, IgG3, IgG4, IgA1, and IgA2.

The term "variable" refers to the fact that certain segments of the V domains differ extensively in sequence among antibodies. The V domain mediates antigen binding and defines specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody that are responsible for antigen binding. The hypervariable region generally comprises amino acid residues from a "complementarity determining region" or "CDR" (e.g., around about residues 24-34 (L1), 50-56 (L2) and 89-97 (L3) in the $V_L$, and around about 31-35 (H1), 50-65 (H2) and 95-102 (H3) in the $V_H$ when numbered in accordance with the Kabat numbering system; Kabat et al., Sequences of Proteins of Immunological Interest, 5th Ed. Public Health Service, National Institutes of Health, Bethesda, Md. (1991)); and/or those residues from a "hypervariable loop" (e.g., residues 24-34 (L1), 50-56 (L2) and 89-97 (L3) in the $V_L$, and 26-32 (H1), 52-56 (H2) and 95-101 (H3) in the $V_H$ when numbered in accordance with the Chothia numbering system; Chothia and Lesk, J. Mol. Biol. 196:901-917 (1987)); and/or those residues from a "hypervariable loop"/CDR (e.g., residues 27-38 (L1), 56-65 (L2) and 105-120 (L3) in the $V_L$, and 27-38 (H1), 56-65 (H2) and 105-120 (H3) in the $V_H$ when numbered in accordance with the IMGT numbering system; Lefranc, M. P. et al. Nucl. Acids Res. 27:209-212 (1999), Ruiz, M. e al. Nucl. Acids Res. 28:219-221 (2000)). Optionally the antibody has symmetrical insertions at one or more of the following points 28, 36 (L1), 63, 74-75 (L2) and 123 (L3) in the $V_L$, and 28, 36 (H1), 63, 74-75 (H2) and 123 (H3) in the $V_H$ when numbered in accordance with AHo; Honneger, A. and Plunkthun, A. J. Mol. Biol. 309:657-670 (2001)).

By "germline nucleic acid residue" is meant the nucleic acid residue that naturally occurs in a germline gene encoding a constant or variable region. "Germline gene" is the DNA found in a germ cell (i.e., a cell destined to become an egg or in the sperm). A "germline mutation" refers to a heritable change in a particular DNA that has occurred in a germ cell or the zygote at the single-cell stage, and when transmitted to offspring, such a mutation is incorporated in every cell of the body. A germline mutation is in contrast to a somatic mutation which is acquired in a single body cell. In some cases, nucleotides in a germline DNA sequence encoding for a variable region are mutated (i.e., a somatic mutation) and replaced with a different nucleotide.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816, 567). The "monoclonal antibodies" may also be isolated from phage antibody libraries using the techniques described in Clackson et al., Nature, 352:624-628 (1991) and Marks et al., J. Mol. Biol., 222:581-597 (1991), for example.

In some aspects, the alternative EBV immortalization method described in WO2004/076677 is used. Using this method, B-cells producing the antibody of the invention can be transformed with EBV in the presence of a polyclonal B cell activator. Transformation with EBV is a standard technique and can easily be adapted to include polyclonal B cell activators. Additional stimulants of cellular growth and differentiation may be added during the transformation step to further enhance the efficiency. These stimulants may be cytokines such as IL-2 and IL-15. In a particularly preferred aspect, IL-2 is added during the immortalization step to further improve the efficiency of immortalization, but its use is not essential.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, 81:6851-6855 (1984)). The present invention provides variable domain antigen-binding sequences derived from human antibodies. Accordingly, chimeric antibodies of primary interest herein include antibodies having one or more human antigen binding sequences (e.g., CDRs) and containing one or more sequences derived from a non-human antibody, e.g., an FR or C region sequence. In addition, chimeric antibodies of primary interest herein include those comprising a human variable domain antigen binding sequence of one antibody class or subclass and another sequence, e.g., FR or C region sequence, derived from another antibody class or subclass. Chimeric antibodies of interest herein also include those containing variable domain antigen-binding sequences related to those described herein or derived from a different species, such as a non-human primate (e.g., Old World Monkey, Ape, etc). Chimeric antibodies also include primatized and humanized antibodies.

Furthermore, chimeric antibodies may contain residues that are not found in the recipient antibody or in the donor antibody. These modifications are made to further refine antibody performance. For further details, see Jones et al., Nature 321:522-525 (1986); Riechmann et al., Nature 332:323-329 (1988); and Presta, Curr. Op. Struct. Biol. 2:593-596 (1992).

A "humanized antibody" is generally considered to be a human antibody that has one or more amino acid residues introduced into it from a source that is non-human. These non-human amino acid residues are often referred to as "import" residues, which are typically taken from an "import" variable domain. Humanization is traditionally performed following the method of Winter and co-workers (Jones et al., Nature, 321:522-525 (1986); Reichmann et al., Nature, 332:323-327 (1988); Verhoeyen et al., Science, 239: 1534-1536 (1988)), by substituting import hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In some embodiments a humanized antibody is an immunoglobulin, wherein the amino acids directly involved in antigen binding, the complementarity determining regions (CDR), of the heavy and light chains are not of human origin, while the rest of the immunoglobulin molecule, the framework regions of the variable heavy and light chains and the constant regions of the heavy and light chains, are of human origin.

A "human antibody" is an antibody containing only sequences present in an antibody naturally produced by a human. However, as used herein, human antibodies may contain residues or modifications not found in a naturally occurring human antibody, including those modifications and variant sequences described herein. These are typically made to further refine or enhance antibody performance.

"Fully human antibody" refers to an immunoglobulin, such as an antibody, where the whole molecule is of human origin or consists of an amino acid sequence identical to a human form of the antibody.

An "intact" antibody is one that contains an antigen-binding site as well as a $C_L$ and at least heavy chain constant domains, $C_H1$, $C_H2$ and $C_H3$. The constant domains may be native sequence constant domains (e.g., human native sequence constant domains) or amino acid sequence variant thereof. Preferably, the intact antibody has one or more effector functions.

An "antibody fragment" comprises a portion of an intact antibody, preferably the antigen binding or variable region of the intact antibody. Examples of antibody fragments include Fab, Fab', F(ab')$_2$, and Fv fragments; diabodies; linear antibodies (see U.S. Pat. No. 5,641,870; Zapata et al., Protein Eng. 8(10): 1057-1062 [1995]); single-chain antibody molecules; and multispecific antibodies formed from antibody fragments.

The phrase "functional fragment or analog" of an antibody is a compound having qualitative biological activity in common with a full-length antibody. For example, a functional fragment or analog of an anti-IgE antibody is one that can bind to an IgE immunoglobulin in such a manner so as to prevent or substantially reduce the ability of such molecule from having the ability to bind to the high affinity receptor, Fc$_\varepsilon$RI.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment that roughly corresponds to two disulfide linked Fab fragments having divalent antigen-binding activity and is still capable of cross-linking antigen. Fab' fragments differ from Fab fragments by having additional few residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments that have hinge cysteines between them. Other chemical couplings of antibody fragments are also known.

The "Fc" fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment that contains a complete antigen-recognition and -binding site. This fragment consists of a dimer of one heavy- and one light-chain variable region domain in tight, non-covalent association. From the folding of these two domains emanate six hypervariable loops (three loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains that enables the sFv to form the desired structure for antigen binding. (For a review of sFv, see Pluckthun in The Pharmacology of Monoclonal Antibodies, vol. 113, Rosenburg and Moore eds., Springer-Verlag, New York, pp. 269-315 (1994); Borrebaeck 1995, infra.)

The term "diabodies" refers to small antibody fragments prepared by constructing sFv fragments (see preceding paragraph) with short linkers (about 5-10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the $V_H$ and $V_L$ domains of the two antibodies are present on different polypeptide chains. Diabodies are described more fully in, for example, EP 404,097; WO 93/11161; and Hollinger et al., Proc. Natl. Acad. Sci. USA, 90:6444-6448 (1993).

Domain antibodies (dAbs), which can be produced in fully human form, are the smallest known antigen-binding fragments of antibodies, ranging from 11 kDa to 15 kDa. dAbs are the robust variable regions of the heavy and light chains of immunoglobulins (VH and VL respectively). They are highly expressed in microbial cell culture, show favourable biophysical properties including solubility and temperature stability, and are well suited to selection and affinity maturation by in vitro selection systems such as phage display. dAbs are bioactive as monomers and, owing to their small size and inherent stability, can be formatted into larger molecules to create drugs with prolonged serum half-lives or other pharmacological activities. Examples of this technology have been described in WO9425591 for antibodies derived from Camelidae heavy chain Ig, as well in US20030130496 describing the isolation of single domain fully human antibodies from phage libraries.

As used herein, an antibody that "internalizes" is one that is taken up by (i.e., enters) the cell upon binding to an antigen on a mammalian cell (e.g., a cell surface polypeptide or receptor). The internalizing antibody will of course include antibody fragments, human or chimeric antibody, and antibody conjugates. For certain therapeutic applications, internalization in vivo is contemplated. The number of antibody molecules internalized will be sufficient or adequate to kill a cell or inhibit its growth, especially an infected cell. Depending on the potency of the antibody or antibody conjugate, in some instances, the uptake of a single antibody molecule into the cell is sufficient to kill the target cell to which the antibody binds. For example, certain toxins are highly potent in killing such that internalization of one molecule of the toxin conjugated to the antibody is sufficient to kill the infected cell.

As used herein, an antibody is said to be "immunospecific," "specific for" or to "specifically bind" an antigen if it reacts at a detectable level with the antigen, preferably with an affinity constant, $K_a$, of greater than or equal to about $10^4 M^{-1}$, or greater than or equal to about $10^5 M^{-1}$, greater than or equal to about $10^6 M^{-1}$, greater than or equal to about $10^7 M^{-1}$, or greater than or equal to $10^8 M^{-1}$. Affinity of an antibody for its cognate antigen is also commonly expressed as a dissociation constant $K_D$, and in certain embodiments, a GM-CSF antibody specifically binds to GM-CSF, an epitope thereof, or a GM-CSF polypeptide fragment, if it binds with a $K_D$ of less than or equal to $10^{-4}$ M, less than or equal to about $10^{-5}$ M, less than or equal to about $10^{-6}$ M, less than or equal to $10^{-7}$ M, or less than or equal to $10^{-8}$ M. Affinities of antibodies can be readily determined using conventional techniques, for example, those described by Scatchard et al. (*Ann. N.Y. Acad. Sci. USA* 51:660 (1949)).

Binding properties of an antibody to antigens, cells or tissues thereof may generally be determined and assessed using immunodetection methods including, for example, immunofluorescence-based assays, such as immuno-histochemistry (IHC) and/or fluorescence-activated cell sorting (FACS).

An antibody having a "biological characteristic" of a designated antibody is one that possesses one or more of the biological characteristics of that antibody which distinguish it from other antibodies. For example, in certain embodiments, an antibody with a biological characteristic of a designated antibody will bind the same epitope as that bound by the designated antibody and/or have a common effector function as the designated antibody.

The term "antagonist" antibody is used in the broadest sense, and includes an antibody that partially or fully blocks, inhibits, or neutralizes a biological activity of an epitope, polypeptide, or cell that it specifically binds. Methods for identifying antagonist antibodies may comprise contacting a polypeptide or cell specifically bound by a candidate antagonist antibody with the candidate antagonist antibody and measuring a detectable change in one or more biological activities normally associated with the polypeptide or cell.

An antibody that "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). Preferably the cell is an infected cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the antibody that induces apoptosis is one that results in about 2 to 50 fold, preferably about 5 to 50 fold, and most preferably about 10 to 50 fold, induction of annexin binding relative to untreated cell in an annexin binding assay.

Antibody "effector functions" refer to those biological activities attributable to the Fc region (a native sequence Fc region or amino acid sequence variant Fc region) of an antibody, and vary with the antibody isotype. Examples of antibody effector functions include: Clq binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

"Antibody-dependent cell-mediated cytotoxicity" or "ADCC" refers to a form of cytotoxicity in which secreted Ig bound to Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or U.S. Pat. No. 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al., *Proc. Natl. Acad. Sci.* (USA) 95:652-656 (1998).

"Fc receptor" or "FcR" describes a receptor that binds to the Fc region of an antibody. In certain embodiments, the FcR is a native sequence human FcR. Moreover, a preferred FcR is one that binds an IgG antibody (a gamma receptor) and includes receptors of the FcγRI, FcγRII, and FcγRIII subclasses, including allelic variants and alternatively spliced forms of these receptors. FCγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain Inhibiting receptor FcγRIIB contains an immunoreceptor tyrosine-based inhibition motif (ITIM) in its cytoplasmic domain. (see review M. in Daeron, Annu Rev. Immunol. 15:203-234 (1997)). FcRs are reviewed in Ravetch and Kinet, Annu Rev. Immunol 9:457-92 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol. 117:587 (1976) and Kim et al., J. Immunol. 24:249 (1994)).

"Human effector cells" are leukocytes that express one or more FcRs and perform effector functions. Preferably, the cells express at least FcγRIII and perform ADCC effector function. Examples of human leukocytes that mediate ADCC include PBMC, NK cells, monocytes, cytotoxic T cells and neutrophils; with PBMCs and NK cells being preferred. The effector cells may be isolated from a native source, e.g., from blood.

"Complement dependent cytotoxicity" or "CDC" refers to the lysis of a target cell in the presence of complement. Activation of the classical complement pathway is initiated by the binding of the first component of the complement system (Clq) to antibodies (of the appropriate subclass) that are bound to their cognate antigen. To assess complement activation, a CDC assay, e.g., as described in Gazzano-Santoro et al., J. Immunol. Methods 202:163 (1996), may be performed.

As used herein the term "biomolecule" refers to any molecule that can be conjugated to, coadministered with, administered before or after administering an antibody, or otherwise used in association with an antibody of the invention. Biomolecules include, but are not limited to, enzymes, proteins, peptides, amino acids, nucleic acids, lipids, carbohydrates, and fragments, homologs, analogs, or derivatives, and combinations thereof. Examples of biomolecules include but are not limited to interleukin-2, interferon alpha, interferon beta, interferon gamma, rituxan, zevalin, herceptin, erbitux, and avastin. The biomolecules can be native, recombinant, or synthesized, and may be modified from their native form with, for example, glycosylations, acetylations, phosphorylations, myristylations, and the like. The term biomolecule as used herein includes naturally occurring molecules and synthetic molecules having no biological origin.

A "mammal" for purposes of treating an infection, refers to any mammal, including humans, domestic and farm animals, and zoo, sports, or pet animals, such as dogs, cats, cattle, horses, sheep, pigs, goats, rabbits, etc. Preferably, the mammal is human.

"Treating" or "treatment" or "alleviation" refers to both therapeutic treatment and prophylactic or preventative measures; wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for an infection if, after receiving a therapeutic amount of an antibody according to the methods of the present invention, the patient shows observable and/or measurable reduction in or absence of one or more of the following: reduction in the number of infected cells or absence of the infected cells; reduction in the percent of total cells that are infected; and/or relief to some extent, one or more of the symptoms associated with the specific infection; reduced morbidity and mortality, and improvement in quality of life issues. The above parameters for assessing successful treatment and improvement in the disease are readily measurable by routine procedures familiar to a physician.

The term "therapeutically effective amount" refers to an amount of an antibody or a drug effective to "treat" a disease or disorder in a subject or mammal. See preceding definition of "treating."

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

Administration "in combination with" one or more further therapeutic agents includes simultaneous (concurrent) and consecutive administration in any order.

"Carriers" as used herein include pharmaceutically acceptable carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ polyethylene glycol (PEG), and PLURONICS™.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents e.g., methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below.

A "growth inhibitory agent" when used herein refers to a compound or composition which inhibits growth of a cell, either in vitro or in vivo. Examples of growth inhibitory agents include agents that block cell cycle progression, such as agents that induce G1 arrest and M-phase arrest. Classical M-phase blockers include the vinca alkaloids (vincristine, vinorelbine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds., Chapter 1, entitled "Cell cycle regulation, oncogenes, and antineoplastic drugs" by Murakami et al. (W B Saunders: Philadelphia, 1995), especially p. 13. The taxanes (paclitaxel and docetaxel) are anticancer drugs both derived from the yew tree. Docetaxel (TAXOTERE™, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

"Label" as used herein refers to a detectable compound or composition that is conjugated directly or indirectly to the antibody so as to generate a "labeled" antibody. The label may be detectable by itself (e.g., radioisotope labels or fluorescent labels) or, in the case of an enzymatic label, may catalyze chemical alteration of a substrate compound or composition that is detectable.

The term "epitope tagged" as used herein refers to a chimeric polypeptide comprising a polypeptide fused to a "tag polypeptide." The tag polypeptide has enough residues to provide an epitope against which an antibody can be made, yet is short enough such that it does not interfere with activity of the polypeptide to which it is fused. The tag polypeptide is also preferably fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

A "small molecule" is defined herein to have a molecular weight below about 500 Daltons.

The terms "nucleic acid" and "polynucleotide" are used interchangeably herein to refer to single- or double-stranded RNA, DNA, or mixed polymers. Polynucleotides may include genomic sequences, extra-genomic and plasmid sequences, and smaller engineered gene segments that express, or may be adapted to express polypeptides.

An "isolated nucleic acid" is a nucleic acid that is substantially separated from other genome DNA sequences as well as proteins or complexes such as ribosomes and polymerases, which naturally accompany a native sequence. The term embraces a nucleic acid sequence that has been removed from its naturally occurring environment, and includes recombinant or cloned DNA isolates and chemically synthesized analogues or analogues biologically synthesized by heterologous systems. A substantially pure nucleic acid includes isolated forms of the nucleic acid. Of course, this refers to the nucleic acid as originally isolated and does not exclude genes or sequences later added to the isolated nucleic acid by the hand of man.

The term "polypeptide" is used in its conventional meaning, i.e., as a sequence of amino acids. The polypeptides are not limited to a specific length of the product. Peptides, oligopeptides, and proteins are included within the definition of polypeptide, and such terms may be used interchangeably herein unless specifically indicated otherwise. This term also does not refer to or exclude post-expression modifications of the polypeptide, for example, glycosylations, acetylations, phosphorylations and the like, as well as other modifications known in the art, both naturally occurring and non-naturally occurring. A polypeptide may be an entire protein, or a subsequence thereof. Particular polypeptides of interest in the context of this invention are amino acid subsequences comprising CDRs and being capable of binding a GM-CSF antigen.

An "isolated polypeptide" is one that has been identified and separated and/or recovered from a component of its natural environment. In preferred embodiments, the isolated polypeptide will be purified (1) to greater than 95% by weight of polypeptide as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or, preferably, silver stain. Isolated polypeptide includes the polypeptide in situ within recombinant cells since at least one component of the polypeptide's natural environment will not be present. Ordinarily, however, isolated polypeptide will be prepared by at least one purification step.

A "native sequence" polynucleotide is one that has the same nucleotide sequence as a polynucleotide derived from nature. A "native sequence" polypeptide is one that has the same amino acid sequence as a polypeptide (e.g., antibody) derived from nature (e.g., from any species). Such native sequence polynucleotides and polypeptides can be isolated from nature or can be produced by recombinant or synthetic means.

A polynucleotide "variant," as the term is used herein, is a polynucleotide that typically differs from a polynucleotide specifically disclosed herein in one or more substitutions, deletions, additions and/or insertions. Such variants may be naturally occurring or may be synthetically generated, for example, by modifying one or more of the polynucleotide sequences of the invention and evaluating one or more biological activities of the encoded polypeptide as described herein and/or using any of a number of techniques well known in the art.

A polypeptide "variant," as the term is used herein, is a polypeptide that typically differs from a polypeptide specifically disclosed herein in one or more substitutions, deletions, additions and/or insertions. Such variants may be naturally occurring or may be synthetically generated, for example, by modifying one or more of the above polypeptide sequences of the invention and evaluating one or more biological activities of the polypeptide as described herein and/or using any of a number of techniques well known in the art.

Modifications may be made in the structure of the polynucleotides and polypeptides of the present invention and still obtain a functional molecule that encodes a variant or derivative polypeptide with desirable characteristics. When it is desired to alter the amino acid sequence of a polypeptide to create an equivalent, or even an improved, variant or portion of a polypeptide of the invention, one skilled in the art will typically change one or more of the codons of the encoding DNA sequence.

For example, certain amino acids may be substituted for other amino acids in a protein structure without appreciable loss of its ability to bind other polypeptides (e.g., antigens) or cells. Since it is the binding capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the peptide sequences of the disclosed compositions, or corresponding DNA sequences that encode said peptides without appreciable loss of their biological utility or activity.

In many instances, a polypeptide variant will contain one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity. U.S. Pat. No. 4,554,101 states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, tip, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

Polypeptides may comprise a signal (or leader) sequence at the N-terminal end of the protein, which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

When comparing polynucleotide and polypeptide sequences, two sequences are said to be "identical" if the sequence of nucleotides or amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign® program in the Lasergene® suite of bioinformatics software (DNASTAR®, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogenes pp. 626-645 *Methods in Enzymology* vol. 183, Academic Press, Inc., San Diego, Calif.; Higgins, D. G. and Sharp, P. M. (1989) *CABIOS* 5:151-153; Myers, E. W. and Muller W. (1988) *CABIOS* 4:11-17; Robinson, E. D. (1971) *Comb. Theon* 11:105; Santou, N. Nes, M. (1987) *Mol. Biol. Evol.* 4:406-425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) *Proc. Natl. Acad., Sci. USA* 80:726-730.

Alternatively, optimal alignment of sequences for comparison may be conducted by the local identity algorithm of Smith and Waterman (1981) *Add. APL. Math* 2:482, by the identity alignment algorithm of Needleman and Wunsch (1970) *J. Mol. Biol.* 48:443, by the search for similarity methods of Pearson and Lipman (1988) *Proc. Natl. Acad. Sci. USA* 85: 2444, by computerized implementations of these algorithms (GAP, BESTFIT, BLAST®, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST® and BLAST® 2.0 algorithms, which are described in Altschul et al. (1977) *Nucl. Acids Res.* 25:3389-3402 and Altschul et al. (1990) *J. Mol. Biol.* 215:403-410, respectively. BLAST® and BLAST® 2.0 can be used, for example with the parameters described herein, to determine percent sequence identity for the polynucleotides and polypeptides of the invention. Software for performing BLAST® analyses is publicly available through the National Center for Biotechnology Information.

In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN® program (for nucleotide sequences) uses as defaults a wordlength (W) of 11, and expectation (E) of 10, and the BLOSUM62 scoring matrix (see Henikoff and Henikoff (1989) *Proc. Natl. Acad. Sci. USA* 89:10915) alignments, (B) of 50, expectation (E) of 10, M=5, N=−4 and a comparison of both strands.

For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST® algorithm parameters W, T and X determine the sensitivity and speed of the alignment.

In one approach, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residues occur in both sequences to yield the number of matched positions, dividing the number of matched positions by the total number of positions in the reference sequence (i.e., the window size) and multiplying the results by 100 to yield the percentage of sequence identity.

"Homology" refers to the percentage of residues in the polynucleotide or polypeptide sequence variant that are identical to the non-variant sequence after aligning the sequences and introducing gaps, if necessary, to achieve the maximum percent homology. In particular embodiments, polynucleotide and polypeptide variants have at least 70%, at least 75%, at least 80%, at least 90%, at least 95%, at least 98%, or at least 99% polynucleotide or polypeptide homology with a polynucleotide or polypeptide described herein.

"Vector" includes shuttle and expression vectors. Typically, the plasmid construct will also include an origin of replication (e.g., the ColE1 origin of replication) and a selectable marker (e.g., ampicillin or tetracycline resistance), for replication and selection, respectively, of the plasmids in bacteria. An "expression vector" refers to a vector that contains the necessary control sequences or regulatory elements for expression of the antibodies including antibody fragment of the invention, in bacterial or eukaryotic cells. Suitable vectors are disclosed below.

As used in this specification and the appended claims, the singular forms "a," "an" and "the" include plural references unless the content clearly dictates otherwise.

The invention also includes nucleic acid sequences encoding part or all of the light and heavy chains and CDRs of the present invention. Due to redundancy of the genetic code, variants of these sequences will exist that encode the same amino acid sequences.

Variant antibodies are also included within the scope of the invention. Thus, variants of the sequences recited in the application are also included within the scope of the invention. Further variants of the antibody sequences having improved affinity may be obtained using methods known in the art and are included within the scope of the invention. For example, amino acid substitutions may be used to obtain antibodies with further improved affinity. Alternatively, codon optimization of the nucleotide sequence may be used to improve the efficiency of translation in expression systems for the production of the antibody.

Preferably, such variant antibody sequences will share 70% or more (i.e. 80, 85, 90, 95, 97, 98, 99% or more) sequence identity with the sequences recited in the application. Preferably such sequence identity is calculated with regard to the full length of the reference sequence (i.e. the sequence recited in the application). Preferably, percentage identity, as referred to herein, is as determined using BLAST version 2.1.3 using the default parameters specified by the NCBI (the National Center for Biotechnology Information; http://www.ncbi.nlm.nih.gov/) [Blosum 62 matrix; gap open penalty=11 and gap extension penalty=1].

Further included within the scope of the invention are vectors such as expression vectors, comprising a nucleic acid sequence according to the invention. Cells transformed with such vectors are also included within the scope of the invention.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

Identification of 1783J22 that Neutralizes GM-CSF Bioactivity in TF1 Proliferation Assay IgG expressing Memory B cells were isolated from an idiotypic pulmonary alveolar proteinosis (iPAP) patient using negative depletion of other peripheral blood mononuclear cells (PBMC) on magnetic beads. Memory B cells were activated for 7 days at seeding density of around 3 memory B cells/well in the presence of cytokines and feeder cells that promote polyclonal B cell activation. Supernatants of B cell culture wells containing secreted antibodies were screened for GM-CSF neutralization in TF1 (human erthyleukemic cell line) proliferation assay. TF1 cell growth is GM-CSF dependent.

TF1 proliferation screening assay was conducted in duplicate plates. TF1 cells were starved in serum-free culture media containing 0.1% BSA overnight followed by seeding at 1500 TF1 cells/well in 25 µl culture media containing 10% FCS in 384-well plates. B cell culture supernatants were added at 2.5 µl/well. Human GM-CSF intrinsically present in the B cell culture supernatants at around 50 pM supported the growth TF 1 cells. Neutralizing anti-GM-CSF, if present in the B cell culture supernatants, inhibited TF1 proliferation. TF1 cells were cultured in the presence of B cell supernatants for 4 days. Cell Titer-Glo® luminescent reagent (Promega®, Catalog G7571) was added at 25 µl/well and relative luminescence units (RLU) was measured according to manufacturer's instruction.

Figure 1:
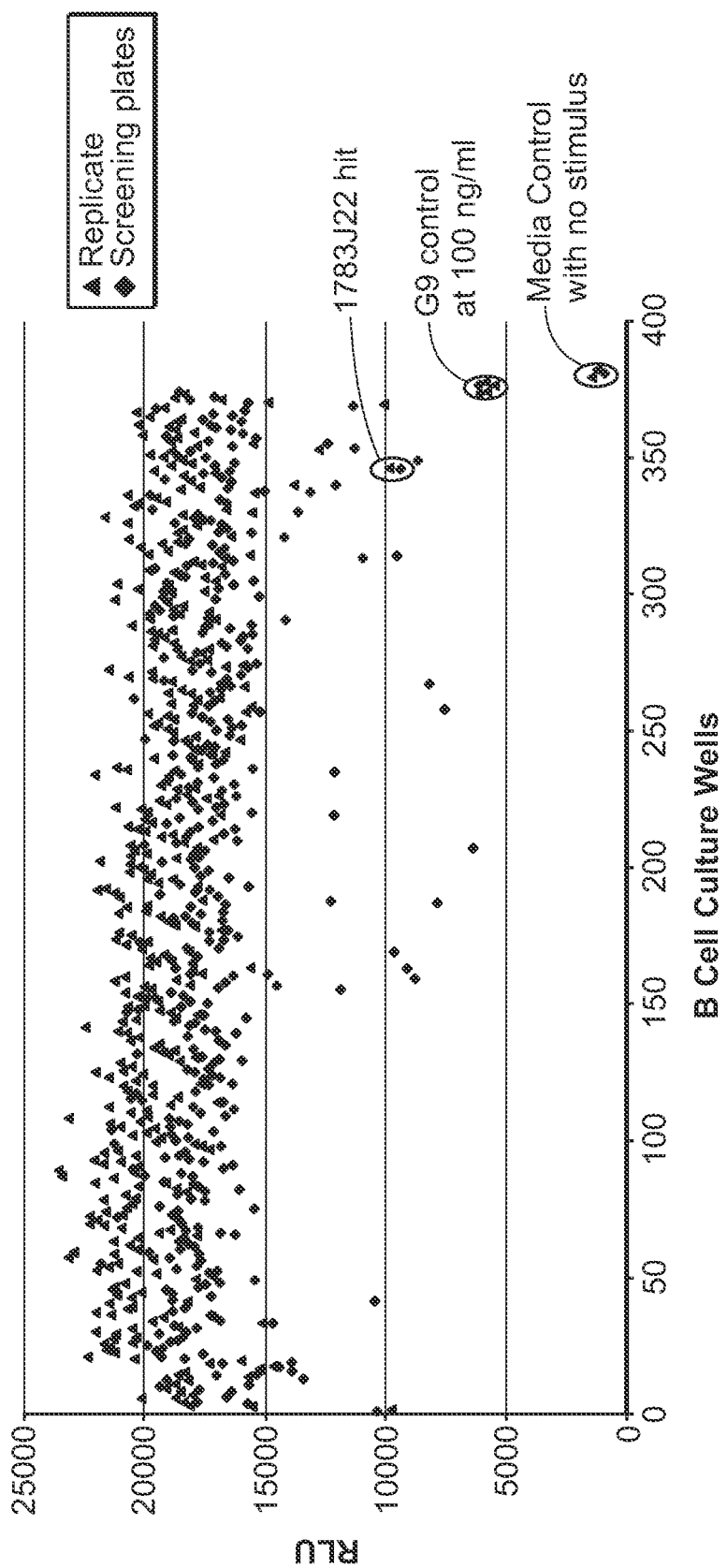
FIG. 1 is a graph depicting the bioactivity of GM-CSF as the amount of relative luminescence units (RLU) per B Cell Culture Well for both replicate and screening plates challenged with human anti-GM-CSF. As shown in the graph, clone 1783J22 is identified as inhibiting GM-CSF bioactivity in both replicate and screening plates, and, therefore, having GM-CSF-neutralizing activity.

FIG. 1 shows that the screening result of the duplicate assay plates containing the neutralizing antibody of interest, 1783J22. The hit was identified based on the reduced RLU compared to the rest of the culture wells on the same plates, indicative of GM-CSF neutralizing activity. Control monoclonal antibody G9 (Li J, et al, 2006, PNAS, 103:3557-62; Sass P M, et al, WO 2007/092939), added to B cell culture supernatants derived from a healthy donor, was used as positive control at 100 ng/ml. G9 monoclonal antibody was generated by grafting the published G9 variable region gene into the same human IgG1 sequence used in reconstructing recombinant 1783J22 (see example 4 below).

Example 2

Confirmation of Binding of 1783J22 to Human GM-CSF

B cell culture supernatant of 1783J22 was tested for binding reactivity to *E. coli*-derived human GM-CSF in the homogeneous proximity-based Alphascreen® assay (Perkin-Elmer®). In brief, the supernatant was pre-incubated with biotinylated human GM-CSF in the presence of protein A-coated acceptor beads overnight at 4° C. Streptavidin-coated donor beads were added to the mixture and luminescence was measured following incubation at ambient temperature in the dark for 2 hours.

FIG. 2 shows the binding activity of 1783J22 to human GM-CSF among a panel of B cell supernatants, most of which with no GM-CSF neutralizing activity.

Example 3

Recovery of GM-CSF Binding Activity in 1783J22 Recombinant Antibody Pool in Transfectant Supernatants The variable region genes for H & L chains were isolated from lysate of the B cell culture corresponding to 1783J22 by RT-PCR amplification using family-specific primer sets. From positive family-specific PCR reactions, pools of the $V_H$ or $V_L$-region clones were cloned into an expression vector upstream to human IgG1 constant domain sequence. Minipreps of these DNA pools, derived from bacterial cultures I suspension, were combined in all possible $V_H$ and $V_L$ family-specific pairs and used to transiently transfect 293 cells. All transfectant supernatants containing secreted recombinant antibodies were screened in Alphascreen® assay as described in example 2.

Figure 3:
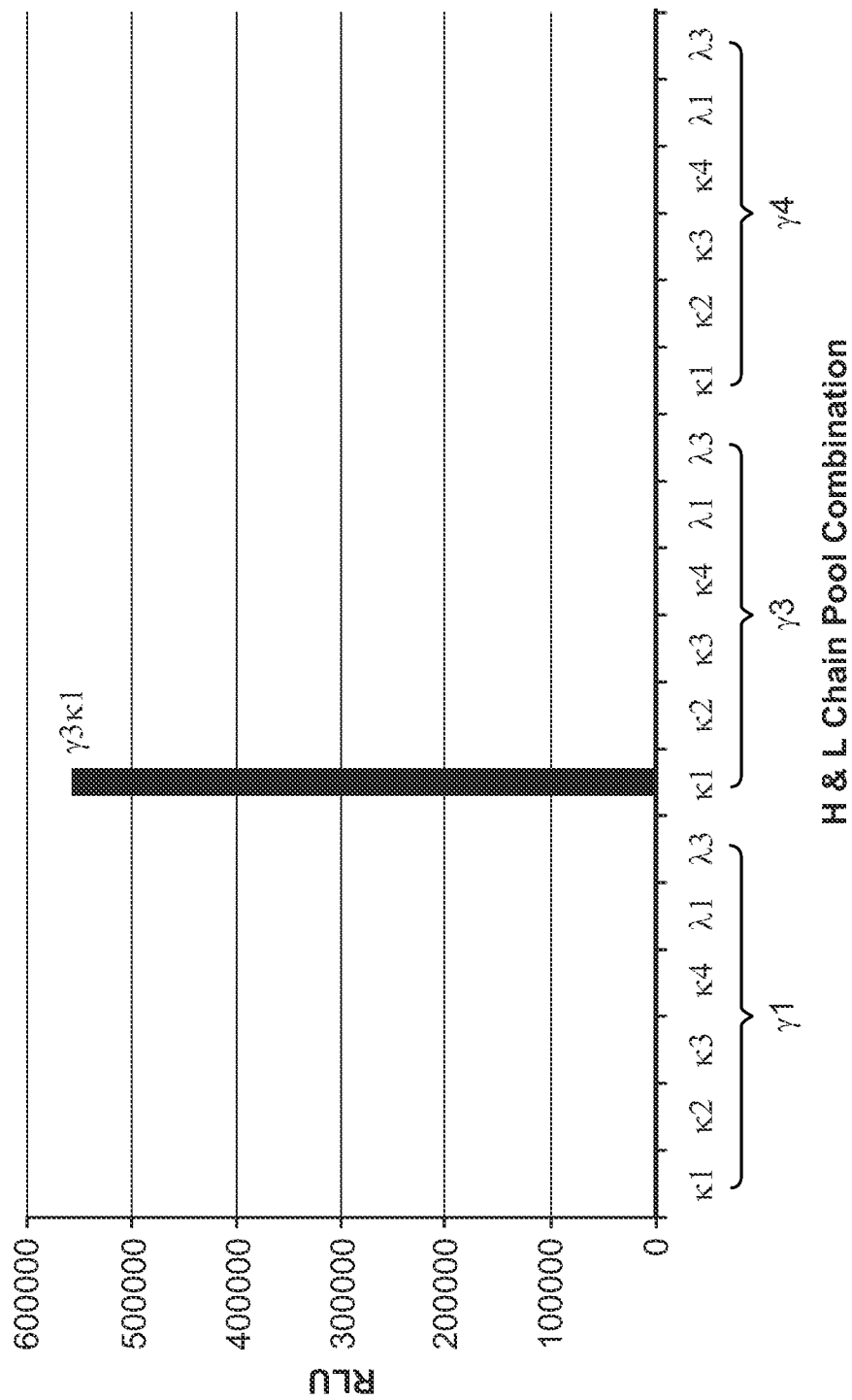
FIG. 3 is a graph depicting the recovery of human GM-CSF binding reactivity of the 1783J22 recombinant antibody from a pool transfectant supernatants derived from the combination of heavy chain (gamma, γ) and light chain (kappa, κ) PCR products. GM-CSF binding reactivity was measured as the relative luminescence units (RLU) per heavy and light (H & L) chain pool combinations. The human monoclonal 1783J22 antibody was reconstituted from the combination of γ3 and κ1 heavy and light chains, respectively.

FIG. 3 shows the human GM-CSF binding reactivity of transfectant supernatants derived from the combination of γ3 and κ1 PCR products.

Example 4

Recovery of Neutralizing Activity in 1783J22 Recombinant Monoclonal Antibody in Transfectant Supernatants To reconstitute the neutralizing mAbs, the miniprep DNA pool of $V_H$ or $V_L$ clones corresponding to the 1783J22 transfectant hit in example 3 was subjected to a deconvolution process. Multiple bacterial colonies were isolated from each $V_H$ or $V_L$ miniprep DNA pool and individual sequences were determined. Paired combinations of individual $V_H$ and $V_L$ sequences in all permutations were transfected in 293 cells. Each transfectant supernatant was screened for human GM-CSF binding reactivity in Alphascreen assay as well as for neutralization activity in TF1 proliferation assay.

Figure 4A:
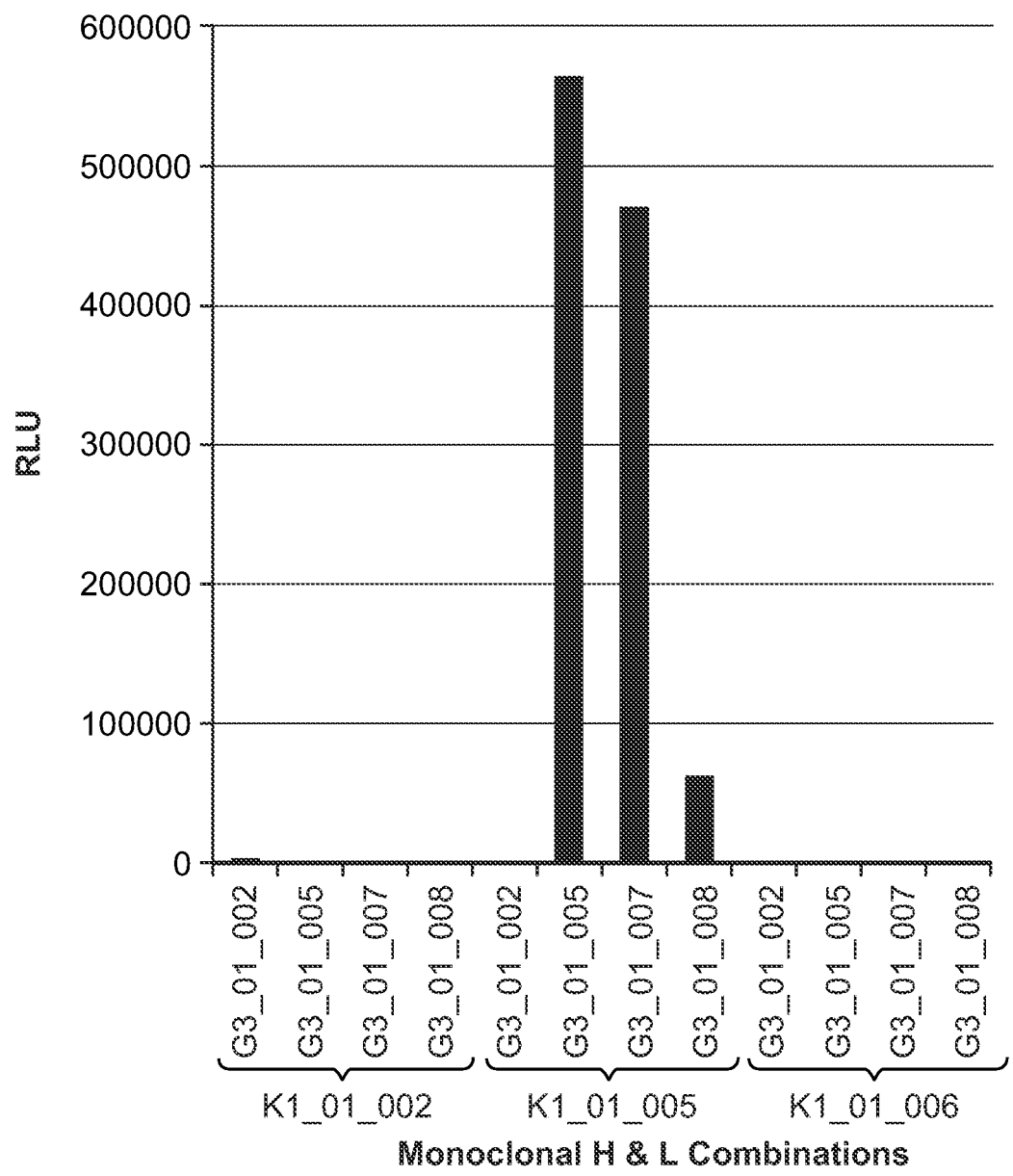
FIG. 4A is a graph depicting the recovery of human GM-CSF binding reactivity of the 1783J22 recombinant monoclonal antibody from transfectant supernatants derived from monoclonal heavy chain (gamma, γ) and light chain (kappa, κ) combinations. GM-CSF binding reactivity was measured as the relative luminescence units (RLU) per monoclonal heavy and light (H & L) chain combinations. Three γ3 sequences, when combined with one κ1 sequence, produced 1783J22 monoclonal antibodies in transfectant supernatants that bind human GM-CSF.

FIG. 4A shows that three γ3 sequences, when combined to one κ1 sequence, produced monoclonal antibodies in transfectant supernatants that bound to human GM-CSF. The transfectant supernatants with binding reactivity were further tested for neutralizing activity in TF1 proliferation assay. The TF1 proliferation assay was conducted in similar fashion as described in example 1, except that 2 pM exogenous human GM-CSF derived from yeast (Leukine® or Sargramostim®, Berlex) was used as stimulator and the cells were incubated in the presence of the transfectant supernatants for 3 days.

Figure 4B:
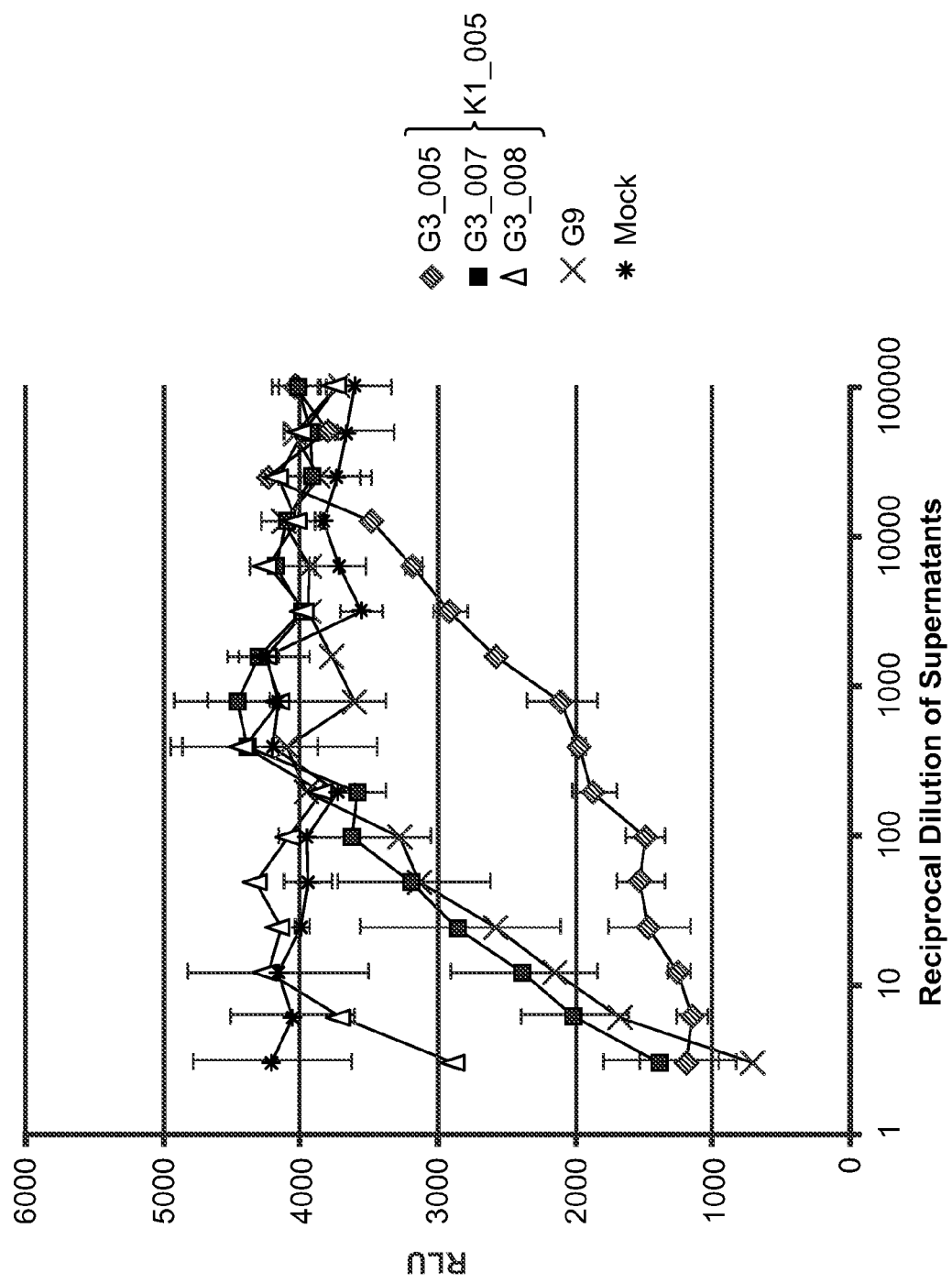
FIG. 4B is a graph depicting the human GM-CSF binding reactivity of the recovered 1783J22 recombinant monoclonal antibodies from FIG. 4A, measured as the relative luminescence units (RLU) per reciprocal dilution of supernatants. Of the 3 reconstituted monoclonal antibodies, those antibodies containing the G3-005 and G3-007 heavy chains, exhibited neutralizing activity in TF1 proliferation assay. Sequence and reactivity data from this graph indicate that G3_005 is the authentic heavy chain for the 1783J22 recombinant monoclonal antibody.
Figure 5:
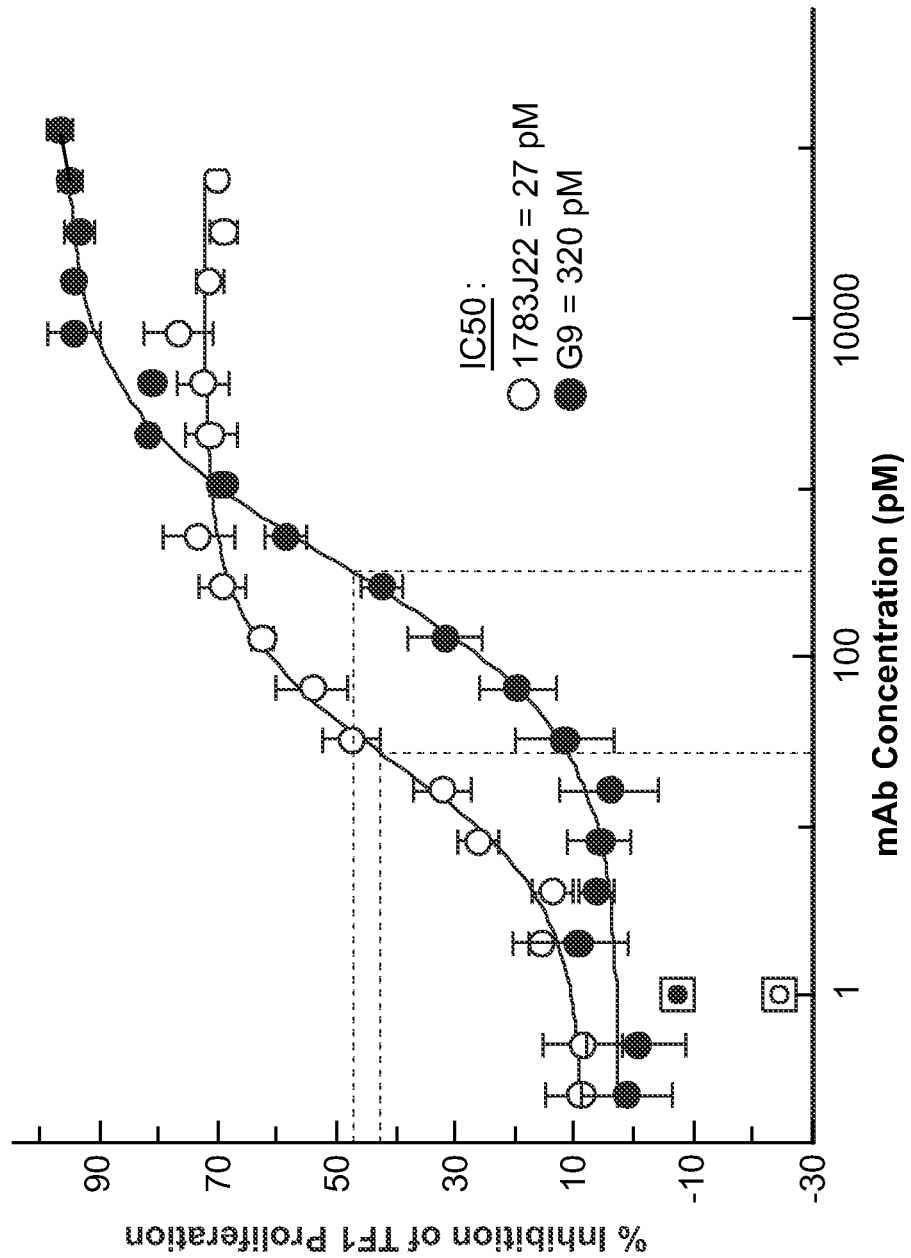
FIG. 5 is a graph depicting the relative potencies of the human anti-GM-CSF monoclonal antibody 1783J22 and the control G9 antibody for neutralizing human GM-CSF derived from yeast. Neutralization potency was measured as the percent (%) inhibition of TF1 proliferation per increasing monoclonal antibody (mAb) concentration (provided in picomoles, pM). The results of the assay were used to determine the half maximal inhibitory concentration, or $IC_{50}$. 1783J22 exhibited a lower $IC_{50}$ value than G9, which indicated a greater neutralization potency of 178J22 than of G9.

FIG. 4B shows that 2 of the 3 reconstituted monoclonal antibodies, G3-005 and G3-007, exhibited neutralizing activity in TF1 proliferation assay. The remaining one monoclonal antibody had very weak neutralization activity. Sequencing analysis indicated that the heavy chain clone G3-007 was contaminated with light chain clones. Only the reconstitution of G3-005 heavy chain clone combined with K1-005 light chain clone as monoclonal antibody in purified form yielded binding and neutralization activities, therefore the G3-005 and K1-005 combination was considered as the authentic constituent of monoclonal antibody of 1783J22.

Example 5

Neutralization Potency of 1783J22 for GM-CSF-Dependent TF1 Proliferation Compared to G9

1783J22 monoclonal antibody was purified from transient transfectant supernatants of 293 cells and compared to purified G9 monoclonal antibodies (Li J, et al, 2006, PNAS, 103:3557-62; WO 2007/092939); US Pat. App. Pub. No. 20080292641A1) in neutralizing TF1 cell proliferation. The TF1 proliferation was conducted in similar fashion as described in Example 4. FIG. 5 shows the relative potency of 1783J22 and G9 in neutralizing human GM-CSF derived from yeast. MAb 1783J22 exhibited a lower $IC_{50}$ value, indicative of higher potency than G9.

Example 6

1783J22 Does Not Compete with G9 in Binding to Human GM-CSF Prepared in Yeast

Purified Fab proteins for 1783J22 and G9 were generated from the corresponding whole IgG antibodies by enzymatic digestion. They were used to cross-compete the binding of whole IgG antibodies of each other to human GM-CSF in Alphascreen® assay. In brief, various concentrations of Fab was pre-incubated with 10 nM human GM-CSF derived from *E. coli* at 4 degree C. for 2 hours, followed by incubation with whole IgG antibody at 6 ng/ml and protein A-coated acceptor beads at 4 degree C. for 2 hours. Streptavidin-coated donor beads were then added to the mixture to incubate at ambient temperature for 2 hours before luminescence was measured.

Figure 6:
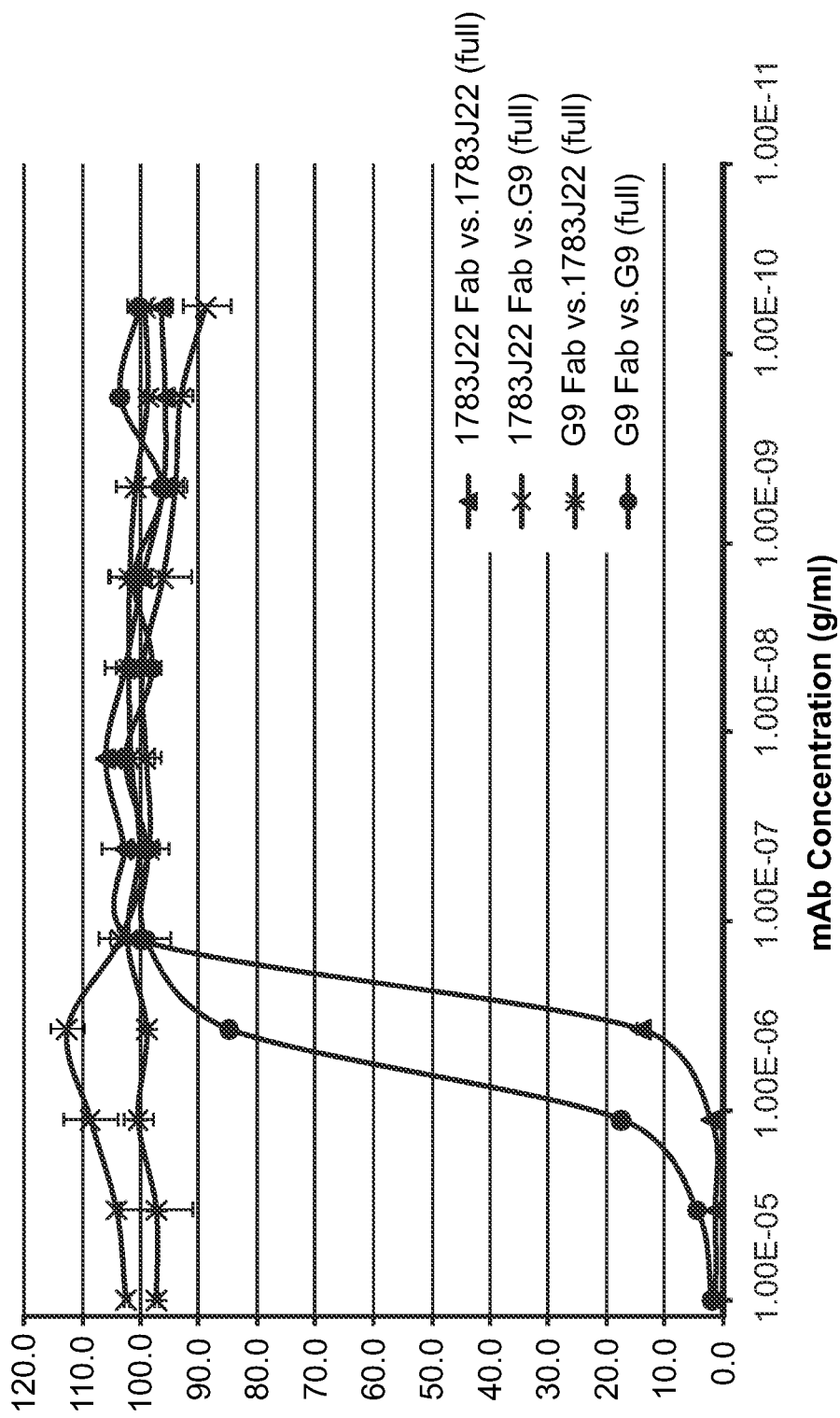
FIG. 6 is a graph depicting the results of a competitive binding assay between 1783J22 (complete antibody), 1783J22 Fab (positive control), G9 (complete antibody), and G9 Fab with respect to human GM-CSF prepared in yeast. The percent (%) cross-competition was measured as a function of increasing monoclonal antibody (mAb) concentration (provided in grams per milliliter, or g/ml). The results demonstrated that the 1783J22 Fab does not compete with G9 whole antibody binding to human GM-CSF, and that the G9 Fab does not compete with 1783J22 whole antibody binding to human GM-CSF. As positive controls, the Fab of 1783J22 competed with its whole antibody in a dose dependent manner, and the Fab of G9 also competes with its whole antibody in a dose dependent manner.

FIG. 6 shows that 1783J22 Fab did not compete with G9 whole antibody binding to human GM-CSF, and vice versa, G9 Fab did not compete with 1783J22 whole antibody binding to human GM-CSF. As positive controls, Fab of 1783J22 competed with its whole antibody in a dose dependent manner, and Fab of G9 also competed with its whole antibody in a dose dependent manner.

Example 7

Affinity of 1783J22 Fab Binding to Human GM-CSF Prepared in Yeast via BIACORE Analysis 1783J22 Fab was used to determine the affinity of binding to human GM-CSF derived from yeast via BIACORE® analysis (Biosensor Tools LLC, Salt Lake City, Utah). 1783J22 exhibited binding affinity of 38.9 pM (Table 1). In contrast, G9 exhibited binding characteristic of 3 independent sites with affinities of 5.1 nM, 611 pM, 58.2 pM (Table 1). Since the human GM-CSF derived from yeast contained 3 glycoforms of apparent molecular size of 15.5, 16.8 and 19.5 kD, it is possible that the 3 affinities of G9 corresponded to binding to the 3 glycoforms.

TABLE 1

Affinity of 1783J22 Fab Binding to Human GM-CSF Prepared in Yeast via BIACORE Analysis

| Anti-GM-CSF | Affinity ($K_D$) | $K_a$ ($M^{-1}s^{-1}$) | $K_d$ ($s^{-1}$) |
|---|---|---|---|
| 1783J22 | 38.9 pM | $3.15 \times 10^5$ | $1.23 \times 10^{-5}$ |
| G9 (Morphotek) | 5.1 nM (59%) | $4.90 \times 10^5$ | $2.50 \times 10^{-3}$ |
|  | 611 pM (17%) | $1.80 \times 10^5$ | $1.10 \times 10^{-4}$ |
|  | 58.2 pM (24%) | $5.50 \times 10^6$ | $3.20 \times 10^{-4}$ |

Example 8

Cross-Reactivity of 1783J22 with Rabbit GM-CSF

1783J22 was tested for cross-species reactivity to rabbit and rhesus GM-CSF. GM-CSF of human, rhesus and rabbit origins were recombinantly expressed as anchored to the surface of transient transfected cells via a glycophosphatidylinositol (GPI) moiety. The amino acid sequence that enabled the addition of the GPI moiety during post-translational protein modification was derived from LFA-3 and engineered at the C-terminus of GM-CSF. A V5 tag was also included at the C-terminus of expressed GPI-linked GM-CSF and was used to monitor the recombinant GPI-linked GM-CSF protein expression on the 293 transfectant cell surface. FIG. 7 demonstrates that 1782J22 binds to rabbit, human and rhesus GM-CSF, whereas G9 binds to only human and rhesus GM-CSF but not rabbit GM-CSF. No binding of either antibody was detected for Tetanus toxoid that was GPI-linked to the transfectant cell surface in similar manner.

Example 9

Cross-Reactivity of 1783J22 with Recombinant Rabbit GM-CSF-His Proteins

The cross-reactivity of 1783J22 was further confirmed by Western blot analysis of recombinant rabbit GM-CSF expressed as a 6×His-tagged soluble protein. Clarified culture supernatants containing recombinant rabbit GM-CSF-His (His-rGMCSF) secreted by HEK293 transfectants were separated in 4-20% SDS-PAGE gel under non-reducing conditions and western-transferred for staining with 1783J22 or anti-His. FIG. 8 (right panel) shows that 1783J22 binds to the 20 kD and 40 kD proteins (marked by red arrows) that are also recognized by anti-His. Supernatants derived from HEK293 cells transfected with untagged rabbit GM-CSF (rGMCSF) contained much lower levels of 1783J22 binding. Human GM-CSF (Leukine) was used as the positive binding control for 1783J22. FIG. 8 (left panel) shows that the 20 kD and 40 kD proteins can be purified from the clarified culture supernatants using Nickel chelate affinity chromatography specifically recognizing the 6-His tag. The 40 kD protein band is likely a disulfide-linked dimer of the 20 kD rabbit GM-CSF-His as it is not detectable under reducing conditions of SDS-PAGE analysis. The overall results demonstrate that 1783J22 can cross-react with soluble recombinant rabbit GM-CSF.

Example 10

Affinity of 1783J22 Fab Binding to Rabbit GM-CSF Prepared in Human HEK293 Cells via BIACORE Analysis 1783J22 Fab was used to determine the affinity of binding to soluble recombinant rabbit GM-CSF-His purified from human HEK293 transfectants via BIACORE analysis (Biosensor Tools, Salt Lake City, Utah). 1783J22 exhibited binding affinity of 900±200 pM to rabbit GM-CSF (Table 2). The affinity for rabbit GM-CSF is about 25-fold lower than that for human GM-CSF.

TABLE 2

Affinity of 1783J22 Fab Binding to Rabbit GM-CSF

| GM-CSF | Affinity ($K_D$) | $K_a$ ($M^{-1}s^{-1}$) | $K_d$ ($s^{-1}$) |
|---|---|---|---|
| Human (Leukine) | 38.9 ± 0.9 pM | $3.15 \pm 0.07 \times 10^5$ | $1.23 \times 10^{-5}$ |
| Rabbit (His-tagged) | 900 ± 200 pM | $1.06 \pm 0.03 \times 10^5$ | $1.0 \pm 0.2 \times 10^{-4}$ |

Example 11

1783J22 Binds to Rhesus GM-CSF Expressed on HEK293 Cells Similarly Well as to Human GM-CSF Rhesus monkeys provide clinically relevant inflammatory disease models for studying the effects of neutralizing anti-GM-CSF. As shown in FIG. 7 and described in Example 8, 1783J22 binds to both human and rhesus GM-CSF. To further evaluate the relative affinity of 1783J22 binding to rhesus GM-CSF compared to human GM-CSF, the binding intensity of 1783J22 whole antibody to HEK293 cells transiently transfected with recombinant GPI-linked rhesus or human GM-CSF was determined. FIG. 9 illustrates the dose response of the 1783J22 binding analysis by FACS. Results demonstrate that 1783J22 binds to rhesus and human GM-CSF with similar relative affinity. In comparison, anti-GM-CSF G9 binds rhesus GM-CSF more weakly than it binds human GM-CSF.

Other Embodiments

Although specific embodiments of the invention have been described herein for purposes of illustration, various modifications may be made without deviating from the spirit and scope of the invention. Accordingly, the invention is not limited except as by the appended claims.

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. GenBank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. An isolated anti-GM-CSF antibody, wherein the antibody comprises a $V_H$ CDR1 region comprising the amino acid sequence of FPFHKYTMT (SEQ ID NO: 8); a $V_H$ CDR2 region comprising the amino acid sequence of VSGVNGKTYYSPSVRG (SEQ ID NO: 9); a $V_H$ CDR3 region comprising the amino acid sequence of GPGGHLHYYYGLDV (SEQ ID NO: 10); a $V_L$ CDR1 region comprising the amino acid sequence of RASQAINNYVA (SEQ ID NO: 14); a $V_L$ CDR2 region comprising the amino acid sequence of GASNLQP (SEQ ID NO: 15); and a $V_L$ CDR3 region comprising the amino acid sequence of QNYFGYPLT (SEQ ID NO: 16).

2. An isolated anti-GM-CSF antibody, wherein the antibody comprises a $V_H$ CDR1 region comprising the amino acid sequence of GFPFHKYTMT (SEQ ID NO: 11); a $V_H$ CDR2 region comprising the amino acid sequence of VSGVNGKTY (SEQ ID NO: 12); a $V_H$ CDR3 region comprising the amino acid sequence of GPGGHLHYYYGLDV (SEQ ID NO: 10); a $V_L$ CDR1 region comprising the amino acid sequence of RASQAINNYVA (SEQ ID NO: 14); a $V_L$ CDR2 region comprising the amino acid sequence of GASNLQP (SEQ ID NO: 15); and a $V_L$ CDR3 region comprising the amino acid sequence of QNYFGYPLT (SEQ ID NO: 16).

3. An isolated fully human monoclonal anti-GM-CSF antibody comprising a heavy chain sequence comprising the amino acid sequence SEQ ID NO: 2 and a light chain sequence comprising amino acid sequence SEQ ID NO: 5.

4. A composition comprising the antibody of claim 1, 2, or 3 and a pharmaceutically-acceptable carrier.

5. The antibody of claim 1, 2, or 3, wherein the antibody is operably-linked to a therapeutic agent or a detectable label.

6. The composition of claim 4, wherein the antibody is operably-linked to a therapeutic agent or a detectable label.

7. The composition of claim 4, further comprising a second anti-GM-CSF antibody.

8. A B cell clone expressing the antibody of claim 1, 2, or 3.

9. A method of inhibiting a biological activity of GM-CSF in a subject comprising administering to the subject the composition of claim 4.

10. The method of claim 9, wherein the subject has an infectious disease, an inflammatory disease, an autoimmune disorder, Alzheimer's Disease, vascular dementia (VAD), or cancer.

11. The method of claim 9, wherein the subject has an inflammatory disease.

12. The method of claim 11, wherein the inflammatory disease is selected from the group consisting of asthma, acute inflammation, chronic inflammation, type I diabetes, type II diabetes and all of the related pathologies, rheumatoid arthritis, autoimmune disease, inflammatory renal disease, inflammatory lung disorders such as asthma and chronic obstructive pulmonary disease (COPD), multiple sclerosis, and autoimmune encephalomyelitis.

13. The method of claim 9, wherein the subject has cancer.

14. The method of claim 13, wherein the cancer is selected from the group consisting of colon cancer, lung cancer, breast cancer, pancreatic cancer, leukemia, and juvenile myelomonocytic leukemia.

15. The method of claim 9, further comprising administering a second anti-GM-CSF antibody.

16. The method of claim 15, wherein the second antibody is administered simultaneously or sequentially with respect to the composition of claim 4.

17. A therapeutic kit comprising the antibody of claim 1, 2, or 3.

18. A therapeutic kit comprising the composition of claim 4.

19. The method of claim 9, wherein the subject has an infectious disease.

20. The method of claim 19, wherein the infectious disease is selected from the group consisting of sepsis, severe acute respiratory syndrome (SARS; caused by SARS-associated coronavirus), hepatitis type B or type C, influenza, varicella, adenovirus, herpes simplex virus type I or type II, rinderpest, rhinovirus, echovirus, rotavirus, respiratory syncytial virus, papilloma virus, papova virus, cytomegalovirus, echinovirus, arbovirus, hantavirus, coxsachie virus, mumps virus, measles virus, rubella virus, polio virus, human immunodeficiency virus (HIV) type I or type II, Meningitis, Septic arthritis, Peritonitis, Pneumonia, Epiglottitis, *E. coli*, Hemolytic uremic syndrome, thrombocytopenia, to, Ebola, *Staphylococcus* A-E, Plasmodium, Malaria, Dengue, hemorrhagic fever, Leishmaniasis, Leprosy, Toxic shock syndrome, *Streptococcal myositis*, Gas gangrene, *Mycobacterium*, Pneumocystis, Pelvic inflammatory disease, Orchitis/epidydimitis, *Legionella*, Lyme disease Influenza A, Epstein-Barr Virus, Viral associated hemiaphagocytic syndrome, viral encephalitis, aseptic meningitis, mycoplasma, *Neisseria, Legionella, Rickettsia*, and *Chlamydia*.

\* \* \* \* \*